US007777018B2

(12) United States Patent
Joliffe et al.

(10) Patent No.: US 7,777,018 B2
(45) Date of Patent: Aug. 17, 2010

(54) CDR-GRAFTED ANTI-TISSUE FACTOR ANTIBODIES AND METHODS OF USE THEREOF

(75) Inventors: Linda K. Joliffe, Belle Mead, NJ (US); Robert A. Zivin, Lawrenceville, NJ (US); Virginia L. Pulito, Flemington, NJ (US)

(73) Assignee: Centocor, Inc., Malvern, PA (US)

( * ) Notice: Subject to any disclaimer, the term of this patent is extended or adjusted under 35 U.S.C. 154(b) by 0 days.

(21) Appl. No.: 11/926,684

(22) Filed: Oct. 29, 2007

(65) Prior Publication Data

US 2008/0226628 A1 Sep. 18, 2008

Related U.S. Application Data

(60) Continuation of application No. 11/591,361, filed on Nov. 1, 2006, now Pat. No. 7,544,790, which is a division of application No. 10/313,392, filed on Dec. 4, 2002, now Pat. No. 7,235,380, which is a continuation of application No. 08/480,120, filed on Jun. 7, 1995, now abandoned.

(51) Int. Cl.
  *C07H 21/04* (2006.01)
  *C12P 21/08* (2006.01)
(52) U.S. Cl. .................................. 536/23.53; 530/387.3
(58) Field of Classification Search ........................ None
  See application file for complete search history.

(56) References Cited

U.S. PATENT DOCUMENTS

| 5,223,427 | A | 6/1993 | Edgington et al. |
| 5,589,173 | A | 12/1996 | O'Brien et al. |
| 6,274,142 | B1 | 8/2001 | O'Brien et al. |

FOREIGN PATENT DOCUMENTS

| EP | 1 069 185 A1 | 2/1999 |
| WO | WO 88/07543 A1 | 10/1988 |
| WO | WO 91/09968 A1 | 7/1991 |
| WO | WO 93/11237 A1 | 6/1993 |
| WO | WO 94/05328 A1 | 3/1994 |
| WO | WO 94/11029 A1 | 5/1994 |
| WO | WO 01/70984 A2 | 9/2001 |

OTHER PUBLICATIONS

Paul. Fundamental Immunology, 3$^{rd}$. Ed. Raven Press, New York. 1993.*
Ward. Antibody engineering: the use of *Escherichia coli* as an expression host. FASEB Journal, 1992. vol. 6, pp. 2422-2427.*
Ruf, Wolfram et al, Purification, sequence and crystallization of an anti-tissue factor Fab and its use for the crystallization of tissue factor, Journal of Crystal Growth 122 (1992), 253-264.

Morrisey et al. (1988) "Monoclonal antibody analysis of purified and cell-associated tissue factor" *Thrombosis Research* 52: 2.
Morrisey et al (1987) "Molecular cloning of the cDNA for tissue factor, the cellular receptor for the initiation of the coagulation protease cascade" *Cell* 50: 129-135.
Owens et al. (1994) "The genetic engineering of monoclonal antibodies" *Journal of Immunological Methods* 168:149-165.
Ruf et al. (1991) "An anti-tissue factor monoclonal antibody which inhibits TF-VIIa complex is a potent anticoagulant in plasma" *Thrombosis and Haemostasis* 66: 529-533.
Winter et al. (1993) "Humanized antibodies" *Immunology Today* 14: 243.
Fiore, Martina et al, (1992) An Unusual Antibody that Blocks Tissue Factor/Factor VIIa Function by Inhibiting cleavage Only of Macromolecular Substrates *Blood*, vol. 80, No. 12, 3127-3134.
Ragni, Massimo et al, (1996) "Monoclonal Antibody Against Tissue Factor Shortens Tissue Plasminogen Activator Lysis Time and Prevents Reocclusion in a Rabbit Model of Carotid Artery Thrombosis" *Circulation* vol. 93, No. 10, 1913-1918.
Ardissino, Diego et al. (2001) "Thrombogenic potential of human coronary atherosclerotic plaques" *Blood* vol. 98, No. 9, 2726-2729.
Presta, Leonard et al. (2001) "Generation of a Humanized, High affinity Anti-tissue Factor Antibody for Use as Novel Antithrombotic Therapeutic" *Thromb Haemost* 2001; 85: 379-89.
Carson, Steven et al. (1987) "An Inhibitory Monoclonal Antibody Against Human Tissue Factor" *Blood*, vol. 70, No. 2: 490-493.
Paborsky, Lisa et al. (1990) "Mammalian cell transient expression of tissue factor for the production of antigen" *Protein Engineering*, vol. 3, No. 6, 547-553.
Tanaka, H et al. (1985) "Purification of Glycosylated Apoprotein of Tissue Factor from Human Brain and Inhibition of its Procoagulant Activity by a Specific Antibody." *Thrombosis Research* 40: 745-756.
Kirchhofer, Daniel et al. (2000) "Epitope Location on Tissue Factor Determines the Anticoagulant Potency of Monoclonal Anti-tissue Factor Antibodies", *Thromb Haemost* 2000, 84:1072-81.
Huang, Mingdong et al. (1998) "The Mechanism of an Inhibitory Antibody on TF-initiated Blood Coagulation Revealed by the Crystal Structures of Human Tissue Factor, Fab 5G9 and TF 5G9 Complex." *J. Mol. Biol.* 275, 873-894. * cited by examiner

*Primary Examiner*—Larry R. Helms
*Assistant Examiner*—Anne M. Gussow
(74) *Attorney, Agent, or Firm*—Kenneth J. Dow

(57) ABSTRACT

The present invention provides CDR-grated antibodies against human tissue factor that retain the high binding affinity of rodent monoclonal antibodies against tissue factor but have reduced immunogenicity. The present humanized antibodies are potent anticoagulants and are thus useful in the treatment and prophylaxis of human thrombotic disease. The invention also provides methods of making the CFR-grafted antibodies and pharmaceutical compositions for the attenuation or prevention of coagulation.

3 Claims, 53 Drawing Sheets

```
                  10              20              30              40
                   *               *               *               *
        GGT CCT TAC A ATG AAA TGC AGC TGG GTC ATC TTC TTC CTG ATG GCA GTG
        CCA GGA ATG T TAC TTT ACG TCG ACC CAG TAG AAG AAG GAC TAC CGT CAC
                      Met Lys Cys Ser Trp Val Ile Phe Phe Leu Met Ala Val>

50              60              70              80              90
     *               *               *               *               *
   GTT ACA GGG GTC AAT TCA GAG ATT CAG CTG CAG CAG TCT GGG GCT GAG
   CAA TGT CCC CAG TTA AGT CTC TAA GTC GAC GTC GTC AGA CCC CGA CTC
   Val Thr Gly Val Asn Ser Glu Ile Gln Leu Gln Gln Ser Gly Ala Glu>

100             110             120             130             140
         *               *               *               *               *
    CTT GTG AGG CCA GGG GCC TTA GTC AAG TTG TCC TGC AAA GCT TCT GGC
    GAA CAC TCC GGT CCC CGG AAT CAG TTC AAC AGG ACG TTT CGA AGA CCG
    Leu Val Arg Pro Gly Ala Leu Val Lys Leu Ser Cys Lys Ala Ser Gly>

150             160             170             180             190
             *               *               *               *               *
       TTC AAC ATT AAA GAC TAC TAT ATG CAC TGG GTG AAG CAG AGG CCT GAA
       AAG TTG TAA TTT CTG ATG ATA TAC GTG ACC CAC TTC GTC TCC GGA CTT
       Phe Asn Ile Lys Asp Tyr Tyr Met His Trp Val Lys Gln Arg Pro Glu>

200             210             220             230             240
                *               *               *               *               *
       CAG GGC CTG GAG TGG ATT GGA TTG ATT GAT CCT GAG AAT GGT AAT ACT
       GTC CCG GAC CTC ACC TAA CCT AAC TAA CTA GGA CTC TTA CCA TTA TGA
       Gln Gly Leu Glu Trp Ile Gly Leu Ile Asp Pro Glu Asn Gly Asn Thr>

250             260             270             280
                   *               *               *               *
       ATA TAT GAC CCG AAG TTC CAG GGC AAG GCC AGT ATA ACA GCA GAC ACA
       TAT ATA CTG GGC TTC AAG GTC CCG TTC CGG TCA TAT TGT CGT CTG TGT
       Ile Tyr Asp Pro Lys Phe Gln Gly Lys Ala Ser Ile Thr Ala Asp Thr>

290             300             310             320             330
     *               *               *               *               *
   TCC TCC AAC ACA GCC TAC CTG CAG CTC AGC AGC CTG ACA TCT GAG GAC
   AGG AGG TTG TGT CGG ATG GAC GTC GAG TCG TCG GAC TGT AGA CTC CTG
   Ser Ser Asn Thr Ala Tyr Leu Gln Leu Ser Ser Leu Thr Ser Glu Asp>
```

FIG.1A

```
     340           350           360           370           380
      *             *             *             *             *
ACT GCC GTC TAT TAC TGT GCT AGA GAT AAC TCG TAC TAC TTT GAC TAC
TGA CGG CAG ATA ATG ACA CGA TCT CTA TTG AGC ATG ATG AAA CTG ATG
Thr Ala Val Tyr Tyr Cys Ala Arg Asp Asn Ser Tyr Tyr Phe Asp Tyr>

390           400           410           420           430
      *             *             *             *             *
TGG GGC CAA GGC ACC ACT CTC ACA GTC TCC TCA GCC AAA ACG ACA CCC
ACC CCG GTT CCG TGG TGA GAG TGT CAG AGG AGT CGG TTT TGC TGT GGG
Trp Gly GLn Gly Thr Thr Leu Thr Val Ser Ser Ala Lys Thr Thr Pro>

440           450           460           470           480
      *             *             *             *             *
CCA TCT GTC TAT CCA CTG GCC CCT GGA TCT GCT GCC CAA ACT AAC TCC
GGT AGA CAG ATA GGT GAC CGG GGA CCT AGA CGA CGG GTT TGA TTG AGG
Pro Ser Val Tyr Pro Leu Ala Pro Gly Ser Ala Ala Gln Thr Asn Ser>

490           500           510           520
      *             *             *             *
ATG GTG ACC CTG GGA TGC CTG GTC AAG GGC TAT TTC CCT GAG CCA GTG
TAC CAC TGG GAC CCT ACG GAC CAG TTC CCG ATA AAG GGA CTC GGT CAC
Met Val Thr Leu Gly Cys Leu Val Lys Gly Tyr Phe Pro Glu Pro Val>

530           540           550           560           570
  *             *             *             *             *
ACA GTG ACC TGG AAC TCT GGA TCC CTG TCC AGC GGT GTG CAC ACC TTC
TGT CAC TGG ACC TTG AGA CCT AGG GAC AGG TCG CCA CAC GTG TGG AAG
Thr Val Thr Trp Asn Ser Gly Ser Leu Ser Ser Gly Val His Thr Phe>

580           590           600           610           620
      *             *             *             *             *
CCA GCT GTC CTG CAG TCT GAC CTC TAC ACT CTG AGC AGC TCA GTG ACT
GGT CGA CAG GAC GTC AGA CTG GAG ATG TGA GAC TCG TCG AGT CAC TGA
Pro Ala Val Leu Gln Ser Asp Leu Tyr Thr Leu Ser Ser Ser Val Thr>

630           640           650           660           670
      *             *             *             *             *
GTG CCC TCC AGC ACC TGG CCC AGC GAG ACC GTC ACC TGC AAC GTT GCC
CAC GGG AGG TCG TGG ACC GGG TCG CTC TGG CAG TGG ACG TTG CAA CGC
Val Pro Ser Ser Thr Trp Pro Ser Glu Thr Val Thr Cys Asn Val Ala>
```

FIG.1B

```
        680         690         700         710         720
         *           *           *           *           *
CAC CCG GCC ACC AGC ACC AAG GTG GAC AAG AAA ATT GTG CCC AGG GAT
GTG GGC CGG TCG TCG TGG TTC CAC CTG TTC TTT TAA CAC GGG TCC CTA
His Pro Ala Ser Ser Thr Lys Val Asp Lys Lys Ile Val Pro Arg Asp>

730         740         750         760
         *           *           *           *
TGT GGT TGT AAG CCT TGC ATA TGT ACA GTC CCA GAA GTA TCA TCT GTC
ACA CCA ACA TTC GGA ACG TAT ACA TGT CAG GGT CTT CAT AGT AGA CAG
Cys Gly Cys Lys Pro Cys Ile Cys Thr Val Pro Glu Val Ser Ser Val>

770         780         790         800         810
 *           *           *           *           *
TTC ATC TTC CCC CCA AAG CCC AAG GAT GTG CTC ACC ATT ACT CTG ACT
AAG TAG AAG GGG GGT TTC GGG TTC CTA CAC GAG TGG TAA TGA GAC TGA
Phe Ile Phe Pro Pro Lys Pro Lys Asp Val Leu Thr Ile Thr Leu Thr>

820         830         840         850         860
  *           *           *           *           *
CCT AAG GTC ACG TGT GTT GTG GTA GAC ATC AGC AAG GAT GAT CCC GAG
GGA TTC CAG TGC ACA CAA CAC CAT CTG TAG TCG TTC CTA CTA GGG CTC
Pro Lys Val Thr Cys Val Val Val Asp Ile Ser Lys Asp Asp Pro Glu>

870         880         890         900         910
         *           *           *           *           *
GTC CAG TTC AGC TGG TTT GTA GAT GAT GTG GAG GTG CAC ACA GCT CAG
CAG GTC AAG TCG ACC AAA CAT CTA CTA CAC CTC CAC GTG TGT CGA GTC
Val Gln Phe Ser Trp Phe Val Asp Asp Val Glu Val His Thr Ala Gln>

920         930         940         950         960
         *           *           *           *           *
ACG CAA CCC CGG GAG GAG CAG TTC AAC AGC ACT TTC CGC TCA GTC AGT
TGC GTT GGG GCC CTC CTC GTC AAG TTG TCG TGA AAG GCG AGT CAG TCA
Thr Gln Pro Arg Glu Glu Gln Phe Asn Ser Thr Phe Arg Ser Val Ser>

970         980         990         1000
         *           *           *           *
GAA CTT CCC ATC ATG CAC CAG GAC TGG CTC AAT GGC AAG GAG TTC AAA
CTT GAA GGG TAG TAC GTG GTC CTG ACC GAG TTA CCG TTC CTC AAG TTT
Glu Leu Pro Ile Met His Gln Asp Trp Leu Asn Gly Lys Glu Phe Lys>
```

FIG.1C

```
1010          1020          1030          1040          1050
  *             *             *             *             *
TGC AGG GTC AAC AGT GCA GCT TTC CCT GCC CCC ATC GAG AAA ACC ATC
ACG TCC CAG TTG TCA CGT CGA AAG GGA CGG GGG TAG CTC TTT TGG TAG
Cys Arg Val Asn Ser Ala Ala Phe Pro Ala Pro Ile Glu Lys Thr Ile>

1060          1070          1080          1090          1100
  *             *             *             *             *
TCC AAA ACC AAA GGC AGA CCG AAG GCT CCA CAG GTG TAC ACC ATT CCA
AGG TTT TGG TTT CCG TCT GGC TTC CGA GGT GTC CAC ATG TGG TAA GGT
Ser Lys Thr Lys Gly Arg Pro Lys Ala Pro Gln Val Tyr Thr Ile Pro>

1110          1120          1130          1140          1150
    *             *             *             *             *
CCT CCC AAG GAG CAG ATG GCC AAG GAT AAA GTC AGT CTG ACC TGC ATG
GGA GGG TTC CTC GTC TAC CGG TTC CTA TTT CAG TCA GAC TGG ACG TAC
Pro Pro Lys Glu Gln Met Ala Lys Asp Lys Val Ser Leu Thr Cys Met>

1160          1170          1180          1190          1200
        *             *             *             *             *
ATA ACA GAC TTC TTC CCT GAA GAC ATT ACT GTG GAG TGG CAG TGG AAT
TAT TGT CTG AAG AAG GGA CTT CTG TAA TGA CAC CTC ACC GTC ACC TTA
Ile Thr Asp Phe Phe Pro Glu Asp Ile Thr Val Glu Trp Gln Trp Asn>

1210          1220          1230          1240
          *             *             *             *
GGG CAG CCA GCG GAG AAC TAC AAG AAC ACT CAG CCC ATC ATG GAC ACA
CCC GTC GGT CGC CTC TTG ATG TTC TTG TGA GTC GGG TAG TAC CTG TGT
Gly Gln Pro Ala Glu Asn Tyr Lys Asn Thr Gln Pro Ile Met Asp Thr>

1250          1260          1270          1280          1290
  *             *             *             *             *
GAT GGC TCT TAC TTC GTC TAC AGC AAG CTC AAT GTG CAG AAG AGC AAC
CTA CCG AGA ATG AAG CAG ATG TCG TTC GAG TTA CAC GTC TTC TCG TTG
Asp Gly Ser Tyr Phe Val Tyr Ser Lys Leu Asn Val Gln Lys Ser Asn>

1300          1310          1320          1330          1340
    *             *             *             *             *
TGG GAG GCA GGA AAT ACT TTC ACC TGC TCT GTG TTA CAT GAG GGC CTG
ACC CTC CGT CCT TTA TGA AAG TGG ACG AGA CAC AAT GTA CTC CCG GAC
Trp Glu Ala Gly Asn Thr Phe Thr Cys Ser Val Leu His Glu Gly Leu>
```

FIG.1D

```
     1350          1360          1370          1380          1390
       *             *             *             *             *
CAC AAC CAC CAT ACT GAG AAG AGC CTC TCC CAC TCT CCT GGT AAA TG ATC
GTG TTG GTG GTA TGA CTC TTC TCG GAG AGG GTG AGA GGA CCA TTT AC TAG
His Asn His His Thr Glu Lys Ser Leu Ser His Ser Pro Gly Lys >

1400          1410          1420          1430          1440
       *             *             *             *             *
CCA GTG TCC TTG GAG CCC TCT GGT CCT ACA GGA CTC TGA CAC CTA CCT
GGT CAC AGG AAC CTC GGG AGA CCA GGA TGT CCT GAG ACT GTG GAT GGA 1450          1460          1470          1480
       *             *             *             *
CCA CCC CTC CCT GTA TAA ATA AAG CAC CCA GCA CTG CCT TGG ACC C
GGT GGG GAG GGA CAT ATT TAT TTC GTG GGT CGT GAC GGA ACC TGG G
```

FIG.1E

```
              10           20           30           40
               *            *            *            *
         GGA C ATG CGG GCC CCT GCT CAG TTT TTT GGG ATC TTG TTG CTC TGG TTT
         CCT G TAC GCC CGG GGA CGA GTC AAA AAA CCC TAG AAC AAC GAG ACC AAA
               Met Arg Ala Pro Ala Gln Phe Phe Gly Ile Leu Leu Leu Trp Phe>

50           60           70           80           90
      *            *            *            *            *
 CCA GGT ATC AGA TGT GAC ATC AAG ATG ACC CAG TCT CCA TCC TCC ATG
 GGT CCA TAG TCT ACA CTG TAG TTC TAC TGG GTC AGA GGT AGG AGG TAC
 Pro Gly Ile Arg Cys Asp Ile Lys Met Thr Gln Ser Pro Ser Ser Met>

100          110          120          130          140
      *            *            *            *            *
 TAT GCA TCG CTG GGA GAC AGA GTC ACT ATC ACT TGT AAG GCG AGT CAG
 ATA CGT AGC GAC CCT CTG TCT CAG TGA TAG TGA ACA TTC CGC TCA GTC
 Tyr Ala Ser Leu Gly Glu Arg Val Thr Ile Thr Cys Lys Ala Ser Gln>

150          160          170          180          190
      *            *            *            *            *
 GAC ATT AGA AAG TAT TTA AAC TGG TAC CAG CAG AAA CCA TGG AAA TCT
 CTG TAA TCT TTC ATA AAT TTG ACC ATG GTC GTC TTT GGT ACC TTT AGA
 Asp Ile Arg Lys Tyr Leu Asn Trp Tyr Gln Gln Lys Pro Trp Lys Ser>

200          210          220          230          240
      *            *            *            *            *
 CCT AAG ACC CTG ATC TAT TAT GCA ACA AGC TTG GCA GAT GGG GTC CCA
 GGA TTC TGG GAC TAG ATA ATA CGT TGT TCG AAC CGT CTA CCC CAG GGT
 Pro Lys Thr Leu Ile Tyr Tyr Ala Thr Ser Leu Ala Asp Gly Val Pro>

250          260          270          280
      *            *            *            *
 TCA AGA TTC AGT GGC AGT GGA TCT GGG CAA GAT TAT TCT CTA ACC ATC
 AGT TCT AAG TCA CCG TCA CCT AGA CCC GTT CTA ATA AGA GAT TGG TAG
 Ser Arg Phe Ser Gly Ser Gly Ser Gly Gln Asp Tyr Ser Leu Thr Ile>

290          300          310          320          330
      *            *            *            *            *
 AGC AGC CTG GAG TCT GAC GAT ACA GCA ACT TAT TAC TGT CTA CAA CAT
 TCG TCG GAC CTC AGA CTG CTA TGT CGT TGA ATA ATG ACA GAT GTT GTA
 Ser Ser Leu Glu Ser Asp Asp Thr Ala Thr Tyr Tyr Cys Leu Gln His>
```

FIG.2A

```
                340              350              360              370              380
                 *                *                *                *                *
           GGT GAG AGC CCG TAC ACG TTC GGA GGG GGG ACC AAG CTG GAA ATA AAC
           CCA CTC TCG GGC ATG TGC AAG CCT CCC CCC TGG TTC GAC CTT TAT TTG
           Gly Glu Ser Pro Tyr Thr Phe Gly Gly Gly Thr Lys Leu Glu Ile Asn>

390              400              410              420              430
                 *                *                *                *                *
           AGG GCT GAT GCT GCA CCA ACT GTA TCC ATC TTC CCA CCA TCC AGT GAG
           TCC CGA CTA CGA CGT GGT TGA CAT AGG TAG AAG GGT GGT AGG TCA CTC
           Arg Ala Asp Ala Ala Pro Thr Val Ser Ile Phe Pro Pro Ser Ser Glu>

440              450              460              470              480
                 *                *                *                *                *
           CAG TTA ACA TCT GGA GGT GCC TCA GTC GTG TGC TTC TTG AAC AAC TTC
           GTC AAT TGT AGA CCT CCA CGG AGT CAG CAC ACG AAG AAC TTG TTG AAG
           Gln Leu Thr Ser Gly Gly Ala Ser Val Val Cys Phe Leu Asn Asn Phe>

490              500              510              520
                 *                *                *                *
           TAC CCC AAA GAC ATC AAT GTC AAG TGG AAG ATT GAT GGC AGT GAA CGA
           ATG GGG TTT CTG TAG TTA CAG TTC ACC TTC TAA CTA CCG TCA CTT GCT
           Tyr Pro Lys Asp Ile Asn Val Lys Trp Lys Ile Asp Gly Ser Glu Arg>

530              540              550              560              570
           *                *                *                *                *
           CAA AAT GGC GTC CTG AAC AGT TGG ACT GAT CAG GAC AGC AAA GAC AGC
           GTT TTA CCG CAG GAC TTG TCA ACC TGA CTA GTC CTG TCG TTT CTG TCG
           Gln Asn Gly Val Leu Asn Ser Trp Thr Asp Gln Asp Ser Lys Asp Ser>

580              590              600              610              620
                 *                *                *                *                *
           ACC TAC AGC ATG AGC AGC ACC CTC ACG TTG ACC AAG GAC GAG TAT GAA
           TGG ATG TCG TAC TCG TCG TGG GAG TGC AAC TGG TTC CTG CTC ATA CTT
           Thr Tyr Ser Met Ser Ser Thr Leu Thr Leu Thr Lys Asp Glu Tyr Glu>

630              640              650              660              670
                 *                *                *                *                *
           CGA CAT AAC AGC TAT ACC TGT GAG GCC ACT CAC AAG ACA TCA ACT TCA
           GCT GTA TTG TCG ATA TGG ACA CTC CCG TGA GTG TTC TGT AGT TGA AGT
           Arg His Asn Ser Tyr Thr Cys Glu Ala Thr His Lys Thr Ser Thr Ser>
```

FIG.2B

```
        680           690           700           710           720
         *             *             *             *
CCC ATT GTC AAG AGC TTC AAC AGG AAT GAG TGT TA GAG ACA AAG GTC CTG
GGG TAA CAG TTC TCG AAG TTG TCC TTA CTC ACA AT CTC TGT TTC CAG GAC
Pro Ile Val Lys Ser Phe Asn Arg Asn Glu Cys>

730           740           750           760           770
         *             *             *             *             *
AGA CGC CAC CAC CAG CTC CCC AGC TCC ATC CTA TCT TCC CTT CTA AGG
TCT GCG GTG GTG GTC GAG GGG TCG AGG TAG GAT AGA AGG GAA GAT TCC 780           790           800           810
         *             *             *             *
TCT TGG AGG CTT CCC CAC AAG CGA CCT ACC ACT GTT GCG GTG CTC CAA
AGA ACC TCC GAA GGG GTG TTC GCT GGA TGG TGA CAA CGC CAC GAG GTT 820          830           840           850           860
 *            *             *             *             *
ACC TCC TCC CCA CCT CCT TCT CCT CCT CCT CCC TTT CCT TGG CTT TTA
TGG AGG AGG GGT GGA GGA AGA GGA GGA GGA GGG AAA GGA ACC GAA AAT 870           880           890           900           910
         *             *             *             *             *
TCA TGC TAA TAT TTG CAG AAA ATA TTC AAT AAA GTG AGT CTT TGC ACT
AGT ACG ATT ATA AAC GTC TTT TAT AAG TTA TTT CAC TCA GAA ACG TGA 920           930
         *             *
TGA AAA AAA AAA AAA AAA AAA A
ACT TTT TTT TTT TTT TTT TTT T
```

FIG.2C

```
            10                  20                  30                  40
             *                   *                   *                   *
GAA TTC GCC GCC ACC ATG GAA TGG AGC TGG GTC TTT CTC TTC TTC TTG
CTT AAG CGG CGG TGG TAC CTT ACC TCG ACC CAG AAA GAG AAG AAG AAC
                    Met Glu Trp Ser Trp Val Phe Leu Phe Phe Leu>

50                  60                  70                  80                  90
     *                   *                   *                   *                   *
TCA GTA ACT ACA GGT GTA CAC TCA CAA GTT CAG CTG GTG GAG TCT GGA
AGT CAT TGA TGT CCA CAT GTG AGT GTT CAA GTC GAC CAC CTC AGA CCT
Ser Val Thr Thr Gly Val His Ser Gln Val Gln Leu Val Glu Ser Gly>

100                 110                 120                 130                 140
     *                   *                   *                   *                   *
GGA GGA GTA GTA CAA CCT GGA AGG TCA CTG AGA CTG TCT TGT AAG GCT
CCT CCT CAT CAT GTT GGA CCT TCC AGT GAC TCT GAC AGA ACA TTC CGA
Gly Gly Val Val Gln Pro Gly Arg Ser Leu Arg Leu Ser Cys Lys Ala>

150                 160                 170                 180                 190
     *                   *                   *                   *                   *
AGT GGA TTC AAT ATC AAG GAC TAT TAT ATG CAC TGG GTC AGA CAA GCT
TCA CCT AAG TTA TAG TTC CTG ATA ATA TAC GTG ACC CAG TCT GTT CGA
Ser Gly Phe Asn Ile Lys Asp Tyr Tyr Met His Trp Val Arg Gln Ala>

200                 210                 220                 230                 240
     *                   *                   *                   *                   *
CCT GGA AAA GGA CTC GAG TGG ATA GGT TTA ATT GAT CCT GAG AAT GGT
GGA CCT TTT CCT GAG CTC ACC TAT CCA AAT TAA CTA GGA CTC TTA CCA
Pro Gly Lys Gly Leu Glu Trp Ile Gly Leu Ile Asp Pro Glu Asn Gly>

250                 260                 270                 280
     *                   *                   *                   *
AAC ACG ATA TAT GAT CCC AAG TTC CAA GGA AGA TTC ACA ATT TCT GCA
TTG TGC TAT ATA CTA GGG TTC AAG GTT CCT TCT AAG TGT TAA AGA CGT
Asn Thr Ile Tyr Asp Pro Lys Phe Gln Gly Arg Phe Thr Ile Ser Ala>

290                 300                 310                 320                 330
     *                   *                   *                   *                   *
GAC AAC TCT AAG AAT ACA CTG TTC CTG CAG ATG GAC TCA CTC AGA CCT
CTG TTG AGA TTC TTA TGT GAC AAG GAC GTC TAC CTG AGT GAG TCT GGA
Asp Asn Ser Lys Asn Thr Leu Phe Leu Gln Met Asp Ser Leu Arg Pro>
```

FIG.4A

```
        340         350         360         370         380
         *           *           *           *           *
GAG GAT ACA GCA GTC TAC TAT TGT GCT AGA GAT AAC AGT TAT TAC TTC
CTC CTA TGT CGT CAG ATG ATA ACA CGA TCT CTA TTG TCA ATA ATG AAG
Glu Asp Thr Ala Val Tyr Tyr Cys Ala Arg Asp Asn Ser Tyr Tyr Phe>

390         400         410         420         430
         *           *           *           *           *
GAC TAC TGG GGC CAA GGA ACA CCA GTC ACC GTG AGC TCA GCT TCC ACC
CTG ATG ACC CCG GTT CCT TGT GGT CAG TGG CAC TCG AGT CGA AGG TGG
Asp Tyr Trp Gly Gln Gly Thr Pro Val Thr Val Ser Ser Ala Ser Thr>

440         450         460         470         480
         *           *           *           *           *
AAG GGC CCA TCC GTC TTC CCC CTG GCG CCC TGC TCC AGG AGC ACC TCC
TTC CCG GGT AGG CAG AAG GGG GAC CGC GGG ACG AGG TCC TCG TGG AGG
Lys Gly Pro Ser Val Phe Pro Leu Ala Pro Cys Ser Arg Ser Thr Ser>

490         500         510         520
              *           *           *           *
GAG AGC ACA GCC GCC CTG GGC TGC CTG GTC AAG GAC TAC TTC CCC GAA
CTC TCG TGT CGG CGG GAC CCG ACG GAC CAG TTC CTG ATG AAG GGG CTT
Glu Ser Thr Ala Ala Leu Gly Cys Leu Val Lys Asp Tyr Phe Pro Glu>

530         540         550         560         570
 *           *           *           *           *
CCG GTG ACG GTG TCG TGG AAC TCA GGC GCC CTG ACC AGC GGC GTG CAC
GGC CAC TGC CAC AGC ACC TTG AGT CCG CGG GAC TGG TCG CCG CAC GTG
Pro Val Thr Val Ser Trp Asn Ser Gly Ala Leu Thr Ser Gly Val His>

580         590         600         610         620
         *           *           *           *           *
ACC TTC CCG GCT GTC CTA CAG TCC TCA GGA CTC TAC TCC CTC AGC AGC
TGG AAG GGC CGA CAG GAT GTC AGG AGT CCT GAG ATG AGG GAG TCG TCG
Thr Phe Pro Ala Val Leu Gln Ser Ser Gly Leu Tyr Ser Leu Ser Ser>

630         640         650         660         670
         *           *           *           *           *
GTG GTG ACC GTG CCC TCC AGC AGC TTG GGC ACG AAG ACC TAC ACC TGC
CAC CAC TGG CAC GGG AGG TCG TCG AAC CCG TGC TTC TGG ATG TGG ACG
Val Val Thr Val Pro Ser Ser Ser Leu Gly Thr Lys Thr Tyr Thr Cys>
```

FIG.4B

```
         680         690         700         710         720
          *           *           *           *           *
AAC GTA GAT CAC AAG CCC AGC AAC ACC AAG GTG GAC AAG AGA GTT GGT
TTG CAT CTA GTG TTC GGG TCG TTG TGG TTC CAC CTG TTC TCT CAA CCA
Asn Val Asp His Lys Pro Ser Asn Thr Lys Val Asp Lys Arg Val>

730         740         750         760
          *           *           *           *
GAG AGG CCA GCA CAG GGC AGG GAG GGT GTC TGC TGG AAG CCA GGC TCA
CTC TCC GGT CGT GTC CCG TCC CTC CCA CAG ACG ACC TTC GGT CCG AGT 770         780         790         800         810
  *           *           *           *           *
GCC CTC CTG CCT GGA CGC ACC CCG GCT GTG CAG CCC CAG CCC AGG GCA
CGG GAG GAC GGA CCT GCG TGG GGC CGA CAC GTC GGG GTC GGG TCC CGT 820         830         840         850         860
     *           *           *           *           *
GCA AGG CAT GCC CCA TCT GTC TCC TCA CCC GGA GGC CTC TGA CCA CCC
CGT TCC GTA CGG GGT AGA CAG AGG AGT GGG CCT CCG GAG ACT GGT GGG 870         880         890         900         910
     *           *           *           *           *
CAC TCA TGC TCA GGG AGA GGG TCT TCT GGA TTT TTC CAC CAG GCT CCG
GTG AGT ACG AGT CCC TCT CCC AGA AGA CCT AAA AAG GTG GTC CGA GGC 920         930         940         950         960
     *           *           *           *           *
GGC AGC CAC AGG CTG GAT GCC CCT ACC CCA GGC CCT GCG CAT ACA GGG
CCG TCG GTG TCC GAC CTA CGG GGA TGG GGT CCG GGA CGC GTA TGT CCC 970         980         990        1000
         *           *           *           *
GCA GGT GCT GCG CTC AGA CCT GCC AAG AGC CAT ATC CGG GAG GAC CCT
CGT CCA CGA CGC GAG TCT GGA CGG TTC TCG GTA TAG GCC CTC CTG GGA 1010        1020        1030        1040        1050
  *           *           *           *           *
GCC CCT GAC CTA AGC CCA CCC CAA AGG CCA AAC TCT CCA CTC CCT CAG
CGG GGA CTG GAT TCG GGT GGG GTT TCC GGT TTG AGA GGT GAG GGA GTC
```

FIG.4C

```
        1060           1070           1080           1090           1100
          *              *              *              *              *
CTC AGA CAC CTT CTC TCC TCC CAG ATT CGA GTA ACT CCC AAT CTT CTC
GAG TCT GTG GAA GAG AGG AGG GTC TAA GCT CAT TGA GGG TTA GAA GAG 1110           1120           1130           1140           1150
          *              *              *              *              *
TCT GCA GAG TCC AAA TAT GGT CCC CCA TGC CCA TCA TGC CCA GGT AAG
AGA CGT CTC AGG TTT ATA CCA GGG GGT ACG GGT AGT ACG GGT CCA TTC
    Glu Ser Lys Tyr Gly Pro Pro Cys Pro Ser Cys Pro>

1160           1170           1180           1190           1200
          *              *              *              *              *
CCA ACC CAG GCC TCG CCC TCC AGC TCA AGG CGG GAC AGG TGC CCT AGA
GGT TGG GTC CGG AGC GGG AGG TCG AGT TCC GCC CTG TCC ACG GGA TCT 1210           1220           1230           1240
          *              *              *              *
GTA GCC TGC ATC CAG GGA CAG GCC CCA GCC GGG TGC TGA CGC ATC CAC
CAT CGG ACG TAG GTC CCT GTC CGG GGT CGG CCC ACG ACT GCG TAG GTG 1250           1260           1270           1280           1290
  *              *              *              *              *
CTC CAT CTC TTC CTC AGC A  CCT GAG TTC CTG GGG GGA CCA TCA GTC TTC
GAG GTA GAG AAG GAG TCG T  GGA CTC AAG GAC CCC CCT GGT AGT CAG AAG
                           Pro Glu Phe Leu Gly Gly Pro Ser Val Phe>

1300           1310           1320           1330           1340
          *              *              *              *              *
CTG TTC CCC CCA AAA CCC AAG GAC ACT CTC ATG ATC TCC CGG ACC CCT
GAC AAG GGG GGT TTT GGG TTC CTG TGA GAG TAC TAG AGG GCC TGG GGA
Leu Phe Pro Pro Lys Pro Lys Asp Thr Leu Met Ile Ser Arg Thr Pro>

1350           1360           1370           1380           1390
          *              *              *              *              *
GAG GTC ACG TGC GTG GTG GTG GAC GTG AGC CAG GAA GAC CCC GAG GTC
CTC CAG TGC ACG CAC CAC CAC CTG CAC TCG GTC CTT CTG GGG CTC CAG
Glu Val Thr Cys Val Val Val Asp Val Ser Gln Glu Asp Pro Glu Val>
```

FIG.4D

```
        1400            1410            1420            1430            1440
          *               *               *               *               *
       CAG TTC AAC TGG TAC GTG GAT GGC GTG GAG GTG CAT AAT GCC AAG ACA
       GTC AAG TTG ACC ATG CAC CTA CCG CAC CTC CAC GTA TTA CGG TTC TGT
       Gln Phe Asn Trp Tyr Val Asp Gly Val Glu Val His Asn Ala Lys Thr>

1450            1460            1470            1480
              *               *               *               *
         AAG CCG CGG GAG GAG CAG TTC AAC AGC ACG TAC CGT GTG GTC AGC GTC
         TTC GGC GCC CTC CTC GTC AAG TTG TCG TGC ATG GCA CAC CAG TCG CAG
         Lys Pro Arg Glu Glu Gln Phe Asn Ser Thr Tyr Arg Val Val Ser Val>

1490            1500            1510            1520            1530
     *               *               *               *               *
   CTC ACC GTC CTG CAC CAG GAC TGG CTG AAC GGC AAG GAG TAC AAG TGC
   GAG TGG CAG GAC GTG GTC CTG ACC GAC TTG CCG TTC CTC ATG TTC ACG
   Leu Thr Val Leu His Gln Asp Trp Leu Asn Gly Lys Glu Tyr Lys Cys>

1540            1550            1560            1570            1580
          *               *               *               *               *
       AAG GTC TCC AAC AAA GGC CTC CCG TCC TCC ATC GAG AAA ACC ATC TCC
       TTC CAG AGG TTG TTT CCG GAG GGC AGG AGG TAG CTC TTT TGG TAG AGG
       Lys Val Ser Asn Lys Gly Leu Pro Ser Ser Ile Glu Lys Thr Ile Ser>

1590            1600            1610            1620            1630
              *               *               *               *               *
         AAA GCC AAA GG TGG GAC CCA CGG GGT GCG AGG GCC ACA TGG ACA GAG GTC
         TTT CGG TTT CC ACC CTG GGT GCC CCA CGC TCC CGG TGT ACC TGT CTC CAG
         Lys Ala Lys>

1640            1650            1660            1670            1680
              *               *               *               *               *
         AGC TCG GCC CAC CCT CTG CCC TGG GAG TGA CCG CTG TGC CAA CCT CTG
         TCG AGC CGG GTG GGA GAC GGG ACC CTC ACT GGC GAC ACG GTT GGA GAC 1690            1700            1710            1720            1730
                  *               *               *               *               *
             TCC CTA CA GGG CAG CCC CGA GAG CCA CAG GTG TAC ACC CTG CCC CCA TCC
             AGG GAT GT CCC GTC GGG GCT CTC GGT GTC CAC ATG TGG GAC GGG GGT AGG
                       Gly Gln Pro Arg Glu Pro Gln Val Tyr Thr Leu Pro Pro Ser>
```

FIG.4E

```
        1740          1750          1760          1770          1780
          *             *             *             *             *
CAG GAG GAG ATG ACC AAG AAC CAG GTC AGC CTG ACC TGC CTG GTC AAA
GTC CTC CTC TAC TGG TTC TTG GTC CAG TCG GAC TGG ACG GAC CAG TTT
Gln Glu Glu Met Thr Lys Asn Gln Val Ser Leu Thr Cys Leu Val Lys>

1790          1800          1810          1820
             *             *             *             *
GGC TTC TAC CCC AGC GAC ATC GCC GTG GAG TGG GAG AGC AAT GGG CAG
CCG AAG ATG GGG TCG CTG TAG CGG CAC CTC ACC CTC TCG TTA CCC GTC
Gly Phe Tyr Pro Ser Asp Ile Ala Val Glu Trp Glu Ser Asn Gly Gln>

1830          1840          1850          1860          1870
      *             *             *             *             *
CCG GAG AAC AAC TAC AAG ACC ACG CCT CCC GTG CTG GAC TCC GAC GGC
GGC CTC TTG TTG ATG TTC TGG TGC GGA GGG CAC GAC CTG AGG CTG CCG
Pro Glu Asn Asn Tyr Lys Thr Thr Pro Pro Val Leu Asp Ser Asp Gly>

1880          1890          1900          1910          1920
      *             *             *             *             *
TCC TTC TTC CTC TAC AGC AGG CTA ACC GTG GAC AAG AGC AGG TGG CAG
AGG AAG AAG GAG ATG TCG TCC GAT TGG CAC CTG TTC TCG TCC ACC GTC
Ser Phe Phe Leu Tyr Ser Arg Leu Thr Val Asp Lys Ser Arg Trp Gln>

1930          1940          1950          1960          1970
          *             *             *             *             *
GAG GGG AAT GTC TTC TCA TGC TCC GTG ATG CAT GAG GCT CTG CAC AAC
CTC CCC TTA CAG AAG AGT ACG AGG CAC TAC GTA CTC CGA GAC GTG TTG
Glu Gly Asn Val Phe Ser Cys Ser Val Met His Glu Ala Leu His Asn>

1980          1990          2000          2010          2020
          *             *             *             *             *
CAC TAC ACA CAG AAG AGC CTC TCC CTG TCT CTG GGT AAA T GAG TGC CAG
GTG ATG TGT GTC TTC TCG GAG AGG GAC AGA GAC CCA TTT A CTC ACG GTC
His Tyr Thr Gln Lys Ser Leu Ser Leu Ser Leu Gly Lys Xxx>

2030          2040          2050          2060          2070
             *             *             *             *             *
GGC CGG CAA GCC CCC GCT CCC CGG GCT CTC GGG GTC GCG CGA GGA TGC
CCG GCC GTT CGG GGG CGA GGG GCC CGA GAG CCC CAG CGC GCT CCT ACG
```

FIG.4F

```
            2080           2090           2100           2110
             *              *              *              *
       TTG GCA CGT ACC CCG TCT ACA TAC TTC CCA GGC ACC CAG CAT GGA AAT
       AAC CGT GCA TGG GGC AGA TGT ATG AAG GGT CCG TGG GTC GTA CCT TTA 2120           2130           2140           2150           2160
    *              *              *              *              *
  AAA GCA CCC ACC ACT GCC CTG GGC CCC TGT GAG ACT GTG ATG GTT CTT
  TTT CGT GGG TGG TGA CGG GAC CCG GGG ACA CTC TGA CAC TAC CAA GAA 2170           2180           2190           2200           2210
           *              *              *              *              *
       TCC ACG GGT CAG GCC GAG TCT GAG GCC TGA GTG ACA TGA GGG AGG CAG
       AGG TGC CCA GTC CGG CTC AGA CTC CGG ACT CAC TGT ACT CCC TCC GTC 2220           2230           2240           2250           2260
           *              *              *              *              *
       AGC GGG TCC CAC TGT CCC CAC ACT GGC CCA GGC TGT GCA GGT GTG CCT
       TCG CCC AGG GTG ACA GGG GTG TGA CCG GGT CCG ACA CGT CCA CAC GGA 2270           2280           2290           2300           2310
           *              *              *              *              *
       GGG CCA CCT AGG GTG GGG CTC AGC CAG GGG GTC CCC TCG GCA GGG TGG
       CCC GGT GGA TCC CAC CCC GAC TCG GTC CCC GAC GGG AGC CGT CCC ACC 2320           2330           2340           2350
           *              *              *              *
       GGG ATT TGC CAG CGT GGC CCT CCC TCC AGC AGC AGG ACT CTA GAG GAT
       CCC TAA ACG GTC GCA CCG GGA GGG AGG TCG TCG TCC TGA GAT CTC CTA 2360           2370           2380           2390           2400
    *              *              *              *              *
  CAT AAT CAG CCA TAC CAC ATT TGT AGA GGT TTT ACT TGC TTT AAA AAA
  GTA TTA GTC GGT ATG GTG TAA ACA TCT CCA AAA TGA ACG AAA TTT TTT 2410           2420           2430           2440           2450
    *              *              *              *              *
  CCT CCC ACA CCT CCC CCT GAA CCT GAA ACA TAA AAT GAA TGC AAT TGT
  GGA GGG TGT GGA GGG GGA CTT GGA CTT TGT ATT TTA CTT ACG TTA ACA
```

FIG.4G

```
        2460           2470           2480           2490           2500
         *              *              *              *              *
TGT TGT TAA CTT GTT TAT TGC AGC TTA TAA TGG TTA CAA ATA AAG CAA
ACA ACA ATT GAA CAA ATA ACG TCG AAT ATT ACC AAT GTT TAT TTC GTT 2510           2520           2530           2540           2550
         *              *              *              *              *
TAG CAT CAC AAA TTT CAC AAA TAA AGC ATT TTT TTC ACT GCA TTC TAG
ATC GTA GTG TTT AAA GTG TTT ATT TCG TAA AAA AAG TGA CGT AAG ATC 2560           2570           2580           2590
              *              *              *              *
    TTG TGG TTT GTC CAA ACT CAT CAA TGT ATC TTA TCA TGT CTG GAT CCT
    AAC ACC AAA CAG GTT TGA GTA GTT ACA TAG AAT AGT ACA GAC CTA GGA 2600           2610           2620           2630           2640
 *              *              *              *              *
CTA CGC CGG ACG CAT CGT GGC CGG CAT CAC CGG CGC CAC AGG TGC GGT
GAT GCG GCC TGC GTA GCA CCG GCC GTA GTG GCC GCG GTG TCC ACG CCA 2650           2660           2670           2680           2690
         *              *              *              *              *
TGC TGG CGC CTA TAT CGC CGA CAT CAC CGA TGG GGA AGA TCG GGC TCG
ACG ACC GCG GAT ATA GCG GCT GTA GTG GCT ACC CCT TCT AGC CCG AGC 2700           2710           2720           2730           2740
         *              *              *              *              *
CCA CTT CGG GCT CAT GAG CGC TTG TTT CGG CGT GGC TAT GGT GGC AGG
GGT GAA GCC CGA GTA CTC GCG AAC AAA GCC GCA CCC ATA CCA CCG TCC 2750           2760           2770           2780           2790
         *              *              *              *              *
CCC GTG GCC GGG GGA CTG TTG GGC GCC ATC TCC TTG CAT GCA CCA TTC
GGG CAC CGG CCC CCT GAC AAC CCG CGG TAG AGG AAC GTA CGT GGT AAG 2800           2810           2820           2830
              *              *              *              *
    CTT GCG GCG GCG GTG CTC AAC GGC CTC AAC CTA CTA CTG GGC TGC TTC
    GAA CGC CGC CGC CAC GAG TTG CCG GAG TTG GAT GAT GAC CCG ACG AAG
```

FIG.4H

```
2840            2850            2860            2870            2880
  *               *               *               *               *
CTA ATG CAG GAG TCG CAT AAG GGA GAG CGT CGA CCT CGG GCC GGG TTG
GAT TAC GTC CTC AGC GTA TTC CCT CTC GCA GCT GGA GCC CGG CGC AAC 2890            2900            2910            2920            2930
  *               *               *               *               *
CTG GCG TTT TTC CAT AGG CTC CGC CCC CCT GAC GAG CAT CAC AAA AAT
GAC CGC AAA AAG GTA TCC GAG GCG GGG GGA CTG CTC GTA GTG TTT TTA 2940            2950            2960            2970            2980
  *               *               *               *               *
CGA CGC TCA AGT CAG AGG TGG CGA AAC CCG ACA GGA CTA TAA AGA TAC
GCT GCG AGT TCA GTC TCC ACC GCT TTG GGC TGT CCT GAT ATT TCT ATG 2990            3000            3010            3020            3030
  *               *               *               *               *
CAG GCG TTT CCC CCT GGA AGC TCC CTC GTG CGC TCT CCT GTT CCG ACC
GTC CGC AAA GGG GGA CCT TCG AGG GAG CAC GCG AGA GGA CAA GGC TGG 3040            3050            3060            3070
          *               *               *               *
CTG CCG CTT ACC GGA TAC CTG TCC GCC TTT CTC CCT TCG GGA AGC GTG
GAC GGC GAA TGG CCT ATG GAC AGG CGG AAA GAG GGA AGC CCT TCG CAC 3080            3090            3100            3110            3120
  *               *               *               *               *
GCG CTT TCT CAA TGC TCA CGC TGT AGG TAT CTC AGT TCG GTG TAG GTC
CGC GAA AGA GTT ACG AGT GCG ACA TCC ATA GAG TCA AGC CAC ATC CAG 3130            3140            3150            3160            3170
  *               *               *               *               *
GTT CGC TCC AAG CTG GGC TGT GTG CAC GAA CCC CCC GTT CAG CCC GAC
CAA GCG AGG TTC GAC CCG ACA CAC GTG CTT GGG GGG CAA GTC GGG CTG 3180            3190            3200            3210            3220
  *               *               *               *               *
CGC TGC GCC TTA TCC GGT AAC TAT CGT CTT GAG TCC AAC CCG GTA AGA
GCG ACG CGG AAT AGG CCA TTG ATA GCA GAA CTC AGG TTG GGC CAT TCT
```

FIG.41

```
              3230            3240            3250            3260            3270
                *               *               *               *               *
       CAC GAC TTA TCG CCA CTG GCA GCA GCC ACT GGT AAC AGG ATT AGC AGA
       GTG CTG AAT AGC GGT GAC CGT CGT CGG TGA CCA TTG TCC TAA TCG TCT 3280            3290            3300            3310
                    *               *               *               *
       GCG AGG TAT GTA GGC GGT GCT ACA GAG TTC TTG AAG TGG TGG CCT AAC
       CGC TCC ATA CAT CCG CCA CGA TGT CTC AAG AAC TTC ACC ACC GGA TTG 3320            3330            3340            3350            3360
       *               *               *               *               *
       TAC GGC TAC ACT AGA AGG ACA GTA TTT GGT ATC TGC GCT CTG CTG AAG
       ATG CCG ATG TGA TCT TCC TGT CAT AAA CCA TAG ACG CGA GAC GAC TTC 3370            3380            3390            3400            3410
           *               *               *               *               *
       CCA GTT ACC TTC GGA AAA AGA GTT GGT AGC TCT TGA TCC GGC AAA CAA
       GGT CAA TGG AAG CCT TTT TCT CAA CCA TCG AGA ACT AGG CCG TTT GTT 3420            3430            3440            3450            3460
                *               *               *               *               *
       ACC ACC GCT GGT AGC GGT GGT TTT TTT GTT TGC AAG CAG CAG ATT ACG
       TGG TGG CGA CCA TCG CCA CCA AAA AAA CAA ACG TTC GTC GTC TAA TGC 3470            3480            3490            3500            3510
                    *               *               *               *               *
       CGC AGA AAA AAA GGA TCT CAA GAA GAT CCT TTG ATC TTT TCT ACG GGG
       GCG TCT TTT TTT CCT AGA GTT CTT CTA GGA AAC TAG AAA AGA TGC CCC 3520            3530            3540            3550
                        *               *               *               *
       TCT GAC GCT CAG TGG AAC GAA AAC TCA CGT TAA GGG ATT TTG GTC ATG
       AGA CTG CGA GTC ACC TTG CTT TTG AGT GCA ATT CCC TAA AAC CAG TAC 3560            3570            3580            3590            3600
       *               *               *               *               *
       AGA TTA TCA AAA AGG ATC TTC ACC TAG ATC CTT TTA AAT TAA AAA TGA
       TCT AAT AGT TTT TCC TAG AAG TGG ATC TAG GAA AAT TTA ATT TTT ACT
```

FIG.4J

```
       3610            3620            3630            3640            3650
        *               *               *               *               *
AGT TTT AAA TCA ATC TAA AGT ATA TAT GAG TAA ACT TGG TCT GAC AGT
TCA AAA TTT AGT TAG ATT TCA TAT ATA CTC ATT TGA ACC AGA CTG TCA 3660            3670            3680            3690            3700
        *               *               *               *               *
TAC CAA TGC TTA ATC AGT GAG GCA CCT ATC TCA GCG ATC TGT CTA TTT
ATG GTT ACG AAT TAG TCA CTC CGT GGA TAG AGT CGC TAG ACA GAT AAA 3710            3720            3730            3740            3750
        *               *               *               *               *
CGT TCA TCC ATA GTT GCC TGA CTC CCC GTC GTG TAG ATA ACT ACG ATA
GCA AGT AGG TAT CAA CGG ACT GAG GGG CAG CAC ATC TAT TGA TGC TAT 3760            3770            3780            3790
             *               *               *               *
CGG GAG GGC TTA CCA TCT GGC CCC AGT GCT GCA ATG ATA CCG CGA GAC
GCC CTC CCG AAT GGT AGA CCG GGG TCA CGA CGT TAC TAT GGC GCT CTG 3800            3810            3820            3830            3840
 *               *               *               *               *
CCA CGC TCA CCG GCT CCA GAT TTA TCA GCA ATA AAC CAG CCA GCC GGA
GGT GCG AGT GGC CGA GGT CTA AAT AGT CGT TAT TTG GTC GGT CGG CCT 3850            3860            3870            3880            3890
        *               *               *               *               *
AGG GCC GAG CGC AGA AGT GGT CCT GCA ACT TTA TCC GCC TCC ATC CAG
TCC CGG CTC GCG TCT TCA CCA GGA CGT TGA AAT AGG CGG AGG TAG GTC 3900            3910            392Q            3930            3940
        *               *               *               *               *
TCT ATT AAT TGT TGC CGG GAA GCT AGA GTA AGT AGT TCG CCA GTT AAT
AGA TAA TTA ACA ACG GCC CTT CGA TCT CAT TCA TCA AGC GGT CAA TTA 3950            3960            3970            3980            3990
             *               *               *               *               *
AGT TTG CGC AAC GTT GTT GCC ATT GCT ACA GGC ATC GTG GTG TCA CGC
TCA AAC GCG TTG CAA CAA CGG TAA CGA TGT CCG TAG CAC CAC AGT GCG
```

FIG.4K

```
        4000            4010            4020            4030
         *               *               *               *
TCG TCG TTT GGT ATG GCT TCA TTC AGC TCC GGT TCC CAA CGA TCA AGG
AGC AGC AAA CCA TAC CGA AGT AAG TCG AGG CCA AGG GTT GCT AGT TCC 4040            4050            4060            4070            4080
     *               *               *               *               *
CGA GTT ACA TGA TCC CCC ATG TTG TGC AAA AAA GCG GTT AGC TCC TTC
GCT CAA TGT ACT AGG GGG TAC AAC ACG TTT TTT CGC CAA TCG AGG AAG 4090            4100            4110            4120            4130
     *               *               *               *               *
GGT CCT CCG ATC GTT GTC AGA AGT AAG TTG GCC GCA GTG TTA TCA CTC
CCA GGA GGC TAG CAA CAG TCT TCA TTC AAC CGG CGT CAC AAT AGT GAG 4140            4150            4160            4170            4180
         *               *               *               *               *
ATG GTT ATG GCA GCA CTG CAT AAT TCT CTT ACT GTC ATG CCA TCC GTA
TAC CAA TAC CGT CGT GAC GTA TTA AGA GAA TGA CAG TAC GGT AGG CAT 4190            4200            4210            4220            4230
         *               *               *               *               *
AGA TGC TTT TCT GTG ACT GGT GAG TAC TCA ACC AAG TCA TTC TGA GAA
TCT ACG AAA AGA CAC TGA CCA CTC ATG AGT TGG TTC AGT AAG ACT CTT 4240            4250            4260            4270
             *               *               *               *
TAG TGT ATG CGG CGA CCG AGT TGC TCT TGC CCG GCG TCA ACA CGG GAT
ATC ACA TAC GCC GCT GGC TCA ACG AGA ACG GGC CGC AGT TGT GCC CTA 4280            4290            4300            4310            4320
 *               *               *               *               *
AAT ACC GCG CCA CAT AGC AGA ACT TTA AAA GTG CTC ATC ATT GGA AAA
TTA TGG CGC GGT GTA TCG TCT TGA AAT TTT CAC GAG TAG TAA CCT TTT 4330            4340            4350            4360            4370
     *               *               *               *               *
CGT TCT TCG GGG CGA AAA CTC TCA AGG ATC TTA CCG CTG TTG AGA TCC
GCA AGA AGC CCC GCT TTT GAG AGT TCC TAG AAT GGC GAC AAC TCT AGG
```

FIG.4L

```
        4380            4390            4400            4410            4420
          *               *               *               *               *
AGT TCG ATG TAA CCC ACT CGT GCA CCC AAC TGA TCT TCA GCA TCT TTT
TCA AGC TAC ATT GGG TGA GCA CGT GGG TTG ACT AGA AGT CGT AGA AAA 4430            4440            4450            4460            4470
          *               *               *               *               *
ACT TTC ACC AGC GTT TCT GGG TGA GCA AAA ACA GGA AGG CAA AAT GCC
TGA AAG TGG TCG CAA AGA CCC ACT CGT TTT TGT CCT TCC GTT TTA CGG 4480            4490            4500            4510
              *               *               *               *
GCA AAA AAG GGA ATA AGG GCG ACA CGG AAA TGT TGA ATA CTC ATA CTC
CGT TTT TTC CCT TAT TCC CGC TGT GCC TTT ACA ACT TAT GAG TAT GAG 4520            4530            4540            4550            4560
  *               *               *               *               *
TTC CTT TTT CAA TAT TAT TGA AGC ATT TAT CAG GGT TAT TGT CTC ATG
AAG GAA AAA GTT ATA ATA ACT TCG TAA ATA GTC CCA ATA ACA GAG TAC 4570            4580            4590            4600            4610
          *               *               *               *               *
AGC GGA TAC ATA TTT GAA TGT ATT TAG AAA AAT AAA CAA ATA GGG GTT
TCG CCT ATG TAT AAA CTT ACA TAA ATC TTT TTA TTT GTT TAT CCC CAA 4620            4630            4640            4650            4660
          *               *               *               *               *
CCG CGC ACA TTT CCC CGA AAA GTG CCA CCT GAC GTC TAA GAA ACC ATT
GGC GCG TGT AAA GGG GCT TTT CAC GGT GGA CTG CAG ATT CTT TGG TAA 4670            4680            4690            4700            4710
          *               *               *               *               *
ATT ATC ATG ACA TTA ACC TAT AAA AAT AGG CGT ATC ACG AGG CCC TGA
TAA TAG TAC TGT AAT TGG ATA TTT TTA TCC GCA TAG TGC TCC GGG ACT 4720            4730            4740            4750
              *               *               *               *
TGG CTC TTT GCG GCA CCC ATC GTT CGT AAT GTT CCG TGG CAC CGA GGA
ACC GAG AAA CGC CGT GGG TAG CAA GCA TTA CAA GGC ACC GTG GCT CCT
```

FIG.4M

```
     4760           4770           4780           4790           4800
      *              *              *              *              *
CAA CCC TCA AGA GAA AAT GTA ATC ACA CTG GCT CAC CTT CGG GTG GGC
GTT GGG AGT TCT CTT TTA CAT TAG TGT GAC CGA GTG GAA GCC CAC CCG 4810           4820           4830           4840           4850
      *              *              *              *              *
CTT TCT GCG TTT ATA AGG AGA CAC TTT ATG TTT AAG AAG GTT GGT AAA
GAA AGA CGC AAA TAT TCC TCT GTG AAA TAC AAA TTC TTC CAA CCA TTT 4860           4870           4880           4890           4900
      *              *              *              *              *
TTC CTT GCG GCT TTG GCA GCC AAG CTA GAG ATC TCT AGC TTC GTG TCA
AAG GAA CGC CGA AAC CGT CGG TTC GAT CTC TAG AGA TCG AAG CAC AGT 4910           4920           4930           4940           4950
      *              *              *              *              *
AGG ACG GTG ACT GCA GTG AAT AAT AAA ATG TGT GTT TGT CCG AAA TAC
TCC TGC CAC TGA CGT CAC TTA TTA TTT TAC ACA CAA ACA GGC TTT ATG 4960           4970           4980           4990
      *              *              *              *
GCG TTT TGA GAT TTC TGT CGC CGA CTA AAT TCA TGT CGC GCG ATA GTG
CGC AAA ACT CTA AAG ACA GCG GCT GAT TTA AGT ACA GCG CGC TAT CAC 5000           5010           5020           5030           5040
 *              *              *              *              *
GTG TTT ATC GCC GAT AGA GAT GGC GAT ATT GGA AAA ATC GAT ATT TGA
CAC AAA TAG CGG CTA TCT CTA CCG CTA TAA CCT TTT TAG CTA TAA ACT 5050           5060           5070           5080           5090
      *              *              *              *              *
AAA TAT GGC ATA TTG AAA ATG TCG CCG ATG TGA GTT TCT GTG TAA CTG
TTT ATA CCG TAT AAC TTT TAC AGC GGC TAC ACT CAA AGA CAC ATT GAC 5100           5110           5120           5130           5140
      *              *              *              *              *
ATA TCG CCA TTT TTC CAA AAG TGA TTT TTG GGC ATA CGC GAT ATC TGG
TAT AGC GGT AAA AAG GTT TTC ACT AAA AAC CCG TAT GCG CTA TAG ACC
```

FIG.4N

```
        5150           5160           5170           5180           5190
          *              *              *              *              *
    CGA TAG CGC TTA TAT CGT TTA CGG GGG ATG GCG ATA GAC GAC TTT GGT
    GCT ATC GCG AAT ATA GCA AAT GCC CCC TAC CGC TAT CTG CTG AAA CCA 5200           5210           5220           5230
                 *              *              *              *
    GAC TTG GGC GAT TCT GTG TGT CGC AAA TAT CGC AGT TTC GAT ATA GGT
    CTG AAC CCG CTA AGA CAC ACA GCG TTT ATA GCG TCA AAG CTA TAT CCA 5240           5250           5260           5270           5280
     *              *              *              *              *
    GAC AGA CGA TAT GAG GCT ATA TCG CCG ATA GAG GCG ACA TCA AGC TGG
    CTG TCT GCT ATA CTC CGA TAT AGC GGC TAT CTC CGC TGT AGT TCG ACC 5290           5300           5310           5320           5330
         *              *              *              *              *
    CAC ATG GCC AAT GCA TAT CGA TCT ATA CAT TGA ATC AAT ATT GGC CAT
    GTG TAC CGG TTA CGT ATA GCT AGA TAT GTA ACT TAG TTA TAA CCG GTA 5340           5350           5360           5370           5380
          *              *              *              *              *
    TAG CCA TAT TAT TCA TTG GTT ATA TAG CAT AAA TCA ATA TTG GCT ATT
    ATC GGT ATA ATA AGT AAC CAA TAT ATC GTA TTT AGT TAT AAC CGA TAA 5390           5400           5410           5420           5430
                *              *              *              *              *
    GGC CAT TGC ATA CGT TGT ATC CAT ATC ATA ATA TGT ACA TTT ATA TTG
    CCG GTA ACG TAT GCA ACA TAG GTA TAG TAT TAT ACA TGT AAA TAT AAC 5440           5450           5460           5470
                     *              *              *              *
    GCT CAT GTC CAA CAT TAC CGC CAT GTT GAC ATT GAT TAT TGA CTA GTT
    CGA GTA CAG GTT GTA ATG GCG GTA CAA CTG TAA CTA ATA ACT GAT CAA 5480           5490           5500           5510           5520
     *              *              *              *              *
    ATT AAT AGT AAT CAA TTA CGG GGT CAT TAG TTC ATA GCC CAT ATA TGG
    TAA TTA TCA TTA GTT AAT GCC CCA GTA ATC AAG TAT CGG GTA TAT ACC
```

FIG.40

```
      5530           5540           5550           5560           5570
       *              *              *              *              *
AGT TCC GCG TTA CAT AAC TTA CGG TAA ATG GCC CGC CTG GCT GAC CGC
TCA AGG CGC AAT GTA TTG AAT GCC ATT TAC CGG GCG GAC CGA CTG GCG 5580           5590           5600           5610           5620
       *              *              *              *              *
CCA ACG ACC CCC GCC CAT TGA CGT CAA TAA TGA CGT ATG TTC CCA TAG
GGT TGC TGG GGG CGG GTA ACT GCA GTT ATT ACT GCA TAC AAG GGT ATC 5630           5640           5650           5660           5670
       *              *              *              *              *
TAA CGC CAA TAG GGA CTT TCC ATT GAC GTC AAT GGG TGG AGT ATT TAC
ATT GCG GTT ATC CCT GAA AGG TAA CTG CAG TTA CCC ACC TCA TAA ATG 5680           5690           5700           5710
        *              *              *              *
GGT AAA CTG CCC ACT TGG CAG TAC ATC AAG TGT ATC ATA TGC CAA GTA
CCA TTT GAC GGG TGA ACC GTC ATG TAG TTC ACA TAG TAT ACG GTT CAT 5720          5730           5740           5750           5760
 *             *              *              *              *
CGC CCC CTA TTG ACG TCA ATG ACG GTA AAT GGC CCG CCT GGC ATT ATG
GCG GGG GAT AAC TGC AGT TAC TGC CAT TTA CCG GGC GGA CCG TAA TAC 5770           5780           5790           5800           5810
       *              *              *              *              *
CCC AGT ACA TGA CCT TAT GGG ACT TTC CTA CTT GGC AGT ACA TCT ACG
GGG TCA TGT ACT GGA ATA CCC TGA AAG GAT GAA CCG TCA TGT AGA TGC 5820           5830           5840           5850           5860
       *              *              *              *              *
TAT TAG TCA TCG CTA TTA CCA TGG TGA TGC GGT TTT GGC AGT ACA TCA
ATA ATC AGT AGC GAT AAT GGT ACC ACT ACG CCA AAA CCG TCA TGT AGT 5870           5880           5890           5900           5910
       *              *              *              *              *
ATG GGC GTG GAT AGC GGT TTG ACT CAC GGG GAT TTC CAA GTC TCC ACC
TAC CCG CAC CTA TCG CCA AAC TGA GTG CCC CTA AAG GTT CAG AGG TGG
```

FIG.4P

```
              5920          5930          5940          5950
               *             *             *             *
        CCA TTG ACG TCA ATG GGA GTT TGT TTT GGC ACC AAA ATC AAC GGG ACT
        GGT AAC TGC AGT TAC CCT CAA ACA AAA CCG TGG TTT TAG TTG CCC TGA 5960          5970          5980          5990          6000
     *             *             *             *             *
    TTC CAA AAT GTC GTA ACA ACT CCG CCC CAT TGA CGC AAA TGG GCG GTA
    AAG GTT TTA CAG CAT TGT TGA GGC GGG GTA ACT GCG TTT ACC CGC CAT 6010          6020          6030          6040          6050
         *             *             *             *             *
        GGC GTG TAC GGT GGG AGG TCT ATA TAA GCA GAG CTC GTT TAG TGA ACC
        CCG CAC ATG CCA CCC TCC AGA TAT ATT CGT CTC GAG CAA ATC ACT TGG 6060          6070          6080          6090          6100
             *             *             *             *             *
            GTC AGA TCG CCT GGA GAC GCC ATC CAC GCT GTT TTG ACC TCC ATA GAA
            CAG TCT AGC GGA CCT CTG CGG TAG GTG CGA CAA AAC TGG AGG TAT CTT 6110          6120          6130          6140          6150
                 *             *             *             *             *
            GAC ACC GGG ACC GAT CCA GCC TCC GCG GCC GGG AAC GGT GCA TTG AAA
            CTG TGG CCC TGG CTA GGT CGG AGG CGC CGG CCC TTG CCA CGT AAC CTT 6160          6170          6180          6190
                     *             *             *             *
                CGC GGA TTC CCC GTG CCA AGA GTG ACG TAA GTA CCG CCT ATA GAG TCT
                GCG CCT AAG GGG CAC GGT TCT CAC TGC ATT CAT GGC GGA TAT CTC AGA 6200          6210          6220          6230          6240
         *             *             *             *             *
        ATA GGC CCA CCC CCT TGG CTT CTT ATG CAT GCT ATA CTG TTT TTG GCT
        TAT CCG GGT GGG GGA ACC GAA GAA TAC GTA CGA TAT GAC AAA AAC CGA 6250          6260          6270          6280          6290
             *             *             *             *             *
            TGG GGT CTA TAC ACC CCC GCT TCC TCA TGT TAT AGG TGA TGG TAT AGC
            ACC CCA GAT ATG TGG GGG CGA AGG AGT ACA ATA TCC ACT ACC ATA TCG
```

FIG.4Q

```
        6300              6310              6320              6330              6340
          *                 *                 *                 *                 *
TTA GCC TAT AGG TGT GGG TTA TTG ACC ATT ATT GAC CAC TCC CCT ATT
AAT CGG ATA TCC ACA CCC AAT AAC TGG TAA TAA CTG GTG AGG GGA TAA 6350              6360              6370              6380              6390
          *                 *                 *                 *                 *
GGT GAC GAT ACT TTC CAT TAC TAA TCC ATA ACA TGG CTC TTT GCC ACA
CCA CTG CTA TGA AAG GTA ATG ATT AGG TAT TGT ACC GAG AAA CGG TGT 6400              6410              6420              6430
               *                 *                 *                 *
ACT CTC TTT ATT GGC TAT ATG CCA ATA CAC TGT CCT TCA GAG ACT GAC
TGA GAG AAA TAA CCG ATA TAC GGT TAT GTG ACA GGA AGT CTC TGA CTG 6440              6450              6460              6470              6480
    *                 *                 *                 *                 *
ACG GAC TCT GTA TTT TTA CAG GAT GGG GTC TCA TTT ATT ATT TAC AAA
TGC CTG AGA CAT AAA AAT GTC CTA CCC CAG AGT AAA TAA TAA ATG TTT 6490              6500              6510              6520              6530
          *                 *                 *                 *                 *
TTC ACA TAT ACA ACA CCA CCG TCC CCA GTG CCC GCA GTT TTT ATT AAA
AAG TGT ATA TGT TGT GGT GGC AGG GGT CAC GGG CGT CAA AAA TAA TTT 6540              6550              6560              6570              6580
          *                 *                 *                 *                 *
CAT AAC GTG GGA TCT CCA CGC GAA TCT CGG GTA CGT GTT CCG GAC ATG
GTA TTG CAC CCT AGA GGT GCG CTT AGA GCC CAT GCA CAA GGC CTG TAC 6590              6600              6610              6620              6630
          *                 *                 *                 *                 *
GGC TCT TCT CCG GTA GCG GCG GAG CTT CTA CAT CCG AGC CCT GCT CCC
CCG AGA AGA GGC CAT CGC CGC CTC GAA GAT GTA GGC TCG GGA CGA GGG 6640              6650              6660              6670
               *                 *                 *                 *
ATG CCT CCA GCG ACT CAT GGT CGC TCG GCA GCT CCT TGC TCC TAA CAG
TAC GGA GGT CGC TGA GTA CCA GCG AGC CGT CGA GGA ACG AGG ATT GTC
```

FIG.4R

```
            6680          6690          6700          6710          6720
              *             *             *             *             *
         TGG AGG CCA GAC TTA GGC ACA GCA CGA TGC CCA CCA CCA CCA GTG TGC
         ACC TCC GGT CTG AAT CCG TGT CGT GCT ACG GGT GGT GGT GGT CAC ACG 6730          6740          6750          6760          6770
              *             *             *             *             *
         CGC ACA AGG CCG TGG CGG TAG GGT ATG TGT CTG AAA ATG AGC TCG GGG
         GCG TGT TCC GGC ACC GCC ATC CCA TAC ACA GAC TTT TAC TCG AGC CCC 6780          6790          6800          6810          6820
              *             *             *             *             *
         AGC GGG CTT GCA CCG CTG ACG CAT TTG GAA GAC TTA AGG CAG CGG CAG
         TCG CCC GAA CGT GGC GAC TGC GTA AAC CTT CTG AAT TCC GTC GCC GTC 6830          6840          6850          6860          6870
              *             *             *             *             *
         AAG AAG ATG CAG GCA GCT GAG TTG TTG TGT TCT GAT AAG AGT CAG AGG
         TTC TTC TAC GTC CGT CGA CTC AAC AAC ACA AGA CTA TTC TCA GTC TCC 6880          6890          6900          6910
                *             *             *             *
         TAA CTC CCG TTG CGG TGC TGT TAA CGG TGG AGG GCA GTG TAG TCT GAG
         ATT GAG GGC AAC GCC ACG ACA ATT GCC ACC TCC CGT CAC ATC AGA CTC 6920          6930          6940          6950          6960
           *             *             *             *             *
         CAG TAC TCG TTG CTG CCG CGC GCG CCA CCA GAC ATA ATA GCT GAC AGA
         GTC ATG AGC AAC GAC GGC GCG CGC GGT GGT CTG TAT TAT CGA CTG TCT 6970          6980          6990          7000          7010
              *             *             *             *             *
         CTA ACA GAC TGT TCC TTT CCA TGG GTC TTT TCT GCA GTC ACC GTC CTT
         GAT TGT CTG ACA AGG AAA GGT ACC CAG AAA AGA CGT CAG TGG CAG GAA 7020          7030          7040          7050          7060
              *             *             *             *             *
         GAC ACG AAG CTT GGG CTG CAG GTC GAT CGA CTC TAG AGG ATC GAT CCC
         CTG TGC TTC GAA CCC GAC GTC CAG CTA GCT GAG ATC TCC TAG CTA GGG

7070
                *
         CGG GCG AGC TC
         GCC CGC TCG AG                              FIG.4S
```

```
              10           20           30           40           50
               *            *            *            *            *
       AAT TCA CC  ATG GGT GTG CCA ACT CAG GTA TTA GGA TTA CTG CTG CTG TGG
       TTA AGT GG  TAC CCA CAC GGT TGA GTC CAT AAT CCT AAT GAC GAC GAC ACC
                   Met Gly Val Pro Thr Gln Val Leu Gly Leu Leu Leu Leu Trp>

60           70           80           90
                        *            *            *            *
       CTT ACA GAT GCA AGA TGT GAT ATC CAA ATG ACA CAA TCT CCT TCT TCT
       GAA TGT CTA CGT TCT ACA CTA TAG GTT TAC TGT GTT AGA GGA AGA AGA
       Leu Thr Asp Ala Arg Cys Asp Ile Gln Met Thr Gln Ser Pro Ser Ser>

100          110          120          130          140
   *            *            *            *            *
 CTA AGT GCT TCT GTC GGA GAT AGA GTA ACA ATT ACA TGT AAG GCG AGT
 GAT TCA CGA AGA CAG CCT CTA TCT CAT TGT TAA TGT ACA TTC CGC TCA
 Leu Ser Ala Ser Val Gly Asp Arg Val Thr Ile Thr Cys Lys Ala Ser>

150          160          170          180          190
              *            *            *            *            *
       CAG GAC ATT AGA AAG TAT TTA AAC TGG TAT CAG CAA AAA CCT GGG AAG
       GTC CTG TAA TCT TTC ATA AAT TTG ACC ATA GTC GTT TTT GGA CCC TTC
       Gln Asp Ile Arg Lys Tyr Leu Asn Trp Tyr Gln Gln Lys Pro Gly Lys>

200          210          220          230          240
                  *            *            *            *            *
       GCT CCT AAG CTA CTG ATT TAT TAT GCA ACA AGT TTG GCA GAT GGA GTA
       CGA GGA TTC GAT GAC TAA ATA ATA CGT TGT TCA AAC CGT CTA CCT CAT
       Ala Pro Lys Leu Leu Ile Tyr Tyr Ala Thr Ser Leu Ala Asp Gly Val>

250          260          270          280          290
                  *            *            *            *            *
       CCT TCT AGA TTT TCT GGT TCT GGC TCT GGA ACA GAC TAC ACA TTC ACA
       GGA AGA TCT AAA AGA CCA AGA CCG AGA CCT TGT CTG ATG TGT AAG TGT
       Pro Ser Arg Phe Ser Gly Ser Gly Ser Gly Thr Asp Tyr Thr Phe Thr>

300          310          320          330
                  *            *            *            *
       ATT TCT TCT CTC CAA CCT GAG GAC ATT GCT ACA TAC TAC TGC CTA CAA
       TAA AGA AGA GAG GTT GGA CTC CTG TAA CGA TGT ATG ATG ACG GAT GTT
       Ile Ser Ser Leu Gln Pro Glu Asp Ile Ala Thr Tyr Tyr Cys Leu Gln>
```

FIG.5A

```
340              350              360              370              380
 *                *                *                *                *
CAT GGT GAG AGT CCG TAT ACA TTT GGA CAA GGA ACA AAA CTA GAG ATC
GTA CCA CTC TCA GGC ATA TGT AAA CCT GTT CCT TGT TTT GAT CTC TAG
His Gly Glu Ser Pro Tyr Thr Phe Gly Gln Gly Thr Lys Leu Glu Ile>

390              400              410              420              430
 *                *                *                *                *
ACA AGA ACT GTT GCG GCG CCG TCT GTC TTC ATC TTC CCG CCA TCT GAT
TGT TCT TGA CAA CGC CGC GGC AGA CAG AAG TAG AAG GGC GGT AGA CTA
Thr Arg Thr Val Ala Ala Pro Ser Val Phe Ile Phe Pro Pro Ser Asp>

440              450              460              470              480
 *                *                *                *                *
GAG CAG TTG AAA TCT GGA ACT GGC TCT GTT GTG TGC CTG CTG AAT AAC
CTC GTC AAC TTT AGA CCT TGA CCG AGA CAA CAC ACG GAC GAC TTA TTG
Glu Gln Leu Lys Ser Gly Thr Ala Ser Val Val Cys Leu Leu Asn Asn>

490              500              510              520              530
 *                *                *                *                *
TTC TAT CCC AGA GAG GCC AAA GTA CAG TGG AAG GTG GAT AAC GCC CTC
AAG ATA GGG TCT CTC CGG TTT CAT GTC ACC TTC CAC CTA TTG CGG GAG
Phe Tyr Pro Arg Glu Ala Lys Val Gln Trp Lys Val Asp Asn Ala Leu>

540              550              560              570
             *                *                *                *
CAA TCG GGT AAC TCC CAG GAG AGT GTC ACA GAG CAG GAC AGC AAG GAC
GTT AGC CCA TTG AGG GTC CTC TCA CAG TGT CTC GTC CTG TCG TTC CTG
Gln Ser Gly Asn Ser Gln Glu Ser Val Thr Glu Gln Asp Ser Lys Asp>

580              590              600              610              620
 *                *                *                *                *
AGC ACC TAC AGC CTC AGC AGC ACC CTG ACG CTG AGC AAA GCA GAC TAC
TCG TGG ATG TCG GAG TCG TCG TGG GAC TGC GAC TCG TTT CGT CTG ATG
Ser Thr Tyr Ser Leu Ser Ser Thr Leu Thr Leu Ser Lys Ala Asp Tyr>

630              640              650              660              670
 *                *                *                *                *
GAG AAA CAC AAA GTC TAC GCC TGC GAA GTC ACC CAT CAG GGC CTG AGC
CTC TTT GTG TTT CAG ATG CGG ACG CTT CAG TGG GTA GTC CCG GAC TCG
Glu Lys His Lys Val Tyr Ala Cys Glu Val Thr His Gln Gly Leu Ser>
```

FIG.5B

```
         680           690           700           710           720
          *             *             *             *             *
TCG CCC GTC ACA AAG AGC TTC AAC AGG GGA GAG TGT T AGA GGG AGA AGT
AGC GGG CAG TGT TTC TCG AAG TTG TCC CCT CTC ACA A TCT CCC TCT TCA
Ser Pro Val Thr Lys Ser Phe Asn Arg Gly Glu Cys >

730           740           750           760           770
          *             *             *             *             *
GCC CCC ACC TGC TCC TCA GTT CCA GCC TGG GGA TCA TAA TCA GCC ATA
CGG GGG TGG ACG AGG AGT CAA GGT CGG ACC CCT AGT ATT AGT CGG TAT 780           790           800           810
          *             *             *             *
CCA CAT TTG TAG AGG TTT TAC TTG CTT TAA AAA ACC TCC CAC ACC TCC
GGT GTA AAC ATC TCC AAA ATG AAC GAA ATT TTT TGG AGG GTG TGG AGG 820           830           840           850           860
 *             *             *             *             *
CCC TGA ACC TGA AAC ATA AAA TGA ATG CAA TTG TTG TTG TTA ACT TGT
GGG ACT TGG ACT TTG TAT TTT ACT TAC GTT AAC AAC AAC AAT TGA ACA 870           880           890           900           910
          *             *             *             *             *
TTA TTG CAG CTT ATA ATG GTT ACA AAT AAA GCA ATA GCA TCA CAA ATT
AAT AAC GTC GAA TAT TAC CAA TGT TTA TTT CGT TAT CGT AGT GTT TAA 920           930           940           950           960
          *             *             *             *             *
TCA CAA ATA AAG CAT TTT TTT CAC TGC ATT CTA GTT GTG GTT TGT CCA
AGT GTT TAT TTC GTA AAA AAA GTG ACG TAA GAT CAA CAC CAA ACA GGT 970           980           990          1000          1010
          *             *             *             *             *
AAC TCA TCA ATG TAT CTT ATC ATG TCT GGA TCC TCT ACG CCG GAC GCA
TTG AGT AGT TAC ATA GAA TAG TAC AGA CCT AGG AGA TGC GGC CTG CGT 1020          1030          1040          1050
          *             *             *             *
TCG TGG CCG GCA TCA CCG GCG CCA CAG GTG CGG TTG CTG GCG CCT ATA
AGC ACC GGC CGT AGT GGC CGC GGT GTC CAC GCC AAC GAC CGC GGA TAT
```

FIG.5C

```
     1060           1070           1080           1090           1100
       *              *              *              *              *
    TCG CCG ACA TCA CCG ATG GGG AAG ATC GGG CTC GCC ACT TCG GGC TCA
    AGC GGC TGT AGT GGC TAC CCC TTC TAG CCC GAG CGG TGA AGC CCG AGT 1110           1120           1130           1140           1150
       *              *              *              *              *
    TGA GCG CTT GTT TCG GCG TGG GTA TGG TGG CAG GCC CGT GGC CGG GGG
    ACT CGC GAA CAA AGC CGC ACC CAT ACC ACC GTC CGG GCA CCG GCC CCC 1160           1170           1180           1190           1200
       *              *              *              *              *
    ACT GTT GGG CGC CAT CTC CTT GCA TGC ACC ATT CCT TGC GGC GGC GGT
    TGA CAA CCC GCG GTA GAG GAA CGT ACG TGG TAA GGA ACG CCG CCG CCA 1210           1220           1230           1240           1250
           *              *              *              *              *
    GCT CAA CGG CCT CAA CCT ACT ACT GGG CTG CTT CCT AAT GCA GGA GTC
    CGA GTT GCC GGA GTT GGA TGA TGA CCC GAC GAA GGA TTA CGT CCT CAG 1260           1270           1280           1290
               *              *              *              *
    GCA TAA GGG AGA GCG TCG ACC TCG GGC CGC GTT GCT GGC GTT TTT CCA
    CGT ATT CCC TCT CGC AGC TGG AGC CCG GCG CAA CGA CCG CAA AAA GGT 1300           1310           1320           1330           1340
      *              *              *              *              *
    TAG GCT CCG CCC CCC TGA CGA GCA TCA CAA AAA TCG ACG CTC AAG TCA
    ATC CGA GGC GGG GGG ACT GCT CGT AGT GTT TTT AGC TGC GAG TTC AGT 1350           1360           1370           1380           1390
         *              *              *              *              *
    GAG GTG GCG AAA CCC GAC AGG ACT ATA AAG ATA CCA GGC GTT TCC CCC
    CTC CAC CGC TTT GGG CTG TCC TGA TAT TTC TAT GGT CCG CAA AGG GGG 1400           1410           1420           1430           1440
         *              *              *              *              *
    TGG AAG CTC CCT CGT GCG CTC TCC TGT TCC GAC CCT GCC GCT TAC CGG
    ACC TTC GAG GGA GCA CGC GAG AGG ACA AGG CTG GGA CGG CGA ATG GCC
```

FIG.5D

```
        1450            1460            1470            1480            1490
          *               *               *               *               *
    ATA CCT GTC CGC CTT TCT CCC TTC GGG AAG CGT GGC GCT TTC TCA ATG
    TAT GGA CAG GCG GAA AGA GGG AAG CCC TTC GCA CCG CGA AAG AGT TAC 1500            1510            1520            1530
          *               *               *               *
    CTC ACG CTG TAG GTA TCT CAG TTC GGT GTA GGT CGT TCG CTC CAA GCT
    GAG TGC GAC ATC CAT AGA GTC AAG CCA CAT CCA GCA AGC GAG GTT CGA 1540            1550            1560            1570            1580
  *               *               *               *               *
    GGG CTG TGT GCA CGA ACC CCC CGT TCA GCC CGA CCG CTG CGC CTT ATC
    CCC GAC ACA CGT GCT TGG GGG GCA AGT CGG GCT GGC GAC GCG GAA TAG 1590            1600            1610            1620            1630
  *               *               *               *               *
    CGG TAA CTA TCG TCT TGA GTC CAA CCC GGT AAG ACA CGA CTT ATC GCC
    GCC ATT GAT AGC AGA ACT CAG GTT GGG CCA TTC TGT GCT GAA TAG CGG 1640            1650            1660            1670            1680
          *               *               *               *               *
    ACT GGC AGC AGC CAC TGG TAA CAG GAT TAG CAG AGC GAG GTA TGT AGG
    TGA CCG TCG TCG GTG ACC ATT GTC CTA ATC GTC TCG CTC CAT ACA TCC 1690            1700            1710            1720            1730
          *               *               *               *               *
    CGG TGC TAC AGA GTT CTT GAA GTG GTG GCC TAA CTA CGG CTA CAC TAG
    GCC ACG ATG TCT CAA GAA CTT CAC CAC CGG ATT GAT GCC GAT GTG ATC 1740            1750            1760            1770
          *               *               *               *
    AAG GAC AGT ATT TGG TAT CTG CGC TCT GCT GAA GCC AGT TAC CTT CGG
    TTC CTG TCA TAA ACC ATA GAC GCG AGA CGA CTT CGG TCA ATG GAA GCC 1780            1790            1800            1810            1820
  *               *               *               *               *
    AAA AAG AGT TGG TAG CTC TTG ATC CGG CAA ACA AAC CAC CGC TGG TAG
    TTT TTC TCA ACC ATC GAG AAC TAG GCC GTT TGT TTG GTG GCG ACC ATC
```

FIG.5E

```
        1830           1840           1850           1860           1870
         *              *              *              *              *
CGG TGG TTT TTT TGT TTG CAA GCA GCA GAT TAC GCG CAG AAA AAA AGG
GCC ACC AAA AAA ACA AAC GTT CGT CGT CTA ATG CGC GTC TTT TTT TCC 1880           1890           1900           1910           1920
         *              *              *              *              *
ATC TCA AGA AGA TCC TTT GAT CTT TTC TAC GGG GTC TGA CGC TCA GTG
TAG AGT TCT TCT AGG AAA CTA GAA AAG ATG CCC CAG ACT GCG AGT CAC 1930           1940           1950           1960           1970
         *              *              *              *              *
GAA CGA AAA CTC ACG TTA AGG GAT TTT GGT CAT GAG ATT ATC AAA AAG
CTT GCT TTT GAG TGC AAT TCC CTA AAA CCA GTA CTC TAA TAG TTT TTC 1980           1990           2000           2010
         *              *              *              *
GAT CTT CAC CTA GAT CCT TTT AAA TTA AAA ATG AAG TTT TAA ATC AAT
CTA GAA GTG GAT CTA GGA AAA TTT AAT TTT TAC TTC AAA ATT TAG TTA 2020           2030           2040           2050           2060
  *              *              *              *              *
CTA AAG TAT ATA TGA GTA AAC TTG GTC TGA CAG TTA CCA ATG CTT AAT
GAT TTC ATA TAT ACT CAT TTG AAC CAG ACT GTC AAT GGT TAC GAA TTA 2070           2080           2090           2100           2110
         *              *              *              *              *
CAG TGA GGC ACC TAT CTC AGC GAT CTG TCT ATT TCG TTC ATC CAT AGT
GTC ACT CCG TGG ATA GAG TCG CTA GAC AGA TAA AGC AAG TAG GTA TCA 2120           2130           2140           2150           2160
         *              *              *              *              *
TGC CTG ACT CCC CGT CGT GTA GAT AAC TAC GAT ACG GGA GGG CTT ACC
ACG GAC TGA GGG GCA GCA CAT CTA TTG ATG CTA TGC CCT CCC GAA TGG 2170           2180           2190           2200           2210
         *              *              *              *              *
ATC TGG CCC CAG TGC TGC AAT GAT ACC GCG AGA CCC ACG CTC ACC GGC
TAG ACC GGG GTC ACG ACG TTA CTA TGG CGC TCT GGG TGC GAG TGG CCG
```

FIG.5F

```
              2220              2230              2240              2250
                *                 *                 *                 *
        TCC AGA TTT ATC AGC AAT AAA CCA GCC AGC CGG AAG GGC CGA GCG CAG
        AGG TCT AAA TAG TCG TTA TTT GGT CGG TCG GCC TTC CCG GCT CGC GTC 2260              2270              2280              2290              2300
      *                 *                 *                 *                 *
    AAG TGG TCC TGC AAC TTT ATC CGC CTC CAT CCA GTC TAT TAA TTG TTG
    TTC ACC AGG ACG TTG AAA TAG GCG GAG GTA GGT CAG ATA ATT AAC AAC 2310              2320              2330              2340              2350
      *                 *                 *                 *                 *
    CCG GGA AGC TAG AGT AAG TAG TTC GCC AGT TAA TAG TTT GCG CAA CGT
    GGC CCT TCG ATC TCA TTC ATC AAG CGG TCA ATT ATC AAA CGC GTT GCA 2360              2370              2380              2390              2400
      *                 *                 *                 *                 *
    TGT TGC CAT TGC TAC AGG CAT CGT GGT GTC ACG CTC GTC GTT TGG TAT
    ACA ACG GTA ACG ATG TCC GTA GCA CCA CAG TGC GAG CAG CAA ACC ATA 2410              2420              2430              2440              2450
      *                 *                 *                 *                 *
    GGC TTC ATT CAG CTC CGG TTC CCA ACG ATC AAG GCG AGT TAC ATG ATC
    CCG AAG TAA GTC GAG GCC AAG GGT TGC TAG TTC CGC TCA ATG TAC TAG 2460              2470              2480              2490
                *                 *                 *                 *
        CCC CAT GTT GTG CAA AAA AGC GGT TAG CTC CTT CGG TCC TCC GAT CGT
        GGG GTA CAA CAC GTT TTT TCG CCA ATC GAG GAA GCC AGG AGG CTA GCA 2500              2510              2520              2530              2540
      *                 *                 *                 *                 *
    TGT CAG AAG TAA GTT GGC CGC AGT GTT ATC ACT CAT GGT TAT GGC AGC
    ACA GTC TTC ATT CAA CCG GCG TCA CAA TAG TGA GTA CCA ATA CCG TCG 2550              2560              2570              2580              2590
      *                 *                 *                 *                 *
    ACT GCA TAA TTC TCT TAC TGT CAT GCC ATC CGT AAG ATG CTT TTC TGT
    TGA CGT ATT AAG AGA ATG ACA GTA CGG TAG GCA TTC TAC GAA AAG ACA
```

FIG.5G

```
              2600           2610           2620           2630           2640
                *              *              *              *              *
          GAC TGG TGA GTA CTC AAC CAA GTC ATT CTG AGA ATA GTG TAT GCG GCG
          CTG ACC ACT CAT GAG TTG GTT CAG TAA GAC TCT TAT CAC ATA CGC CGC 2650           2660           2670           2680           2690
                *              *              *              *              *
          ACC GAG TTG CTC TTG CCC GGC GTC AAC ACG GGA TAA TAC CGC GCC ACA
          TGG CTC AAC GAG AAC GGG CCG CAG TTG TGC CCT ATT ATG GCG CGG TGT 2700           2710           2720           2730
                *              *              *              *
          TAG CAG AAC TTT AAA AGT GCT CAT CAT TGG AAA ACG TTC TTC GGG GCG
          ATC GTC TTG AAA TTT TCA CGA GTA GTA ACC TTT TGC AAG AAG CCC CGC 2740           2750           2760           2770           2780
         *              *              *              *              *
     AAA ACT CTC AAG GAT CTT ACC GCT GTT GAG ATC CAG TTC GAT GTA ACC
     TTT TGA GAG TTC CTA GAA TGG CGA CAA CTC TAG GTC AAG CTA CAT TGG 2790           2800           2810           2820           2830
             *              *              *              *              *
         CAC TCG TGC ACC CAA CTG ATC TTC AGC ATC TTT TAC TTT CAC CAG CGT
         GTG AGC ACG TGG GTT GAC TAG AAG TCG TAG AAA ATG AAA GTG GTC GCA 2840           2850           2860           2870           2880
               *              *              *              *              *
         TTC TGG GTG AGC AAA AAC AGG AAG GCA AAA TGC CGC AAA AAA GGG AAT
         AAG ACC CAC TCG TTT TTG TCC TTC CGT TTT ACG GCG TTT TTT CCC TTA 2890           2900           2910           2920           2930
                  *              *              *              *              *
            AAG GGC GAC ACG GAA ATG TTG AAT ACT CAT ACT CTT CCT TTT TCA ATA
            TTC CCG CTG TGC CTT TAC AAC TTA TGA GTA TGA GAA GGA AAA AGT TAT 2940           2950           2960           2970
                     *              *              *              *
               TTA TTG AAG CAT TTA TCA GGG TTA TTG TCT CAT GAG CGG ATA CAT ATT
               AAT AAC TTC GTA AAT AGT CCC AAT AAC AGA GTA CTC GCC TAT GTA TAA
```

FIG.5H

```
         2980           2990           3000           3010           3020
           *              *              *              *              *
      TGA ATG TAT TTA GAA AAA TAA ACA AAT AGG GGT TCC GCG CAC ATT TCC
      ACT TAC ATA AAT CTT TTT ATT TGT TTA TCC CCA AGG CGC GTG TAA AGG 3030           3040           3050           3060           3070
           *              *              *              *              *
      CCG AAA AGT GCC ACC TGA CGT CTA AGA AAC CAT TAT TAT CAT GAC ATT
      GGC TTT TCA CGG TGG ACT GCA GAT TCT TTG GTA ATA ATA GTA CTG TAA 3080           3090           3100           3110           3120
           *              *              *              *              *
      AAC CTA TAA AAA TAG GCG TAT CAC GAG GCC CTG ATG GCT CTT TGC GGC
      TTG GAT ATT TTT ATC CGC ATA GTG CTC CGG GAC TAC CGA GAA ACG CCG 3130           3140           3150           3160           3170
           *              *              *              *              *
      ACC CAT CGT TCG TAA TGT TCC GTG GCA CCG AGG ACA ACC CTC AAG AGA
      TGG GTA GCA AGC ATT ACA AGG CAC CGT GGC TCC TGT TGG GAG TTC TCT 3180           3190           3200           3210
           *              *              *              *
      AAA TGT AAT CAC ACT GGC TCA CCT TCG GGT GGG CCT TTC TGC GTT TAT
      TTT ACA TTA GTG TGA CCG AGT GGA AGC CCA CCC GGA AAG ACG CAA ATA 3220           3230           3240           3250           3260
      *              *              *              *              *
   AAG GAG ACA CTT TAT GTT TAA GAA GGT TGG TAA ATT CCT TGC GGC TTT
   TTC CTC TGT GAA ATA CAA ATT CTT CCA ACC ATT TAA GGA ACG CCG AAA 3270           3280           3290           3300           3310
           *              *              *              *              *
      GGC AGC CAA GCT AGA GAT CCG GCT GTG AAA TGT GTG TCA GTT AGG GTG
      CCG TCG GTT CGA TCT CTA GGC CGA CAC TTT ACA CAC AGT CAA TCC CAC 3320           3330           3340           3350           3360
           *              *              *              *              *
      TGG AAA GTC CCC AGG CTC CCC AGC AGG CAG AAG TAT GCA AAG CAT GCA
      ACC TTT CAG GGG TCC GAG GGG TCG TCC GTC TTC ATA CGT TTC GTA CGT
```

FIG.51

```
            3370          3380          3390          3400          3410
             *             *             *             *             *
        TCT CAA TTA GTC AGC AAC CAG GCT CCC CAG CAG GCA GAA GTA TGC AAA
        AGA GTT AAT CAG TCG TTG GTC CGA GGG GTC GTC CGT CTT CAT ACG TTT 3420          3430          3440          3450
             *             *             *             *
        GCA TGC ATC TCA ATT AGT CAG CAA CCA TAG TCC CGC CCC TAA CTC CGC
        CGT ACG TAG AGT TAA TCA GTC GTT GGT ATC AGG GCG GGG ATT GAG GCG 3460          3470          3480          3490          3500
       *             *             *             *             *
        CCA TCC CGC CCC TAA CTC CGC CCA GTT CCG CCC ATT CTC CGC CCC ATG
        GGT AGG GCG GGG ATT GAG GCG GGT CAA GGC GGG TAA GAG GCG GGG TAC 3510          3520          3530          3540          3550
             *             *             *             *             *
        GCT GAC TAA TTT TTT TTA TTT ATG CAG AGG CCG AGG CCG CCT CGG CCT
        CGA CTG ATT AAA AAA AAT AAA TAC GTC TCC GGC TCC GGC GGA GCC GGA 3560          3570          3580          3590          3600
             *             *             *             *             *
        CTG AGC TAT TCC AGA AGT AGT GAG GAG GCT TTT TTG GAG GCC TAG GCT
        GAC TCG ATA AGG TCT TCA TCA CTC CTC CGA AAA AAC CTC CGG ATC CGA 3610          3620          3630          3640          3650
             *             *             *             *             *
        TTT GCA AAA AGC TAG CTT GGG GCC ACC GCT CAG AGC ACC TTC CAC CAT
        AAA CGT TTT TCG ATC GAA CCC CGG TGG CGA GTC TCG TGG AAG GTG GTA 3660          3670          3680          3690
             *             *             *             *
        GGC CAC CTC AGC AAG TTC CCA CTT GAA CAA AAA CAT CAA GCA AAT GTA
        CCG GTG GAG TCG TTC AAG GGT GAA CTT GTT TTT GTA GTT CGT TTA CAT 3700          3710          3720          3730          3740
       *             *             *             *             *
        CTT GTG CCT GCC CCA GGG TGA AAA AGT CCA AGC CAT GTA TAT CTG GGT
        GAA CAC GGA CGG GGT CCC ACT TTT TCA GGT TCG GTA CAT ATA GAC CCA
```

FIG.5J

```
        3750          3760          3770          3780          3790
          *             *             *             *             *
     TGA TGG TAC TGG AGA AGG ACT GCG CTG CAA AAC CCG CAC CCT GGA CTG
     ACT ACC ATG ACC TCT TCC TGA CGC GAC GTT TTG GGC GTG GGA CCT GAC 3800          3810          3020          3230          3240
          *             *             *             *             *
     TGA GCC CAA GTG TGT AGA AGA GTT ACC TGA GTG GAA TTT TGA TGG CTC
     ACT CGG GTT CAC ACA TCT TCT CAA TGG ACT CAC CTT AAA ACT ACC GAG 3850          3860          3870          3880          3890
          *             *             *             *             *
     TAG TAC CTT TCA GTC TGA GGG CTC CAA CAG TGA CAT GTA TCT CAG CCC
     ATC ATG GAA AGT CAG ACT CCC GAG GTT GTC ACT GTA CAT AGA GTC GGG 3900          3910          3920          3930
          *             *             *             *
     TGT TGC CAT GTT TCG GGA CCC CTT CCG CAG AGA TCC CAA CAA GCT GGT
     ACA ACG GTA CAA AGC CCT GGG GAA GGC GTC TCT AGG GTT GTT CGA CCA 3940          3950          3960          3970          3980
          *             *             *             *             *
     GTT CTG TGA AGT TTT CAA GTA CAA CCG GAA GCC TGC AGA GAC CAA TTT
     CAA GAC ACT TCA AAA GTT CAT GTT GGC CTT CGG ACG TCT CTG GTT AAA 3990          4000          4010          4020          4030
          *             *             *             *             *
     AAG GCA CTC GTG TAA ACG GAT AAT GGA CAT GGT GAG CAA CCA GCA CCC
     TTC CGT GAG CAC ATT GCC CTA TTA CCT GTA CCA CTC GTT GGT CGT GGG 4040          4050          4060          4070          4080
          *             *             *             *             *
     CTG GTT TGG AAT GGA ACA GGA GTA TAC TCT GAT GGG AAC AGA TGG GCA
     GAC CAA ACC TTA CCT TGT CCT CAT ATG AGA CTA CCC TTG TCT ACC CGT 4090          4100          4110          4120          4130
          *             *             *             *             *
     CCC TTT TGG TTG GCC TTC CAA TGG CTT TCC TGG GCC CCA AGG TCC GTA
     GGG AAA ACC AAC CGG AAG GTT ACC GAA AGG ACC CGG GGT TCC AGG CAT
```

FIG.5K

```
                    4140           4150           4160           4170
                     *              *              *              *
        TTA CTG TGG TGT GGG CGC AGA CAA AGC CTA TGG CAG GGA TAT CGT GGA
        AAT GAC ACC ACA CCC GCG TCT GTT TCG GAT ACC GTC CCT ATA GCA CCT 4180           4190           4200           4210           4220
       *              *              *              *              *
   GGC TCA CTA CCG CGC CTG CTT GTA TGC TGG GGT CAA GAT TAC AGG AAC
   CCG AGT GAT GGC GCG GAC GAA CAT ACG ACC CCA GTT CTA ATG TCC TTG 4230           4240           4250           4260           4270
    *              *              *              *              *
   AAA TGC TGA GGT CAT GCC TGC CCA GTG GGA ACT CCA AAT AGG ACC CTG
   TTT ACG ACT CCA GTA CGG ACG GGT CAC CCT TGA GGT TTA TCC TGG GAC 4280           4290           4300           4310           4320
         *              *              *              *              *
        TGA AGG AAT CCG CAT GGG AGA TCA TCT CTG GGT GGC CCG TTT CAT CTT
        ACT TCC TTA GGC GTA CCC TCT AGT AGA GAC CCA CCG GGC AAA GTA GAA 4330           4340           4350           4360           4370
            *              *              *              *              *
        NCA TCG AGT ATG TGA AGA CTT TGG GGT AAT AGC AAC CTT TGA CCC CAA
        NGT AGC TCA TAC ACT TCT GAA ACC CCA TTA TCG TTG GAA ACT GGG GTT 4380           4390           4400           4410
                     *              *              *              *
        GCC CAT TCC TGG GAA CTG GAA TGG TGC AGG CTG CCA TAC CAA CTT TAG
        CGG GTA AGG ACC CTT GAC CTT ACC ACG TCC GAC GGT ATG GTT GAA ATC 4420           4430           4440           4450           4460
    *              *              *              *              *
   CAC CAA GGC CAT GCG GGA GGA GAA TGG TCT GAA GCA CAT CGA GGA GGC
   GTG GTT CCG GTA CGC CCT CCT CTT ACC AGA CTT CGT GTA GCT CCT CCG 4470           4480           4490           4500           4510
    *              *              *              *              *
   CAT CGA GAA ACT AAG CAA GCG GCA CCG GTA CCA CAT TCG AGC CTA CGA
   GTA GCT CTT TGA TTC GTT CGC CGT GGC CAT GGT GTA AGC TCG ATG CT
```

FIG.5L

```
           4520          4530          4540          4550          4560
            *             *             *             *             *
       TCC CAA GGG GGG CCT GGA CAA TGC CCG TGG TCT GAC TGG GTT CCA CGA
       AGG GTT CCC CCC GGA CCT GTT ACG GGC ACC AGA CTG ACC CAA GGT GCT 4570          4580          4590          4600          4610
            *             *             *             *             *
       AAC GTC CAA CAT CAA CGA CTT TTC TGC TGG TGT CGC CAA TCG CAG TGC
       TTG CAG GTT GTA GTT GCT GAA AAG ACG ACC ACA GCG GTT AGC GTC ACG 4620          4630          4640          4650
            *             *             *             *
       CAG CAT CCG CAT TCC CCG GAC TGT CGG CCA GGA GAA GAA AGG TTA CTT
       GTC GTA GGC GTA AGG GGC CTG ACA GCC GGT CCT CTT CTT TCC AAT GAA 4660          4670          4680          4690          4700
   *             *             *             *             *
  TGA AGA CCG CGG CCC CTC TGC AAT TGA CCC CTT TGC AGT GAC AGA
  ACT TCT GGC GCC GGG GAG ACG GTT AAC ACT GGG GAA ACG TCA CTG TCT 4710          4720          4730          4740          4750
       *             *             *             *             *
  AGC CAT CGT CCG CAC ATG CCT TCT CAA TGA GAC TGG CCA CGA GCC CTT
  TCG GTA GCA GGC GTG TAC GGA AGA GTT ACT CTG ACC GGT GCT CGG CAA 4760          4770          4780          4790          4800
           *             *             *             *             *
      CCA ATA CAA AAA CTA ATT AGA CTT TGA GTG ATC TTG AGC CTT TCC TAG
      GGT TAT GTT TTT GAT TAA TCT GAA ACT CAC TAG AAC TCG GAA AGG ATC 4810          4820          4830          4840          4850
           *             *             *             *             *
      TTC ATC CCA CCC CGC CCC AGA GAG ATC TTT GTG AAG GAA CCT TAC TTC
      AAG TAG GGT GGG GCG GGG TCT CTC TAG AAA CAC TTC CTT GGA ATG AAG 4860          4870          4880          4890
           *             *             *             *
      TGT GGT GTG ACA TAA TTG GAC AAA CTA CCT ACA GAG ATT TAA AGC TCT
      ACA CCA CAC TGT ATT AAC CTG TTT GAT GGA TGT CTC TAA ATT TCG AGA
```

FIG.5M

```
       4900           4910           4920           4930           4940
         *              *              *              *              *
  AAG GTA AAT ATA AAA TTT TTA AGT GTA TAA TGT GTT AAA CTA CTG ATT
  TTC CAT TTA TAT TTT AAA AAT TCA CAT ATT ACA CAA TTT GAT GAC TAA 4950           4960           4970           4980           4990
         *              *              *              *              *
  CTA ATT GTT TGT GTA TTT TAG ATT CCA ACC TAT GGA ACT GAT GAA TGG
  GAT TAA CAA ACA CAT AAA ATC TAA GGT TGG ATA CCT TGA CTA CTT ACC 5000           5010           5020           5030           5040
         *              *              *              *              *
  GAG CAG TGG TGG AAT GCC TTT AAT GAG GAA AAC CTG TTT TGC TCA GAA
  CTC GTC ACC ACC TTA CGG AAA TTA CTC CTT TTG GAC AAA ACG AGT CTT 5050           5060           5070           5080           5090
         *              *              *              *              *
  GAA ATC CCA TCT AGT GAT GAT GAG GCT ACT GCT GAC TCT CAA CAT TCT
  CTT TAC GGT AGA TCA CTA CTA CTC CGA TGA CGA CTG AGA GTT GTA AGA 5100           5110           5120           5130
         *              *              *              *
  ACT CCT CCA AAA AAG AAG AGA AAG GTA GAA GAC CCC AAG GAC TTT CCT
  TGA GGA GGT TTT TTC TTC TCT TTC CAT CTT CTG GGG TTC CTG AAA GGA 5140           5150           5160           5170           5180
   *              *              *              *              *
  TCA GAA TTG CTA AGT TTT TTG AGT CAT GCT GTG TTT AGT AAT AGA ACT
  AGT CTT AAC GAT TCA AAA AAC TCA GTA CGA CAC AAA TCA TTA TCT TGA 5190           5200           5210           5220           5230
         *              *              *              *              *
  CTT GCT TGC TTT GCT ATT TAC ACC ACA AAG GAA AAA GCT GCA CTG CTA
  CAA CGA ACG AAA CGA TAA ATG TGG TGT TTC CTT TTT CGA CGT GAC GAT 5240           5250           5260           5270           5280
         *              *              *              *              *
  TAC AAG AAA ATT ATG GAA AAA TAT TCT GTA ACC TTT ATA AGT AGG CAT
  ATG TTC TTT TAA TAC CTT TTT ATA AGA CAT TGG AAA TAT TCA TCC GTA
```

FIG.5N

```
              5290          5300          5310          5320          5330
               *             *             *             *             *
          AAC AGT TAT AAT CAT AAC ATA CTG TTT TTT CTT ACT CCA CAC AGG CAT
          TTG TCA ATA TTA GTA TTG TAT GAC AAA AAA GAA TGA GGT GTG TCC GTA 5340          5350          5360          5370
                    *             *             *             *
          AGA GTG TCT GCT ATT AAT AAC TAT GCT CAA AAA TTG TGT ACC TTT AGC
          TCT CAC AGA CGA TAA TTA TTG ATA CGA GTT TTT AAC ACA TGG AAA TCG 5380          5390          5400          5410          5420
      *             *             *             *             *
     TTT TTA ATT TGT AAA GGG GTT AAT AAG GAA TAT TTG ATG TAT AGT GCC
     AAA AAT TAA ACA TTT CCC CAA TTA TTC CTT ATA AAC TAC ATA TCA CGG 5430          5440          5450          5460          5470
           *             *             *             *             *
          TTG ACT AGA GAT CAT AAT CAG CCA TAC CAC ATT TGT AGA GGT TTT ACT
          AAC TGA TCT CTA GTA TTA GTC GGT ATG GTG TAA ACA TCT CCA AAA TGA 5480          5490          5500          5510          5520
               *             *             *             *             *
          TGC TTT AAA AAA CCT CCC ACA CCT CCC CCT GAA CCT GAA ACA TAA AAT
          ACG AAA TTT TTT GGA GGG TGT GGA GGG GGA CTT GGA CTT TGT ATT TTA 5530          5540          5550          5560          5570
                   *             *             *             *             *
          GAA TGC AAT TGT TGT TGT TAA CTT GTT TAT TGC AGC TTA TAA TGG TTA
          CTT ACG TTA ACA ACA ACA ATT GAA CAA ATA ACG TCG AAT ATT ACC AAT 5580          5590          5600          5610
                        *             *             *             *
          CAA ATA AAG CAA TAG CAT CAC AAA TTT CAC AAA TAA AGC ATT TTT TTC
          GTT TAT TTC GTT ATC GTA GTG TTT AAA GTG TTT ATT TCG TAA AAA AAG 5620          5630          5640          5650          5660
      *             *             *             *             *
     ACT GCA TTC TAG TTG TGG TTT GTC CAA ACT CAT CAA TGT ATC TTA TCA
     TGA CGT AAG ATC AAC ACC AAA CAG GTT TGA GTA GTT ACA TAG AAT AGT
```

FIG.50

```
      5670                5680                5690                5700                5710
        *                   *                   *                   *                   *
TGT CTG GAT CTC TAG CTT CGT GTC AAG GAC GGT GAC TGC AGT GAA TAA
ACA GAC CTA GAG ATC GAA GCA CAG TTC CTG CCA CTG ACG TCA CTT ATT 5720                5730                5740                5750                5760
        *                   *                   *                   *                   *
TAA AAT GTG TGT TTG TCC GAA ATA CGC GTT TTG AGA TTT CTG TCG CCG
ATT TTA CAC ACA AAC AGG CTT TAT GCG CAA AAC TCT AAA GAC AGC GGC 5770                5780                5790                5800                5810
        *                   *                   *                   *                   *
ACT AAA TTC ATG TCG CGC GAT AGT GGT GTT TAT CGC CGA TAG AGA TGG
TGA TTT AAG TAC AGC GCG CTA TCA CCA CAA ATA GCG GCT ATC TCT ACC 5820                5830                5840                5850
             *                   *                   *                   *
CGA TAT TGG AAA AAT CGA TAT TTG AAA ATA TGG CAT ATT GAA AAT GTC
GCT ATA ACC TTT TTA GCT ATA AAC TTT TAT ACC GTA TAA CTT TTA CAG 5860                5870                5880                5890                5900
   *                   *                   *                   *                   *
GCC GAT GTG AGT TTC TGT GTA ACT GAT ATC GCC ATT TTT CCA AAA GTG
CGG CTA CAC TCA AAG ACA CAT TGA CTA TAG CGG TAA AAA GGT TTT CAC 5910                5920                5930                5940                5950
   *                   *                   *                   *                   *
ATT TTT GGG CAT ACG CGA TAT CTG GCG ATA GCG CTT ATA TCG TTT ACG
TAA AAA CCC GTA TGC GCT ATA GAC CGC TAT CGC GAA TAT AGC AAA TGC 5960                5970                5980                5990                6000
        *                   *                   *                   *                   *
GGG GAT GGC GAT AGA CGA CTT TGG TGA CTT GGG CGA TTC TGT GTG TCG
CCC CTA CCG CTA TCT GCT GAA ACC ACT GAA CCC GCT AAG ACA CAC AGC 6010                6020                6030                6040                6050
        *                   *                   *                   *                   *
CAA ATA TCG CAG TTT CGA TAT AGG TGA CAG ACG ATA TGA GGC TAT ATC
GTT TAT AGC GTC AAA GCT ATA TCC ACT GTC TGC TAT ACT CCG ATA TAG
```

FIG.5P

```
      6060             6070            6080            6090
       *                *               *               *
 GCC CAT AGA GGC GAC ATC AAG CTG GCA CAT GGC CAA TGC ATA TCG ATC
 CGG GTA TCT CCG CTG TAG TTC GAC CGT GTA CCG GTT ACG TAT AGC TAG 6100            6110            6120            6130            6140
  *               *               *               *               *
 TAT ACA TTG AAT CAA TAT TGG CCA TTA GCC ATA TTA TTC ATT GGT TAT
 ATA TGT AAC TTA GTT ATA ACC GGT AAT CGG TAT AAT AAG TAA CCA ATA 6150            6160            6170            6180            6190
        *               *               *               *               *
 ATA GCA TAA ATC AAT ATT GGC TAT TGG CCA TTG CAT ACG TTG TAT CCA
 TAT CGT ATT TAG TTA TAA CCG ATA ACC GGT AAC GTA TGC AAC ATA GGT 6200            6210            6220            6230            6240
         *               *               *               *               *
 TAT CAT AAT ATG TAC ATT TAT ATT GGC TCA TGT CCA ACA TTA CCG CCA
 ATA GTA TTA TAC ATG TAA ATA TAA CCG AGT ACA GGT TGT AAT GGC GGT 6250            6260            6270            6280            6290
         *               *               *               *               *
 TGT TGA CAT TGA TTA TTG ACT AGT TAT TAA TAG TAA TCA ATT ACG GGG
 ACA ACT GTA ACT AAT AAC TGA TCA ATA ATT ATC ATT AGT TAA TGC CCC 6300            6310            6320            6330
             *               *               *               *
 TCA TTA GTT CAT AGC CCA TAT ATG GAC TTC CGC GTT ACA TAA CTT ACG
 AGT AAT CAA GTA TCG GGT ATA TAC CTC AAG GCG CAA TGT ATT GAA TGC 6340            6350            6360            6370            6380
  *               *               *               *               *
 GTA AAT GGC CCG CCT GGC TGA CCG CCC AAC GAC CCC CGC CCA TTG ACG
 CAT TTA CCG GGC GGA CCG ACT GGC GGG TTG CTG GGG GCG GGT AAC TGC 6390            6400            6410            6420            6430
  *               *               *               *               *
 TCA ATA ATG ACG TAT GTT CCC ATA GTA ACG CCA ATA GGG ACT TTC CAT
 AGT TAT TAC TGC ATA CAA GGG TAT CAT TGC GGT TAT CCC TGA AAG GTA
```

FIG.5Q

```
        6440            6450            6460            6470            6480
          *               *               *               *               *
TGA CGT CAA TGG GTG GAG TAT TTA CGG TAA ACT GCC CAC TTG GCA GTA
ACT GCA GTT ACC CAC CTC ATA AAT GCC ATT TGA CGG GTG AAC CGT CAT 6490            6500            6510            6520            6530
          *               *               *               *               *
CAT CAA GTG TAT CAT ATG CCA AGT ACG CCC CCT ATT GAC GTC AAT GAC
GTA GTT CAC ATA GTA TAC GGT TCA TGC GGG GGA TAA CTG CAG TTA CTG 6540            6550            6560            6570
          *               *               *               *
GGT AAA TGG CCC GCC TGG CAT TAT GCG CAG TAC ATG ACC TTA TGG GAC
CCA TTT ACC GGG CGG ACC GTA ATA CGC GTC ATG TAC TGG AAT ACC CTG 6580            6590            6600            6610            6620
    *               *               *               *               *
TTT CCT ACT TGG CAG TAC ATC TAC GTA TTA GTC ATC GCT ATT ACC ATG
AAA GGA TGA ACC GTC ATG TAG ATG CAT AAT CAG TAG CGA TAA TGG TAC 6630            6640            6650            6660            6670
          *               *               *               *               *
GTG ATG CGG TTT TGG CAG TAC ATC AAT GGG CGT GGA TAG CGG TTT GAC
CAC TAC GCC AAA ACC GTC ATG TAG TTA CCC GCA CCT ATC GCG AAA CTG 6680            6690            6700            6710            6720
          *               *               *               *               *
TCA CGG GGA TTT CCA AGT CTC CAC CCC ATT GAC GTC AAT GGG AGT TTG
AGT GCC CCT AAA GGT TCA GAG GTG GGG TAA CTG CAG TTA CCC TCA AAC 6730            6740            6750            6760            6770
          *               *               *               *               *
TTT TGG CAC CAA AAT CAA CGG GAC TTT CCA AAA TGT CGT AAC AAC TCC
AAA ACC GTG GTT TTA GTT GCC CTG AAA GGT TTT ACA GCA TTG TTG AGG 6780            6790            6800            6810
          *               *               *               *
GCC CCA TTG ACG CAA ATG GGC GGT AGG CGT GTA CGG TGG GAG GTC TAT
CGG GGT AAC TGC GTT TAC CCG CCA TCC GCA CAT GCC ACC CTC CAG ATA
```

FIG.5R

```
      6820            6830            6840            6850            6860
        *               *               *               *               *
ATA AGC AGA GCT CGT TTA GTG AAC CGT CAG ATC GCC TGG AGA CGC CAT
TAT TCG TCT CGA GCA AAT CAC TTG GCA GTC TAG CGG ACC TCT GCG GTA 6870            6880            6890            6900            6910
        *               *               *               *               *
CCA CGC TGT TTT GAC CTC CAT AGA AGA CAC CGG GAC CGA TCC AGC CTC
GGT GCG ACA AAA CTG GAG GTA TCT TCT GTG GCC CTG GCT AGG TCG GAG 6920            6930            6940            6950            6960
        *               *               *               *               *
CGC GGC CGG GAA CGG TGC ATT GGA ACG CGG ATT CCC CGT GCC AAG AGT
GCG CCG GCC CTT GCC ACG TAA CCT TGC GCC TAA GGG GCA CGG TTC TCA 6970            6980            6990            7000            7010
        *               *               *               *               *
GAC GTA AGT ACC GCC TAT AGA GTC TAT AGG CCC ACC CCC TTG GCT TCT
CTG CAT TCA TGG CGG ATA TCT CAG ATA TCC GGG TGG GGG AAC CGA AGA 7020            7030            7040            7050
        *               *               *               *
TAT GCA TGC TAT ACT GTT TTT GGC TTG GGT CTA TAC ACC CCG CTT C
ATA CGT ACG ATA TGA CAA AAA CCG AAC CCA GAT ATG TGG GGC GAA G 7060            7070            7080            7090            7100
  *               *               *               *               *
CTC ATG TTA TAG GTG ATG GTA TAG CTT AGC CTA TAG GTG TGG GTT ATT
GAG TAC AAT ATC CAC TAC CAT ATC GAA TCG GAT ATC CAC ACC CAA TAA 7110            7120            7130            7140            7150
        *               *               *               *               *
GAC CAT TAT TGA CCA CTC CCC TAT TGG TGA CGA TAC TTT CCA TTA CTA
CTG GTA ATA ACT GGT GAG GGG ATA ACC ACT GCT ATG AAA GGT AAT GAT 7160            7170            7180            7190            7200
        *               *               *               *               *
ATC CAT AAC ATG GCT CTT TGC CAC AAC TCT CTT TAT TGG CTA TAT GCC
TAG GTA TTG TAC CGA GAA ACG GTG TTG AGA GAA ATA ACC GAT ATA CGG
```

FIG.5S

```
        7210            7220            7230            7240            7250
         *               *               *               *               *
AAT ACA CTG TCC TTC AGA GAC TGA CAC GGA CTC TGT ATT TTT ACA GGA
TTA TGT GAC AGG AAG TCT CTG ACT GTG CCT GAG ACA TAA AAA TGT CCT 7260            7270            7280            7290
             *               *               *               *
TGG GGT CTC ATT TAT TAT TTA CAA ATT CAC ATA TAC AAC ACC ACC GTC
ACC CCA GAG TAA ATA ATA AAT GTT TAA GTG TAT ATG TTG TGG TGG CAG 7300            7310            7320            7330            7340
   *               *               *               *               *
CCC AGT GCC CGC AGT TTT TAT TAA ACA TAA CGT GGG ATC TCC ACG CGA
GGG TCA CGG GCG TCA AAA ATA ATT TGT ATT GCA CCC TAG AGG TGC GCT 7350            7360            7370            7380            7390
     *               *               *               *               *
ATC TCG GGT ACG TGT TCC GGA CAT GGG CTC TTC TCC GGT AGC GGC GGA
TAG AGC CCA TGC ACA AGG CCT GTA CCC GAG AAG AGG CCA TCG CCG CCT 7400            7410            7420            7430            7440
         *               *               *               *               *
GCT TCT ACA TCC GAG CCC TGC TCC CAT GCC TCC AGC GAC TCA TGG TCG
CGA AGA TGT AGG CTC GGG ACG AGG GTA CGG AGG TCG CTG AGT ACC AGC 7450            7460            7470            7480            7490
             *               *               *               *               *
CTC GGC AGC TCC TTG CTC CTA ACA GTG GAG GCC AGA CTT AGG CAC AGC
GAG CCG TCG AGG AAC GAG GAT TGT CAC CTC CGG TCT GAA TCC GTG TCG 7500            7510            7520            7530
                 *               *               *               *
ACG ATG CCC ACC ACC ACC AGT GTG CCG CAC AAG GCC GTG GCG GTA GGG
TGC TAC GGG TGG TGG TGG TCA CAC GGC GTG TTC GGG CAC CGC CAT CCC 7540            7550            7560            7570            7580
   *               *               *               *               *
TAT GTG TCT GAA AAT GAG CTC GGG GAG CGG GCT TGC ACC GCT GAC GCA
ATA CAC AGA CTT TTA CTC GAG CCC CTC GCC CGA ACG TGG CGA CTG CGT
```

FIG.5T

```
       7590           7600           7610           7620           7630
         *              *              *              *              *
TTT GGA AGA CTT AAG GCA GCG GCA GAA GAA GAT GCA GGC AGC TGA GTT
AAA CCT TCT GAA TTC CGT CGC CGT CTT CTT CTA CGT CCG TCG ACT CAA 7640           7650           7660           7670           7680
         *              *              *              *              *
GTT GTG TTC TGA TAA GAG TCA GAG GTA ACT CCC GTT GCG GTG CTG TTA
CAA CAC AAG ACT ATT CTC AGT CTC CAT TGA GGG CAA CGC CAC GAC AAT 7690           7700           7710           7720           7730
         *              *              *              *              *
ACG GTG GAG GGC AGT GTA GTC TGA GCA GTA CTC GTT GCT GCC GCG CGC
TGC CAC CTC CCG TCA CAT CAG ACT CGT CAT GAG CAA CGA CGG CGC GCG 7740           7750           7760           7770
              *              *              *              *
GCC ACC AGA CAT AAT AGC TGA CAG ACT AAC AGA CTG TTC CTT TCC ATG
CGG TGG TCT GTA TTA TCG ACT GTC TGA TTG TCT GAC AAG GAA AGG TAC 7780           7790           7800           7810           7820
    *              *              *              *              *
GGT CTT TTC TGC AGT CAC CGT CCT TGA CAC GAA GCT TGG GCT GCA GGT
CCA GAA AAG ACG TCA GTG GCA GGA ACT GTG CTT CGA ACC CGA CGT CCA 7830           7840           7850           7860
         *              *              *              *
CGA TCG ACT CTA GAG GAT CGA TCC CCG GGC GAG CTC G
GCT AGC TGA GAT CTC CTA GCT AGG GGC CCG CTC GAG C
```

FIG.5U

SEQUENCE LISTING

```
<160> NUMBER OF SEQ ID NOS: 22

<210> SEQ ID NO 1
<211> LENGTH: 1489
<212> TYPE: DNA
<213> ORGANISM: Mus musculus

<400> SEQUENCE: 1
ggtccttaca atgaaatgca gctgggtcat cttcttcctg atggcagtgg ttacaggggt      60
caattcagag attcagctgc agcagtctgg ggctgagctt gtgaggccag gggccttagt     120
caagttgtcc tgcaaagctt ctggcttcaa cattaaagac tactatatgc actgggtgaa     180
gcagaggcct gaacagggcc tggagtggat tggattgatt gatcctgaga atggtaatac     240
tatatatgac ccgaagttcc agggcaaggc cagtataaca gcagacacat cctccaacac     300
agcctacctg cagctcagca gcctgacatc tgaggacact gccgtctatt actgtgctag     360
agataactcg tactactttg actactgggg ccaaggcacc actctcacag tctcctcagc     420
caaaacgaca cccccatctg tctatccact ggcccctgga tctgctgccc aaactaactc     480
catggtgacc ctgggatgcc tggtcaaggg ctatttccct gagccagtga cagtgacctg     540
gaactctgga tccctgtcca gcggtgtgca caccttccca gctgtcctgc agtctgacct     600
ctacactctg agcagctcag tgactgtgcc ctccagcacc tggcccagcg agaccgtcac     660
ctgcaacgtt gcccacccgg ccagcagcac caaggtggac aagaaaattg tgcccaggga     720
ttgtggttgt aagccttgca tatgtacagt cccagaagta tcatctgtct tcatcttccc     780
cccaaagccc aaggatgtgc tcaccattac tctgactcct aaggtcacgt gtgttgtggt     840
agacatcagc aaggatgatc ccgaggtcca gttcagctgg tttgtagatg atgtggaggt     900
gcacacagct cagacgcaac cccgggagga gcagttcaac agcactttcc gctcagtcag     960
tgaacttccc atcatgcacc aggactggct caatggcaag gagttcaaat gcagggtcaa    1020
cagtgcagct ttccctgccc ccatcgagaa aaccatctcc aaaaccaaag gcagaccgaa    1080
ggctccacag gtgtacacca ttccacctcc caaggagcag atggccaagg ataaagtcag    1140
tctgaactgc atgataacag acttcttccc tgaagacatt actgtggagt ggcagtggaa    1200
tgggcagcca gcggagaact acaagaacac tcagcccatc atggacacag atggctctta    1260
cttcgtctac agcaagctca atgtgcagaa gagcaactgg gaggcaggaa atactttcac    1320
ctgctctgtg ttacatgagg gcctgcacaa ccaccatact gagaagagcc tctcccactc    1380
tcctggtaaa tgatcccagt gtccttggag ccctctggtc ctacaggact ctgacaccta    1440
cctccacccc tccctgtata aataaagcac ccagcactgc cttggaccc                 1489
```

<210> SEQ ID NO 2
<211> LENGTH: 460
<212> TYPE: PRT
<213> ORGANISM: Mus musculus

<400> SEQUENCE: 2

```
Met Lys Cys Ser Trp Val Ile Phe Phe Leu Met Ala Val Val Thr Gly
  1               5                  10                  15

Val Asn Ser Glu Ile Gln Leu Gln Gln Ser Gly Ala Glu Leu Val Arg
             20                  25                  30

Pro Gly Ala Leu Val Lys Leu Ser Cys Lys Ala Ser Gly Phe Asn Ile
         35                  40                  45

Lys Asp Tyr Tyr Met His Trp Val Lys Gln Arg Pro Glu Gln Gly Leu
     50                  55                  60

Glu Trp Ile Gly Leu Ile Asp Pro Glu Asn Gly Asn Thr Ile Tyr Asp
 65                  70                  75                  80

Pro Lys Phe Gln Gly Lys Ala Ser Ile Thr Ala Asp Thr Ser Ser Asn
                 85                  90                  95

Thr Ala Tyr Leu Gln Leu Ser Ser Leu Thr Ser Glu Asp Thr Ala Val
            100                 105                 110

Tyr Tyr Cys Ala Arg Asp Asn Ser Tyr Tyr Phe Asp Tyr Trp Gly Gln
        115                 120                 125

Gly Thr Thr Leu Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Asn Cys Met Ile Thr Asp
    370                 375                 380
```

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
            405                 410                 415

Tyr Phe Val Tyr Ser Lys Leu Asn Val Gln Lys Ser Asn Trp Glu Ala
        420                 425                 430

Gly Asn Thr Phe Thr Cys Ser Val Leu His Glu Gly Leu His Asn His
            435                 440                 445

His Thr Glu Lys Ser Leu Ser His Ser Pro Gly Lys
    450                 455                 460

<210> SEQ ID NO 3
<211> LENGTH: 937
<212> TYPE: DNA
<213> ORGANISM: Mus musculus

<400> SEQUENCE: 3
ggacatgcgg gccctgctc agttttttgg gatcttgttg ctctggtttc caggtatcag        60
atgtgacatc aagatgaccc agtctccatc ctccatgtat gcatcgctgg gagagagagt       120
cactatcact tgtaaggcga gtcaggacat agaaagtat ttaaactggt accagcagaa        180
accatggaaa tctcctaaga ccctgatcta ttatgcaaca agcttggcag atggggtccc       240
atcaagattc agtggcagtg gatctgggca agattattct ctaaccatca gcagtctgga       300
gtctgacgat acagcaactt attactgtct acaacatggt gagagcccgt acacgttcgg       360
aggggggacc aagctggaaa taaacagggc tgatgctgca ccaactgtat ccatcttccc       420
accatccagt gagcagttaa catctggagg tgcctcagtc gtgtgcttct tgaacaactt       480
ctaccccaaa gacatcaatg tcaagtggaa gattgatggc agtgaacgac aaaatggcgt       540
cctgaacagt tggactgatc aggacagcaa agacagcacc tacagcatga gcagcaccct       600
cacgttgacc aaggacgagt atgaacgaca taacagctat acctgtgagg ccactcacaa       660
gacatcaact tcacccattg tcaagagctt caacaggaat gagtgttaga gacaaaggtc       720
ctgagacgcc accaccagct ccccagctcc atcctatctt cccttctaag gtcttggagg       780
cttccccaca gcgaccgac cactgttgcg gtgctccaaa cctcctcccc acctccttct        840
cctcctcctc ccttccttg gcttttatca tgctaatatt tgcagaaaat attcaataaa        900
gtgagtcttt gcacttgaaa aaaaaaaaa aaaaaaa                                 937

<210> SEQ ID NO 4
<211> LENGTH: 234
<212> TYPE: PRT
<213> ORGANISM: Mus musculus

<400> SEQUENCE: 4

Met Arg Ala Pro Ala Gln Phe Phe Gly Ile Leu Leu Leu Trp Phe Pro
1               5                   10                  15

Gly Ile Arg Cys Asp Ile Lys Met Thr Gln Ser Pro Ser Ser Met Tyr
            20                  25                  30

Ala Ser Leu Gly Glu Arg Val Thr Ile Thr Cys Lys Ala Ser Gln Asp
        35                  40                  45

Ile Arg Lys Tyr Leu Asn Trp Tyr Gln Gln Lys Pro Trp Lys Ser Pro
    50                  55                  60

Lys Thr Leu Ile Tyr Tyr Ala Thr Ser Leu Ala Asp Gly Val Pro Ser
65                  70                  75                  80

```
Arg Phe Ser Gly Ser Gly Ser Gly Gln Asp Tyr Ser Leu Thr Ile Ser
                85                  90                  95

Ser Leu Glu Ser Asp Asp Thr Ala Thr Tyr Tyr Cys Leu Gln His Gly
            100                 105                 110

Glu Ser Pro Tyr Thr Phe Gly Gly Gly Thr Lys Leu Glu Ile Asn Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 5
<211> LENGTH: 5
<212> TYPE: PRT
<213> ORGANISM: Mus musculus

<400> SEQUENCE: 5

Asp Tyr Tyr Met His
1               5

<210> SEQ ID NO 6
<211> LENGTH: 17
<212> TYPE: PRT
<213> ORGANISM: Mus musculus

<400> SEQUENCE: 6

Leu Ile Asp Pro Glu Asn Gly Asn Thr Ile Tyr Asp Pro Lys Phe Gln
1               5                   10                  15

Gly

<210> SEQ ID NO 7
<211> LENGTH: 8
<212> TYPE: PRT
<213> ORGANISM: Mus musculus

<400> SEQUENCE: 7

Asp Asn Ser Tyr Tyr Phe Asp Tyr
1               5

<210> SEQ ID NO 8
<211> LENGTH: 11
<212> TYPE: PRT
<213> ORGANISM: Mus musculus

<400> SEQUENCE: 8

Lys Ala Ser Gln Asp Ile Arg Lys Tyr Leu Asn
1               5                   10

<210> SEQ ID NO 9
<211> LENGTH: 7
```

```
<212> TYPE: PRT
<213> ORGANISM: Mus musculus

<400> SEQUENCE: 9

Tyr Ala Thr Ser Leu Ala Asp
  1               5

<210> SEQ ID NO 10
<211> LENGTH: 9
<212> TYPE: PRT
<213> ORGANISM: Mus musculus

<400> SEQUENCE: 10

Leu Gln His Gly Glu Ser Pro Tyr Thr
  1               5

<210> SEQ ID NO 11
<211> LENGTH: 117
<212> TYPE: PRT
<213> ORGANISM: Artificial Sequence
<220> FEATURE:
<223> OTHER INFORMATION: Whereby sequence is a combination of mouse and
      human.

<400> SEQUENCE: 11

Gln Val Gln Leu Val Gln Ser Gly Gly Gly Val Val Gln Pro Gly Arg
  1               5                  10                  15

Leu Leu Arg Leu Ser Cys Lys Ala Ser Gly Phe Asn Ile Lys Asp Tyr
             20                  25                  30

Tyr Met His Trp Val Arg Gln Ala Pro Gly Lys Gly Leu Glu Trp Ile
         35                  40                  45

Gly Leu Ile Asp Pro Glu Asn Gly Asn Thr Ile Tyr Asp Pro Lys Phe
     50                  55                  60

Gln Gly Arg Phe Ser Ile Ser Ala Asp Thr Ser Lys Asn Thr Ala Phe
 65                  70                  75                  80

Leu Gln Met Asp Ser Leu Arg Pro Glu Asp Thr Ala Val Tyr Tyr Cys
                 85                  90                  95

Ala Arg Asp Asn Ser Tyr Tyr Phe Asp Tyr Trp Gly Gln Gly Thr Pro
            100                 105                 110

Val Thr Val Ser Ser
        115

<210> SEQ ID NO 12
<211> LENGTH: 108
<212> TYPE: PRT
<213> ORGANISM: Artificial Sequence
<220> FEATURE:
<223> OTHER INFORMATION: Whereby sequence is a combination of mouse and
      human.

<400> SEQUENCE: 12

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Ile Arg Lys Tyr
             20                  25                  30

Leu Asn Trp Tyr Gln Gln Lys Trp Lys Ala Pro Lys Thr Leu Ile
         35                  40                  45

Tyr Tyr Ala Thr Ser Leu Ala Asp Gly Val Pro Ser Arg Phe Ser Gly
     50                  55                  60

Ser Gly Ser Gly Thr Asp Tyr Thr Phe Thr Ile Ser Ser Leu Gln Pro
 65                  70                  75                  80
```

```
Glu Asp Ile Ala Thr Tyr Tyr Cys Leu Gln His Gly Glu Ser Pro Tyr
            85                  90                  95

Thr Phe Gly Gln Gly Thr Lys Leu Glu Ile Thr Arg
        100                 105

<210> SEQ ID NO 13
<211> LENGTH: 117
<212> TYPE: PRT
<213> ORGANISM: Artificial Sequence
<220> FEATURE:
<223> OTHER INFORMATION: Whereby sequence is a combination of mouse and
      human.

<400> SEQUENCE: 13

Gln Val Gln Leu Val Glu Ser Gly Gly Gly Val Val Gln Pro Gly Arg
 1               5                  10                  15

Ser Leu Arg Leu Ser Cys Lys Ala Ser Gly Phe Asn Ile Lys Asp Tyr
            20                  25                  30

Tyr Met His Trp Val Arg Gln Ala Pro Gly Lys Gly Leu Glu Trp Ile
        35                  40                  45

Gly Leu Ile Asp Pro Glu Asn Gly Asn Thr Ile Tyr Asp Pro Lys Phe
50                  55                  60

Gln Gly Arg Phe Thr Ile Ser Ala Asp Asn Ser Lys Asn Thr Leu Phe
65                  70                  75                  80

Leu Gln Met Asp Ser Leu Arg Pro Glu Asp Thr Ala Val Tyr Tyr Cys
                85                  90                  95

Ala Arg Asp Asn Ser Tyr Tyr Phe Asp Tyr Trp Gly Gln Gly Thr Pro
            100                 105                 110

Val Thr Val Ser Ser
        115

<210> SEQ ID NO 14
<211> LENGTH: 108
<212> TYPE: PRT
<213> ORGANISM: Artificial Sequence
<220> FEATURE:
<223> OTHER INFORMATION: Whereby sequence is a combination of mouse and
      human.

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Arg Lys Tyr
            20                  25                  30

Leu Asn Trp Tyr Gln Gln Lys Pro Gly Lys Ala Pro Lys Leu Leu Ile
        35                  40                  45

Tyr Tyr Ala Thr Ser Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln His Gly Glu Ser Pro Tyr
                85                  90                  95

Thr Phe Gly Gln Gly Thr Lys Leu Glu Ile Thr Arg
            100                 105

<210> SEQ ID NO 15
<211> LENGTH: 7073
<212> TYPE: DNA
<213> ORGANISM: Artificial Sequence
```

<220> FEATURE:
<223> OTHER INFORMATION: Whereby sequence is a combination of mouse and human.

<400> SEQUENCE: 15

```
gaattcgcct ccaccatgga atggagctgg gtctttctct tcttcttgtc agtaactaca        60
ggtgtacact cacaagttca gctggtggag tctggaggag gagtagtaca acctggaagg       120
tcactgagac tgtcttgtaa ggctagtgga ttcaatatca aggactatta tatgcactgg       180
gtcagacaag ctcctgggaa aggactcgag tggataggtt taattgatcc tgagaatggt       240
aacacgatat atgatcccaa gttccaagga agattcacaa tttctgcaga caactctaag       300
aatacactgt tcctgcagat ggactcactc agacctgagg atacagcagt ctactattgt       360
gctagagata acagttatta cttcgactac tggggccaag gaacaccagt caccgtgagc       420
tcagcttcca caagggccc atccgtcttc ccctggcgc cctgctccag gagcacctcc         480
gagagcacag ccgccctggg ctgcctggtc aaggactact ccccgaacc ggtgacggtg        540
tcgtggaact caggcgccct gaccagcggc gtgcacacct tcccggctgt cctacagtcc       600
tcaggactct actccctcag cagcgtggtg accgtgccct ccagcagctt gggcacgaag       660
acctacacct gcaacgtaga tcacaagccc agcaacacca aggtggacaa gagagttggt       720
gagaggccag cacagggcag ggagggtgtc tgctggaagc caggctcagc cctcctgcct       780
ggacgcaccc cggctgtgca gccccagccc agggcagcaa ggcatgcccc atctgtctcc       840
tcacccggag gcctctgacc accccactca tgctcaggga gagggtcttc tggattttc        900
caccaggctc cgggcagcca caggctggat gccctaccc caggccctgc gcatacaggg        960
gcaggtgctg cgctcagacc tgccaagagc catatccggg aggaccctgc ccctgaccta      1020
agcccacccc aaaggccaaa ctctccactc cctcagctca gacaccttct ctcctcccag      1080
attcgagtaa ctcccaatct tctctctgca gagtccaaat atggtccccc atgcccatca      1140
tgcccaggta agccaaccca ggcctcgccc tccagctcaa ggcgggacag gtgccctaga      1200
gtagcctgca tccagggaca ggccccagcc gggtgctgac gcatccacct ccatctcttc      1260
ctcagcacct gagttcctgg ggggaccatc agtcttcctg ttcccccaa acccaagga        1320
cactctcatg atctcccgga cccctgaggt cacgtgcgtg gtggtggacg tgagccagga      1380
agaccccgag gtccagttca actggtacgt ggatggcgtg gaggtgcata atgccaagac      1440
aaagccgcgg gaggagcagt tcaacagcac gtaccgtgtg gtcagcgtcc tcaccgtcct      1500
gcaccaggac tggctgaacg gcaaggagta caagtgcaag gtctccaaca aaggcctccc      1560
gtcctccatc gagaaaacca tctccaaagc caaaggtggg acccacgggg tgcgagggcc      1620
acatggacag aggtcagctc ggcccaccct ctgccctggg agtgaccgct gtgccaacct      1680
ctgtccctac agggcagccc cgagagccac aggtgtacac cctgcccca tcccaggagg      1740
agatgaccaa gaaccaggtc agcctgacct gcctggtcaa aggcttctac cccagcgaca      1800
tcgccgtgga gtgggagagt aatgggcagc cggagaacaa ctacaagacc acgcctcccg      1860
tgctggactc cgacggctcc ttcttcctct acagcaggct aaccgtggac aagagcaggt      1920
ggcaggaggg gaatgtcttc tcatgctccg tgatgcatga ggctctgcac aaccactaca      1980
cacagaagag cctctccctg tctctgggta aatgagtgcc agggcggca agcccccgct       2040
cccccgggctc tcggggtcgc gcgaggatgc ttggcacgta cccgtctac atacttccca      2100
ggcacccagc atgaaataa agcacccacc actgccctgg gccccgtgaa gactgtgatg      2160
gttcttccca cgggtcaggc cgagtctgag gcctgagtga catgagggag gcagagcggg      2220
```

```
tcccactgtc cccacactgg cccaggctgt gcaggtgtgc ctgggccacc tagggtgggg      2280
ctcagccagg ggctgccctc ggcagggtgg gggatttgcc agcgtggccc tccctccagc      2340
agcaggacta tagaggatca taatcagcca taccacattt gtagaggttt tacttgcttt      2400
aaaaaacctc ccacacctcc ccctgaacct gaaacataaa atgaatgcaa ttgttgttgt      2460
taacttgttt attgcagctt ataatggtta caaataaagc aatagcatca caaatttcac      2520
aaataaagca ttttttttcac tgcattctag ttgtggtttg tccaaactca tcaatgtatc     2580
ttatcatgtc tggatcctct acgccggacg catcgtggcc ggcatcaccg cgccacagg       2640 tgcggttgct ggcgcctata tcgccgacat caccgatggg aagatcgggc tcgccacttc      2700
cgggctcatg agcgcttgtt tcggcgtggg tatggtggca ggcccgtggc cggggggactg     2760 ttgggcgcca tctccttgca tgcaccattc cttgcggcgg cggtgctcaa cggcctcaac      2820
ctactactgg gctgcttcct aatgcaggag tcgcataagg gagagcgtcg acctcgggcc      2880
gcgttgctgg cgttttttcca taggctccgc ccccctgacg agcatcacaa aaatcgacgc    2940
tcaagtcaga ggtggcgaaa cccgacagga ctataaagat accaggcgtt ccccctggga     3000
agctccctcg tgcgctctcc tgttccgacc ctgccgctta ccggatacct gtccgccttt     3060
ctcccttcgg gaagcgtggc gctttctcaa tgctcacgct gtaggtatct cagttcggtg     3120
taggtcgttc gctccaagct gggctgtgtg cacgaacccc ccgttcagcc cgaccgctgc     3180
gccttatccg gtaactatcg tcttgagtcc aacccggtaa gacacgactt atcgccactg     3240
gcagcagcca ctggtaacag gattagcaga gcgaggtatg taggcggtgc tacagagttc     3300
ttgaagtggt ggcctaacta cggctacact agaaggacag tatttggtat ctgcgctctg     3360
ctgaagccag ttaccttcgg aaaaagagtt ggtagctctt gatccggcaa acaaaccacc     3420
gctggtagcg gtggtttttt tgtttgcaag cagcagatta cgcgcagaaa aaaaggatct     3480
caagaagatc ctttgatctt ttctacgggg tctgacgctc agtggaacga aaactcacgt     3540
taagggattt tggtcatgag attatcaaaa aggatcttca cctagatcct tttaaattaa     3600
aaatgaagtt ttaaatcaat ctaaagtata tatgagtaaa cttggtctga cagttaccaa     3660
tgcttaatca gtgaggcacc tatctcagcg atctgtctat ttcgttcatc catagttgcc     3720
tgactccccg tcgtgtagat aactacgata cgggagggct taccatctgg ccccagtgct     3780
gcaatgatac cgcgagaccc acgctcaccg gctccagatt tatcagcaat aaaccagcca     3840
gccggaaggg ccgagcgcag aagtggtcct gcaactttat ccgcctccat ccagtctatt     3900
aattgttgcc gggaagctag agtaagtagt tcgccagtta atagtttgcg caacgttgtt     3960
gccattgcta caggcatcgt ggtgtcacgc tcgtcgtttg gtatggcatc attcagctcc     4020
ggttcccaac gatcaaggcg agttacatga tcccccatgt tgtgcaaaaa agcggttagc     4080
tccttcggtc ctccgatcgt tgtcagaagt aagttggccg cagtgttatc actcatggtt     4140
atggcagcac tgcataattc tcttactgtc atgccatccg taagatgctt ttctgtgact     4200
ggtgagtact caaccaagtc attctgagaa tagtgtatgc ggcgaccgag ttgctcttgc     4260
ccggcgtcaa cacgggataa taccgcgcca catagcagaa ctttaaaagt gctcatcatt     4320
ggaaaacgtt cttcggggcg aaaactctca aggatcttac cgctgttgag atccagttcg     4380
atgtaaccca ctcgtgcacc caactgatct tcagcatctt ttactttcac cagcgtttct     4440
gggtgagcaa aaacaggaag gcaaaatgcc gcaaaaaagg gaataagggc gacacggaaa     4500
tgttgaatac tcatactctt ccttttttcaa tattattgaa gcatttatca gggttattgt     4560
```

```
ctcatgagcg gatacatatt tgaatgtatt tagaaaaata aacaaatagg ggttccgcgc    4620
acatttcccc gaaaagtgcc acctgacgtc taagaaacca ttattatcat gacattaacc    4680
tataaaaata ggcgtatcac gaggccctga tggctctttg cggcacccat cgttcgtaat    4740
gttccgtggc accgacgaca accctcaaga gaaaatgtaa tcacactggc tcaccttcgg    4800
gtgggccttt ctgcgtttat aaggagacac tttatgttta agaaggttgg taaattcctt    4860
gcggctttgg cagccaagct agagatctct agcttcgtgt caaggacggt gactgcagtg    4920
aataataaaa tgtgtgtttg tccgaaatac gcgttttgag atttctgtcg ccgactaaat    4980
tcatgtcgcg cgatagtggt gtttatcgcc gatagagatg gcgatattgg aaaaatcgat    5040
atttgaaaat atggcatatt gaaaatgtcg ccgatgtgag tttctgtgta actgatatcg    5100
ccatttttcc aaaagtgatt tttgggcata cgcgatatct ggcgatagcg cttatatcgt    5160
ttacggggga tggcgataga cgactttggt gacttgggcg attctgtgtg tcgcaaatat    5220
cgcagtttcg atataggtga cagacgatat gaggctatat cgccgataga ggcgacatca    5280
agctggcaca tggccaatgc atatcgatct atacattgaa tcaatattgg ccattagcca    5340
tattattcat tggttatata gcataaatca atattggcta ttggccattg catacgttgt    5400
atccatatca taatatgtac atttatattg gctcatgtcc aacattaccg ccatgttgac    5460
attgattatt gactagttat taatagtaat caattacggg gtcattagtt catagcccat    5520
atatggagtt ccgcgttaca taacttacgg taaatggccc gcctggctga ccgcccaacg    5580
acccccgccc attgacgtca ataatgacgt atgttcccat agtaacgcca atagggactt    5640
tccattgacg tcaatgggtg gagtatttac ggtaaactgc ccacttggca gtacatcaag    5700
tgtatcatat gccaagtacg ccccctattg acgtcaatga cggtaaatgg cccgcctggc    5760
attatgccca gtacatgacc ttatgggact ttcctacttg gcagtacatc tacgtattag    5820
tcatcgctat taccatggtg atgcggtttt ggcagtacat caatgggcgt ggatagcggt    5880
ttgactcacg gggatttcca agtctccacc ccattgacgt caatgggagt ttgttttggc    5940
accaaaatca acgggacttt ccaaaatgtc gtaacaactc cgccccattg acgcaaatgg    6000
gcggtaggcg tgtacggtgg gaggtctata taagcagagc tcgtttagtg aaccgtcaga    6060
tcgcctggag acgccatcca cgctgttttg acctccatag aagacaccgg gaccgatcca    6120
gcctccgcgg ccgggaacgg tgcattggaa cgcggattcc ccgtgccaag agtgacgtaa    6180
gtaccgccta tagagtctat aggcccaccc ccttggcttc ttatgcatgc tatactgttt    6240
ttggcttggg gtctatacac ccccgcttcc tcatgttata ggtgatggta tagcttagcc    6300
tataggtgtg ggttattgac cattattgac cactcccta ttggtgacga tactttccat    6360
tactaatcca taacatggct ctttgccaca actctcttta ttggctatat gccaatacac    6420
tgtccttcag agactgacac ggactctgta tttttacagg atggggtctc atttattatt    6480
tacaaattca catatacaac accaccgtcc ccagtgcccg cagttttat taaacataac    6540 gtgggatctc cacgcgaatc tcgggtacgt gttccggaca tgggctcttc tccggtagcg    6600
gcggagcttc tacatccgag ccctgctccc atccctccag cgactcatgg tcgctcggca    6660
gctccttgct cctaacagtg gaggccagac ttaggcacag cacgatgccc accaccacca    6720
gtgtgccgca caaggccgtg gcggtagggt atgtgtctga aaatgagctc ggggagcggg    6780
cttgcaccgc tgacgcattt ggaagactta aggcagcggc agaagaagat gcaggcagct    6840
gagttgttgt gttctgataa gagtcagagg taactcccgt tgcggtgctg ttaacggtgg    6900
agggcagtgt agtctgagca gtactcgttg ctgccgcgcg cgccaccaga cataatagct    6960
```

```
gacagactaa cagactgttc ctttccatgg gtcttttctg cagtcaccgt ccttgacacg      7020
aagcttgggc tgcaggtcga tcgactctag aggatcgatc cccgggcgag ctc            7073
```

<210> SEQ ID NO 16
<211> LENGTH: 219
<212> TYPE: PRT
<213> ORGANISM: Artificial Sequence
<220> FEATURE:
<223> OTHER INFORMATION: Whereby sequence is a combination of mouse and
      human.

<400> SEQUENCE: 16

```
Gly Val His Ser Gln Val Gln Leu Val Glu Ser Gly Gly Gly Val Val
 1               5                  10                  15

Gln Pro Gly Arg Ser Leu Arg Leu Ser Cys Lys Ala Ser Gly Phe Asn
            20                  25                  30

Ile Lys Asp Tyr Tyr Met His Trp Val Arg Gln Ala Pro Gly Lys Gly
        35                  40                  45

Leu Glu Trp Ile Gly Leu Ile Asp Pro Glu Asn Gly Asn Thr Ile Tyr
    50                  55                  60

Asp Pro Lys Phe Gln Gly Arg Phe Thr Ile Ser Ala Asp Asn Ser Lys
65                  70                  75                  80

Asn Thr Leu Phe Leu Gln Met Asp Ser Leu Arg Pro Glu Asp Thr Ala
                85                  90                  95

Val Tyr Tyr Cys Ala Arg Asp Asn Ser Tyr Tyr Phe Asp Tyr Trp Gly
           100                 105                 110

Gln Gly Thr Pro Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val
    210                 215
```

<210> SEQ ID NO 17
<211> LENGTH: 12
<212> TYPE: PRT
<213> ORGANISM: Artificial Sequence
<220> FEATURE:
<223> OTHER INFORMATION: Whereby sequence is a combination of mouse and
      human.

<400> SEQUENCE: 17

```
Glu Ser Lys Tyr Gly Pro Pro Cys Pro Ser Cys Pro
 1               5                  10
```

<210> SEQ ID NO 18
<211> LENGTH: 109
<212> TYPE: PRT
<213> ORGANISM: Artificial Sequence
<220> FEATURE:
<223> OTHER INFORMATION: Whereby sequence is a combination of mouse and -continued human.

<400> SEQUENCE: 18

Pro Glu Phe Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser Gln Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Gly
                85                  90                  95

Leu Pro Ser Ser Ile Glu Lys Thr Ile Ser Lys Ala Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: Whereby sequence is a combination of mouse and
      human.

<400> SEQUENCE: 19

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 20
<211> LENGTH: 7864
<212> TYPE: DNA
<213> ORGANISM: Artificial Sequence
<220> FEATURE:
<221> NAME/KEY: unsure
<222> LOCATION: (4324)
<223> OTHER INFORMATION: Whereby sequence is a combination of mouse and
      human where nucleotide can be a, c, t, or g.

<400> SEQUENCE: 20
aattcaccat gggtgtgcca actcaggtat taggattact gctgctgtgg cttacagatg      60
caagatgtga tatccaaatg acacaatctc cttcttctct aagtgcttct gtcggagata     120
gagtaacaat tacatgtaag gcgagtcagg acattagaaa gtatttaaac tggtatcagc     180
aaaaacctgg gaaggctcct aagctactga tttattatgc aacaagtttg gcagatggag     240
taccttctag attttctggt tctggctctg gaacagacta cacattcaca atttcttctc     300

```
tccaacctga ggacattgct acatactact gcctacaaca tggtgagagt ccgtatacat    360
ttggacaagg aacaaaacta gagatcacaa gaactgttgc ggcgccgtct gtcttcatct    420
tcccgccatc tgatgagcag ttgaaatctg gaactgcctc tgttgtgtgc ctgctgaata    480
acttctatcc cagagaggcc aaagtacagt ggaaggtgga taacgccctc caatcgggta    540
actcccagga gagtgtcaca gagcaggaca gcaaggacag cacctacagc ctcagcagca    600
ccctgacgct gagcaaagca gactacgaga acacaaagt ctacgcctgc gaagtcaccc     660
atcagggcct gagctcgccc gtcacaaaga gcttcaacag gggagagtgt tagagggaga    720
agtgccccca cctgctcctc agttccagcc tggggatcat aatcagccat accacatttg    780
tagaggtttt acttgcttta aaaaacctcc cacacctccc cctgaacctg aaacataaaa    840
tgaatgcaat tgttgttgtt aacttgttta ttgcagctta taatggttac aaataaagca    900
atagcatcac aaatttcaca aataaagcat tttttcact gcattctagt tgtggtttgt     960
ccaaactcat caatgtatct tatcatgtct ggatcctcta cgccggacgc atcgtggccg   1020
gcatcaccgg cgccacaggt gcggttgctg gcgcctatat cgccgacatc accgatgggg   1080
aagatcgggc tcgccacttc gggctcatga gcgcttgttt cggcgtgggt atggtggcag   1140
gcccgtggcc gggggactgt tgggcgccat ctccttgcat gcaccattcc ttgcggcggc   1200
ggtgctcaac ggcctcaacc tactactggg ctgcttccta atgcaggagt cgcataaggg   1260
agagcgtcga cctcgggccg cgttgctggc gttttccat aggctccgcc ccctgacga    1320 gcatcacaaa atcgacgct caagtcagag gtggcgaaac ccgacaggac tataaagata   1380
ccaggcgttt ccccctggaa gctccctcgt gcgctctcct gttccgaccc tgccgcttac   1440
cggatacctg tccgcctttc tcccttcggg aagcgtggcg ctttctcaat gctcacgctg   1500
taggtatctc agttcggtgt aggtcgttcg ctccaagctg ggctgtgtgc acgaaccccc   1560
cgttcagccc gaccgctgcg ccttatccgg taactatcgt cttgagtcca acccggtaag   1620
acacgactta tcgccactgg cagcagccac tggtaacagg attagcagag cgaggtatgt   1680
aggcggtgct acagagttct tgaagtggtg gcctaactac ggctacacta aggacagt    1740 atttggtatc tgcgctctgc tgaagccagt taccttcgga aaaagagttg gtagctcttg   1800
atccggcaaa caaccaccg ctggtagcgg tggtttttt gtttgcaagc agcagattac     1860
gcgcagaaaa aaaggatctc aagaagatcc tttgatcttt tctacggggt ctgacgctca   1920
gtggaacgaa aactcacgtt aagggatttt ggtcatgaga ttatcaaaaa ggatcttcac   1980
ctagatcctt ttaaattaaa aatgaagttt taaatcaatc taaagtatat atgagtaaac   2040
ttggtctgac agttaccaat gcttaatcag tgaggcacct atctcagcga tctgtctatt   2100
tcgttcatcc atagttgcct gactccccgt cgtgtagata actacgatac gggagggctt   2160
accatctggc cccagtgctg caatgatacc gcgagaccca cgctcaccgg ctccagattt   2220
atcagcaata aaccagccag ccggaagggc cgagcgcaga agtggtcctg caactttatc   2280
cgcctccatc cagtctatta attgttgccg ggaagctaga gtaagtagtt cgccagttaa   2340
tagtttgcgc aacgttgttg ccattgctac aggcatcgtg gtgtcacgct cgtcgtttgg   2400
tatggcttca ttcagctccg gttcccaacg atcaaggcga gttacatgat cccccatgtt   2460
gtgcaaaaaa gcggttagct ccttcggtcc tccgatcgtt gtcagaagta agttggccgc   2520
agtgttatca ctcatggtta tggcagcact gcataattct cttactgtca tgccatccgt   2580
aagatgcttt tctgtgactg gtgagtactc aaccaagtca ttctgagaat agtgtatgcg   2640
```

-continued

```
gcgaccgagt tgctcttgcc cggcgtcaac acgggataat accgcgccac atagcagaac      2700
tttaaaagtg ctcatcattg gaaaacgttc ttcggggcga aaactctcaa ggatcttacc      2760
gctgttgaga tccagttcga tgtaacccac tcgtgcaccc aactgatctt cagcatcttt      2820
tactttcacc agcgtttctg ggtgagcaaa aacaggaagg caaaatgccg caaaaagggg      2880
aataagggcg acacggaaat gttgaatact catactcttc cttttcaat attattgaag       2940 catttatcag ggttattgtc tcatgagcgg atacatattt gaatgtattt agaaaaataa      3000
acaaataggg gttccgcgca catttccccg aaaagtgcca cctgacgtct aagaaaccat      3060
tattatcatg acattaacct ataaaaatag gcgtatcacg aggccctgat ggctctttgc      3120
ggcacccatc gttcgtaatg ttccgtggca ccgaggacaa ccctcaagag aaaatgtaat      3180
cacactggct caccttcggg tgggcctttc tgcgtttata aggagacact ttatgtttaa      3240
gaaggttggt aaattccttg cggctttggc agccaagcta gagatccggc tgtggaatgt      3300
gtgtcagtta gggtgtggaa agtccccagg ctccccagca ggcagaagta tgcaaagcat      3360
gcatctcaat tagtcagcaa ccaggctccc cagcaggcag aagtatgcaa agcatgcatc      3420
tcaattagtc agcaaccata gtcccgcccc taactccgcc catcccgccc ctaactccgc      3480
ccagttccgc ccattctccg ccccatggct gactaatttt ttttatttat gcagaggccg      3540
aggccgcctc ggcctctgag ctattccaga agtagtgagg aggcttttttt ggaggcctag     3600 gcttttgcaa aaagctagct ggggccacc gctcagagca ccttccacca tggccacctc      3660
agcaagttcc cacttgaaca aaacatcaa gcaaatgtac ttgtgcctgc cccagggtga      3720
gaaagtccaa gccatgtata tctgggttga tggtactgga gaaggactgc gctgcaaaac      3780
ccgcaccctg gactgtgagc ccaagtgtgt agaagagtta cctgagtgga attttgatgg      3840
ctctagtacc tttcagtctg agggctccaa cagtgacatg tatctcagcc ctgttgccat      3900
gtttcgggac cccttccgca gagatcccaa caagctggtg ttctgtgaag ttttcaagta      3960
caaccggaag cctgcagaga ccaatttaag gcactcgtgt aaacggataa tggacatggt      4020
gagcaaccag caccctggt ttggaatgga acaggagtat actctgatgg aacagatgg       4080 gcaccttttt ggttggcctt ccaatggctt tcctgggccc caaggtccgt attactgtgg      4140
tgtgggcgca gacaaagcct atggcaggga tatcgtggag gctcactacc gcgcctgctt      4200
gtatgctggg gtcaagatta caggaacaaa tgctgaggtc atgcctgccc agtgggaact      4260
ccaaatagga ccctgtgaag gaatccgcat gggagatcat ctctgggtgg cccgtttcat      4320
cttncatcga gtatgtgaag actttggggt aatagcaacc tttgaccca agcccattcc      4380 tgggaactgg aatggtgcag gctgccatac caactttagc accaaggcca tgcgggagga      4440
gaatggtctg aagcacatcg aggaggcat cgagaaacta gcaagcggc accggtacca      4500 cattcgagcc tacgatccca aggggggcct ggacaatgcc cgtggtctga ctgggttcca      4560
cgaaacgtcc aacatcaacg acttttctgc tggtgtcgcc aatcgcagtg ccagcatccg      4620 cattccccg actgtcggcc aggagaagaa aggttacttt gaagaccgcg gccctctgc      4680 caattgtgac ccctttgcag tgacagaagc catcgtccgc acatgccttc tcaatgagac      4740
tggccacgag cccttccaat acaaaaacta attagacttt gagtgatctt gagcctttcc      4800
tagttcatcc caccccgccc cagagagatc tttgtgaagg aaccttactt ctgtggtgtg      4860
acataattgg acaaactacc tacagagatt taaagctcta aggtaaatat aaaatttta      4920 agtgtataat gtgttaaact actgattcta attgtttgtg tatttagat tccaacctat       4980 ggaactgatg aatgggagca gtggtggaat gcctttaatg aggaaaacct gttttgctca      5040
```

```
gaagaaatgc catctagtga tgatgaggct actgctgact ctcaacattc tactcctcca    5100
aaaaagaaga gaaaggtaga acaccccaag gactttcctt cagaattgct aagttttttg    5160
agtcatgctg tgtttagtaa tagaactctt gcttgctttg ctatttacac cacaaaggaa    5220
aaagctgcac tgctatacaa gaaaattatg gaaaaatatt ctgtaacctt tataagtagg    5280
cataacagtt ataatcataa catactgttt tttcttactc cacacaggca tagagtgtct    5340
gctattaata actatgctca aaaattgtgt acctttagct ttttaatttg taaaggggtt    5400
aataaggaat atttgatgta tagtgcctag actagagatc ataatcagcc ataccacatt    5460
tgtagaggtt ttacttcctt taaaaaacct cccacacctc cccctgaacc tgaaacataa    5520
aatgaatgca attgttgttg ttaacttgtt tattgcagct tataatggtt acaaataaag    5580
caatagcatc acaaatttca caaataaagc atttttttca ctgcattcta gttgtggttt    5640
gtccaaactc atcaatgtat cttatcatgt ctggatctct agcttcgtgt caaggacggt    5700
gactgcagtg aataataaaa tgtgtgtttg tccgaaatac gcgttttgag atttctgtcg    5760
cctactaaat tcatgtcgcg cgatagtggt gtttatcgcc gatagagatg gcgatattgg    5820
aaaaatcgat atttgaaaat atggcatatt gaaaatgtcg ccgatgtgag tttctgtgta    5880
actgatatcg ccattttttcc aaaagtgatt tttgggcata cgcgatatct ggcgatagcg    5940
cttatatcgt ttacggggga tggcgataga cgactttggt gacttgggcg attctgtgtg    6000
tcgcaaatat cgcagtttcg atataggtga cagacgatat gaggctatat cgccgataga    6060
ggcgacatca agctggcaca tggccaatgc atatcgatct atacattgaa tcaatattgg    6120
ccattagcca tattattcat tggttatata gcataaatca atattggcta ttggccattg    6180
catacgttgt atccatatca taatatgtac atttatattg gctcatgtcc aacattaccg    6240
ccatgttgac attgattatt gactagttat taatagtaat caattacggg gtcattagtt    6300
catagcccat atatggagtt ccgcgttaca taacttacgg taaatggccc gcctggctga    6360
ccgcccaacg accccgccc attgacgtca ataatgacgt atgttccat agtaacgcca    6420
atagggactt tccattgacg tcaatgggtg gagtatttac ggtaaactgc ccacttggca    6480
gtacatcaag tgtatcatat gccaagtacg cccctattg acgtcaatga cggtaaatgg    6540
cccgcctggc attatgccca gtacatgacc ttatgggact ttcctacttg gcagtacatc    6600
tacgtattag tcatcgctat taccatggtg atgcggtttt ggcagtacat caatgggcgt    6660
ggatagcggt ttgactcacg gggatttcca agtctccacc ccattgacgt caatgggagt    6720
tgttttggc accaaaatca acgggacttt ccaaaatgtc gtaacaactc cgccccattg    6780
acgcaaatgg gcggtaggcg tgtacggtgg gaggtctata taagcagagc tcgtttagtg    6840
aaccgtcaga tcgcctggag acgccatcca cgctgtttg acctccatag aagacaccgg    6900
gaccgatcca gcctccgcgg ccgggaacgg tgcattggaa cgcggattcc ccgtgccaag    6960
agtgacgtaa gtaccgccta tagagtctat aggcccaccc ccttggcttc ttatgcatgc    7020
tatactgttt ttggcttcgg gtctatacac ccccgcttcc tcatgttata ggtgatggta    7080
tagcttagcc tataggtgtg ggttattgac cattattgac cactccccta ttggtgacga    7140
tactttccat tactaatcca taacatggct ctttgccaca actctcttta ttggctatat    7200
gccaatacac tgtccttcag agactgacac ggactctgta tttttacagg atggggtctc    7260
atttattatt tacaaattca catatacaac accaccgtcc ccagtgcccg cagtttttat    7320
taaacataac gtgggatctc cacgcgaatc tcgggtacgt gttccggaca tgggctcttc    7380
```

```
tccggtagcg gcggagcttc tacatccgag ccctgctccc atgcctccag cgactcatgg    7440
tcgctcggca tctccttgct cctaacagtg gaggccagac ttaggcacag cacgatgccc    7500
accaccacca gtgtgccgca caaggccgtg gcggtagggt atgtgtctga aaatgagctc    7560
ggggagcggg cttgcaccgc tgacgcattt ggaagactta aggcagcggc agaagaagat    7620
gcaggcagct gagttgttgt gttctgataa gagtcagagg taactcccgt tgcggtgctg    7680
ttaacggtgg agggcagtgt agtctgagca gtactcgttg ctgccgcgcg cgccaccaga    7740
cataatagct gacagactaa cagactgttc ctttccatgg gtcttttctg cagtcaccgt    7800
ccttgacacg aagcttgggc tgcaggtcga tcgactctag aggatcgatc cccgggcgag    7860
ctcg                                                                 7864

<210> SEQ ID NO 21
<211> LENGTH: 19
<212> TYPE: DNA
<213> ORGANISM: Artificial Sequence
<220> FEATURE:
<223> OTHER INFORMATION: Sequence is a combination of mouse and human

<400> SEQUENCE: 21
gtcaccgtcc ttgacacga                                                 19

<210> SEQ ID NO 22
<211> LENGTH: 27
<212> TYPE: DNA
<213> ORGANISM: Artificial Sequence
<220> FEATURE:
<223> OTHER INFORMATION: Sequence is a combination of mouse and human

<400> SEQUENCE: 22
acgtcagtgg caggaactgt gcttcga                                        27
```

CDR-GRAFTED ANTI-TISSUE FACTOR ANTIBODIES AND METHODS OF USE THEREOF

CROSS REFERENCE TO RELATED APPLICATIONS

This application is a continuation of U.S. application Ser. No. 11/591,361, filed 1 Nov. 2006, granted on 9 Jun. 2009 as U.S. Pat. No. 7,544,790, which is a divisional of U.S. application Ser. No. 10/313,392 filed Dec. 4, 2002, granted on 26 Jun. 2007 under U.S. Pat. No. 7,235,380, which is a continuation of U.S. application Ser. No. 08/480,120 filed Jun. 7, 1995, now abandoned. The entire contents of each of the aforementioned applications are incorporated herein by reference.

FIELD OF THE INVENTION

Monoclonal antibodies capable of inhibiting tissue factor (TF) are useful as anticoagulants. Conventional rodent monoclonal antibodies, however, have limited use in human therapeutic and diagnostic applications due to immunogenicity and short serum half-life. The present invention provides CDR-grafted monoclonal antibodies against TF that retain the high binding affinity of rodent antibodies but have reduced immunogenicity. The present humanized antibodies are potent anticoagulants and are thus useful in the treatment and prophylaxis of human thrombotic disease. The invention also provides methods of making the CDR-grafted antibodies and pharmaceutical compositions for the attenuation or prevention of coagulation.

BACKGROUND OF THE INVENTION

The coagulation of blood involves a cascading series of reactions leading to the formation of fibrin. The coagulation cascade consists of two overlapping pathways, both of which are required for hemostasis. The intrinsic pathway comprises protein factors present in circulating blood, while the extrinsic pathway requires tissue factor, which is expressed on the cell surface of a variety of tissues in response to vascular injury. Davie et al., 1991, *Biochemistry* 30: 10363. Agents that interfere with the coagulation cascade, such as heparin and coumarin derivatives, have well-known therapeutic uses in the prophylaxis of venous thrombosis. Goodman and Gilman, eds., 1980, *The Pharmacological Basis of Therapeutics*, MacMillan Publishing Co., Inc., New York.

Tissue factor (TF) has been investigated as a target for anticoagulant therapy. TF is a membrane glycoprotein that functions as a receptor for factor VII and VIIa and thereby initiates the extrinsic pathway of the coagulation cascade in response to vascular injury. In addition to its role in the maintenance of hemostasis by initiation of blood clotting, TF has been implicated in pathogenic conditions. Specifically, the synthesis and cell surface expression of TF has been implicated in vascular disease (Wilcox et al., 1989, *Proc. Natl. Acad. Sci.* 86:2839 and gram-negative septic shock (Warr et al., 1990, *Blood* 22:1481).

Ruf et al, (1991), Thrombosis and Haemostasis-:529) characterized the anticoagulant potential of murine monoclonal antibodies against human TF. The inhibition of TF function by most of the monoclonal antibodies that were assessed was dependent upon the dissociation of the TF!VIIa complex that is rapidly formed when TF contacts plasma. Such antibodies were thus relatively slow inhibitors of TF in plasma. One monoclonal antibody, TF8-5G9, was capable of inhibiting the TF!VIIa complex without dissociation of the complex, thus providing an immediate anticoagulant effect in plasma. Ruf et al. suggest that mechanisms that inactivate the TF!VIIa complex, rather than prevent its formation, may provide strategies for interruption of coagulation in vivo.

The therapeutic use of monoclonal antibodies against TF is limited in that currently available monoclonals are of rodent origin. The use of rodent antibodies in human therapy presents numerous problems, the most significant of which is immunogenicity. Repeated doses of rodent monoclonal antibodies have been found to elicit an antibody (HAMA), which can result in immune complex disease and/or neutralization of the therapeutic antibody. See, e.g., Jaffers et al (1986) *Transplantation* 11:572. While the use of human monoclonal antibodies would address this limitation, it has proven difficult to generate large amounts of human monoclonal antibodies by conventional hybridoma technology.

Recombinant technology has been used in an effort to construct "humanized" antibodies that maintain the high binding affinity of rodent monoclonal antibodies but exhibit reduced immunogenicity in humans. Chimeric antibodies have been produced in which the variable (V) region of a mouse antibody is combined with the constant (c) region of a human antibody in an effort to maintain the specificity and affinity of the rodent antibody but reduce the amount of protein that is nonhuman and thus immunogenic. While the immune response to chimeric antibodies is generally reduced relative to the corresponding rodent antibody, the immune response cannot be completely eliminated, because the mouse V region is capable of eliciting an immune response. Lobuglio et al (1989) *Proc. Natl. Acad. Sci.* 86:4220; Jaffers et al (1986) *Transplantation* 41:572.

In a recent approach to reducing immunogenicity of rodent antibodies, only the rodent complementarity determining regions (CDRs), rather than the entire V doman, are transplanted to a human antibody. Such humanized antibodies are known as CDR grafted antibodies. CDRs are regions of hypervariability in the V regions that are flanked by relatively conserved regions known as the framework (FR) regions. Each V domain contains three CDRs flanked by four FRs. The CDRs fold to form the antigen binding site of the antibody, while the FRs support the structural conformations of the V domains. Thus by transplanting the rodent CDRs to a human antibody, the antigen binding domain can theoretically also be transferred. Owens et al (1994) *J. Immunol. Methods* 168: 149 and Winter et al (1993) *Immunology Today* 11:243 review the development of CDR-grafted antibodies.

Orlandi et al (1989) *Proc. Natl. Acad. Sci. USA* 86:3833 constructed a humanized antibody against the relatively simple hapten nitrophenacetyl (NP). The CDRgrafted antibody contained mouse CDRs and human FRs, and exhibited NP binding activity similar to the native mouse antibody. However, the construction of CDR grafted antibodies recognizing more complex antigens has resulted in antibodies having binding activity significantly lower than the native rodent antibodies.

In numerous cases it has been demonstrated that the mere introduction of rodent CDRs into a human antibody background is insufficient to maintain full binding activity, perhaps due to distortion of the CDR conformation by the human FR.

For example, Gorman et al (1991) *Proc. Natl. Acad. Sci.* 88:4181 compared two humanized antibodies against human CO4 and observed considerably different avidities depending upon the particular human framework region of the humanized antibody. Co et al. *Proc. Natl. Acad. Sci. USA* 88:2869 required a refined computer model of the murine antibody of interest in order to identify critical amino acids to be considered in the design of a humanized antibody. Kettleborough et al (1991) *Protein Engineering* 1:773 report the influence of particular FR residues of a CDR-grafted antibody on antigen binding, and propose that the residues may directly interact with antigen, or may alter the conformation of the CDR loops. Similarly, Singer et al (1993) *J. Immunol.* 150:2844 report that optimal humanization of an anti-CO18 murine monoclonal antibody is dependent upon the ability of the selected FR to support the CDR in the appropriate antigen binding conformation. Accordingly, recreation of the antigen binding site requires consideration of the potential intrachain interactions between the FR and CDR, and manipulation of amino acid residues of the FR that maintain contacts with the loops formed by the CDRs. While general theoretical guidelines have been proposed for the design of humanized antibodies (see e.g., Owens et al), in all cases the procedure must be tailored and optimized for the particular rodent antibody of interest.

There is a need in the art for humanized antibodies with reduced immunogenicity and comparable binding affinity relative to the parent rodent antibody for various therapeutic applications. In particular, there is a need for a humanized antibody against human tissue factor having anticoagulant activity and useful in the treatment and prevention of thrombotic disease.

SUMMARY OF THE INVENTION

The present invention is directed to CDR grafted antibodies capable of inhibiting human tissue factor wherein the CDRs are derived from a non-human monoclonal antibody against tissue factor and the FR and constant (c) regions are derived from one or more human antibodies. In a preferred embodiment, the murine monoclonal antibody is TF8-5G9.

In another embodiment, the present invention provides a method of producing a CDR-grafted antibody capable of inhibiting human tissue factor which method comprises constructing one or more expression vectors containing nucleic acids encoding CDR-grafted antibody heavy and light chains, transfecting suitable host cells with the expression vector or vectors, culturing the transfected host cells, and recovering the CDR-grafted antibody.

The present invention also provides a method of attenuation of coagulation comprising administering a CDR-grafted antibody capable of inhibiting human tissue factor to a patient in need of such attenuation.

The present invention further provides a method of treatment or prevention of thrombotic disease comprising administering a CDR-grafted antibody capable of inhibiting human tissue factor to a patient in need of such treatment or prevention. In a preferred embodiment, the thrombotic disease is intravascular coagulation, arterial restenosis or arteriosclerosis.

Another embodiment of the present invention is directed to a pharmaceutical composition comprising CDR grafted antibodies capable of inhibiting human tissue factor and further comprising a pharmaceutically acceptable carrier.

BRIEF DESCRIPTION OF THE DRAWINGS

FIGS. 1A through 1E provide the nucleotide and deduced amino acid sequences of the heavy chain of murine monoclonal antibody TF8-SG9 (SEQ ID NO: 11).

FIGS. 2A through 2C provide the nucleotide and deduced amino acid sequences of the light chain of murine monoclonal antibody TF8-5G9 (SEQ ID NO: 12).

FIGS. 4A through 4S present the DNA sequence of expression vector pEe6TF8HCDR20 (SEQ ID NO: 15) and the amino acid sequence of the coding region 11 of the CDR-grafted heavy chain TF8HCDR20 (SEQ ID NOS:16, 17, 18, and 19).

FIGS. 5A through 5U present the DNA sequence of expression vector pEe12TF8LCDR3 and the amino acid sequence (SEQ ID NO:20) of the coding regions of the CDR-grafted light chain TF8LCDR3.

DETAILED DESCRIPTION OF THE INVENTION

Figure 3:
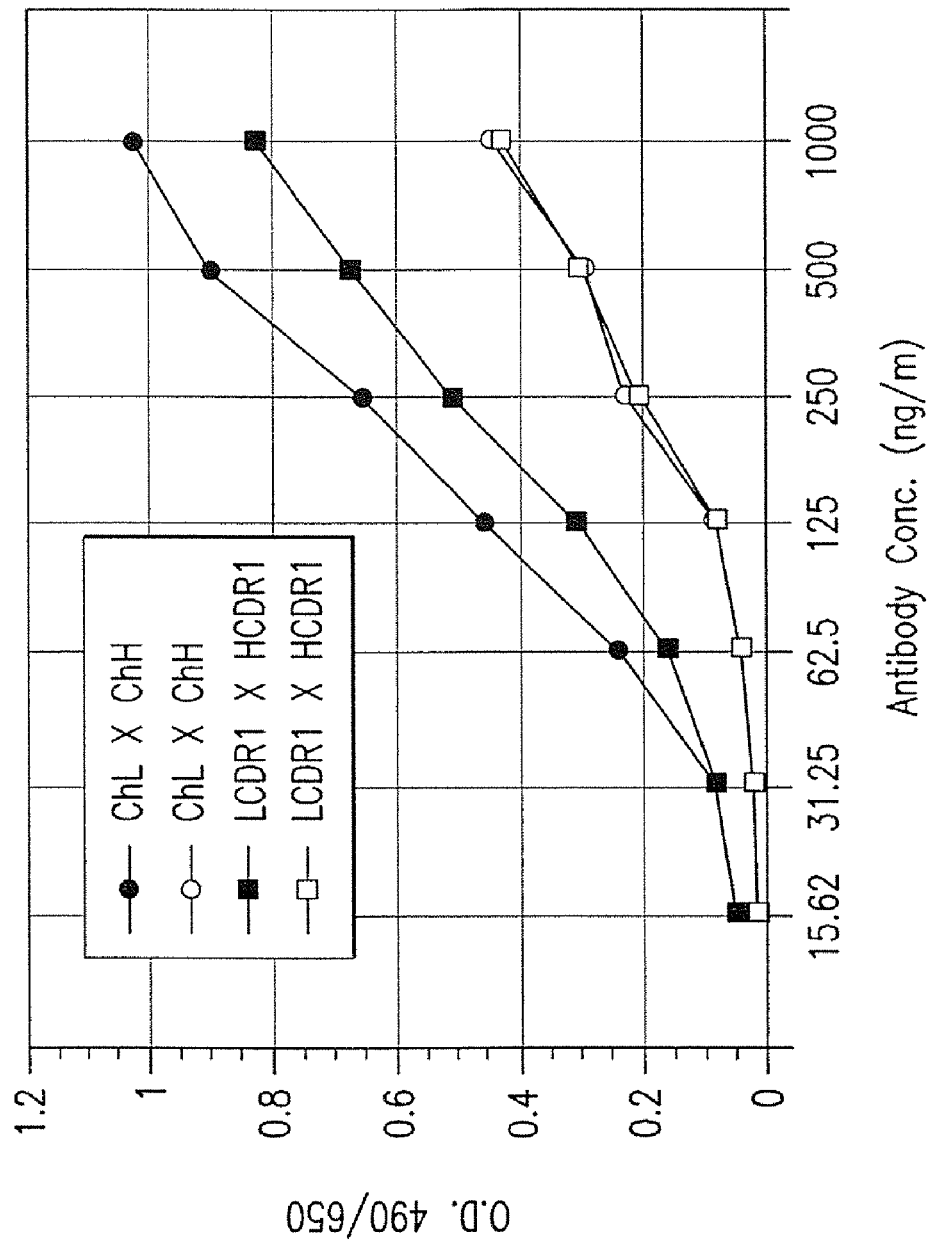
FIG. 3 is a graph depicting the ability of CDR-grafted antibody TF8HCDR1×TF8LCDR1 to bind to human tissue factor and to compete with murine monoclonal antibody TF85G9 for binding to tissue factor. Solid symbols indicate direct binding of TF8HCDR1×TF8LCDR1 and the positive control chimeric TF85G9 to tissue factor. Open symbols indicate competition binding of TF8HCDR1×TF8LCDR1 or chimeric TF85G9 with murine monoclonal antibody TF85G9.

The present invention provides CDR-grafted antibodies capable of inhibiting human tissue factor wherein the CDRs are derived from a non-human monoclonal antibody against tissue factor and the FR and C regions are derived from one or more human antibodies. The present invention further provides methods of making and using the subject CDR-grafted antibodies.

In accordance with the present invention, the CDR-grafted antibody is an antibody in which the CDRs are derived from a non-human antibody capable of binding to and inhibiting the function of human tissue factor, and the FR and C regions of the antibody are derived from one or more human antibodies. The CDRs derived from the non-human antibody preferably have about 90% to about 100% identity with the CDRs of the nonhuman antibody, although any and all modifications, including substitutions, insertions and deletions, are contemplated so long as the CDR-grafted antibody maintains the ability to bind to and inhibit tissue factor. The regions of the CDR-grafted antibodies that are derived from human antibodies need not have 100% identity with the human antibodies. In a preferred embodiment, as many of the human amino acid residues as possible are retained in order than immunogenicity is negligible, but the human residues, in particular residues of the FR region, are substituted as required and as taught herein below in accordance with the present invention. Such modifications as disclosed herein are necessary to support the antigen binding site formed by the CDRs while simultaneously maximizing the humanization of the antibody.

Non-human monoclonal antibodies against human tissue factor from which the CDRs can be derived are known in the art (Ruf et al., 1991; Morrisey et al., 1988, *Thrombosis Research* 52:247) or can be produced by well-known methods of monoclonal antibody production (see e.g. Harlow et al., eds., 1988, *Antibodies, A Laboratory Manual*, Cold Spring Harbor Laboratories, Cold Spring Harbor, N.Y.). Purified human tissue factor against which monoclonal antibodies can be raised is similarly well-known (Morrisey et al., 1987, *Cell* 50:129) and available to the skilled artisan. Murine monoclonal antibodies, and in particular murine monoclonal antibody TF8-5G9 disclosed by Ruf et al. and Morrisey et al., 1988, *Thrombosis Research* 52:247, and U.S. Pat. No. 5,223,427 are particularly preferred.

The ordinarily skilled artisan can determine the sequences of the CDRs by reference to published scientific literature or sequence databanks, or by cloning and sequencing the heavy and light chains of the antibodies by conventional methodology. In accordance with the present invention, the cDNA and amino acid sequences of the heavy chain (SEQ ID NOS: 1 and 2, respectively) and light chain (SEQ ID NOS.: 3 and 4, respectively) of murine monoclonal antibody TF8-5G9 are provided. The cDNA and deduced amino acid sequence of the murine TF8-5G9 are provided in FIGS. 1A through 1E. The cDNA and deduced amino acid sequence of the murine TF8-5G9 light chain is provided in FIGS. 2A through 2C.

Each of the heavy and light chain variable regions contain three CDRs that combine to form the antigen binding site. The three CDRs are surrounded by four FR regions that primarily function to support the CDRs. The sequences of the CDRs within the sequences of the variable regions of the heavy and light chains can be identified by computer-assisted alignment according to Kabat et al (1987) in *Sequences of Proteins of Immunological Interest*, 4th ed., United States Department of Health and Human Services, US Government Printing Office, Washington, D.C., or by molecular modeling of the variable regions, for example utilizing the ENCAD program as described by Levitt (1983) *J. Mol. Biol.* 168:595.

In a preferred embodiment the CDRs are derived from murine monoclonal antibody TF8-5G9. The preferred heavy chain CDRs have the following sequences:

```
CDR1    DYYMH              (SEQ ID NO: 5)
CDR2    LIDPENGNTIYDPKFQG  (SEQ ID NO: 6)
CDR3    DNSYYFDY           (SEQ ID NO:7)
```

The preferred light chain CDRs have the following sequences:

```
CDR1    KASQDIRKYLN        (SEQ ID NO: 8)
CDR2    YATSLAD            (SEQ ID NO: 9)
CDR3    LQHGESPYT          (SEQ ID NO: 10)
```

The sequences of the CDRs of the murine or other non-human antibody, and in particular the sequences of the CDRs of the TF8-5G9, may be modified by insertions, substitutions and deletions to the extent that the CDR grafted antibody maintains the ability to bind to and inhibit human tissue factor. The ordinarily skilled artisan can ascertain the maintenance of this activity by performing the functional assays described herein below. The CDRs can have, for example, from about 50% to about 100% homology to the CDRs of SEQ ID NOS: 5-10. In a preferred embodiment the CDRs have from about 80% to about 100% homology to the CDRs of SEQ ID NOS: 5-10. In a more preferred embodiment the CDRs have from about 90% to about 100% homology to the CDRs of the SEQ ID NOS.5-10.

The FR and C regions of the CDR-grafted antibodies of the present invention are derived from one or more human antibodies. Human antibodies of the same class and type as the antibody from which the CDRs are derived are preferred. The FR of the variable region of the heavy chain is preferably derived from the human antibody KOL (Schmidt et al., 1983, *Hoppe-Seyler's Z. Physiol. Chem.* 364:713. The FR of the variable region of the light chain is preferably derived from the human antibody REI. (EPP et al 1974. Eur. J. Biochem. 45:513). In accordance with the present invention, it has been discovered that certain residues of the human FR are preferably replaced by the corresponding residue of the non-human antibody from which the CDRs are derived. For example, certain FR residues of the TF8-5G9 are preferably retained to achieve optimal binding to antigen.

For convenience, the numbering scheme of Kabat et al has been adopted herein. Residues are designated by lower case numbers of hyphens as necessary to conform the present sequences to the standard Kabat numbered sequence.

In accordance with the present invention, residues that are retained in the FR region, e.g. residues that are not replaced by human FR residues, are determined according to the following guidelines. Residues that are idiosyncratic to the parent antibody, e.g. TF8-5G9, relative to a human consensus sequence of Kabat et al, are retained. Residues of the parent antibody that are in agreement with the consensus sequence are retained if the corresponding residue of the human antibody e.g. KOL or REI, is idiosyncratic. Residues that are part of the antibody loop canonical structures defined by Chothia et al (1989) *Nature* 342:877, such as residue 71 of the heavy and light chains, are retained. FR residues predicted to form loops, such as residues 28-30 of the heavy chain, are retained. FR residues predicted to influence the conformation of the CDRs such as residues 48 and 49 preceding CDR2 of the heavy chain, are retained. Residues that have been demonstrated to be critical in the humanization of other antibodies may also be retained. The foregoing guidelines are followed to the extent necessary to support the antigen binding site formed by the CDRs while simultaneously maximizing the humanization of the antibody.

The amino acid sequence of a representative CDR-grafted heavy chain variable region derived from murine monoclonal antibody TF8-SG9 and human antibody KOL is shown below. The CDR-grafted heavy chain is designated TF8HCDR1; murine residues were retained in the FR at residues 6, 17, 23, 24, 28, 29, 30, 48, 49, 68, 71, 73, 78, 88 and 91. CDRs are underlined.

```
                                              (SEQ ID NO: 11)
                 10         20         30       35ab
QVQLVQSGGG VVQPGRLLRL SCKASGFNIK DYYMH--WVR 50 52abc    60              70             80
QAPGKGLEWIG LIDP--ENGNTIYD PKFQGRFSIS ADTSK--NTAFL 82abc      90 100        110
QMDSLRPEDTAVY YCARDNSYYF DYWGQGTPVT VSS
```

The amino acid sequence of a representative CDR-grafted light chain variable region derived from murine monoclonal antibody TF8-5G9 and human antibody REI is shown below. The CDR-grafted light chain is designated TF8LCDR1; murine residues were retained in the FR at residues 39, 41, 46 and 105. CDRs are underlined.

```
                                          (SEQ ID NO: 12)
         10         20         30         40
    DIQMTQSPSS LSASVGDRVT ITCKASQDIR KYLNWYQQK 50         60         70         80
    WKAPKTLIYY ATSLADGVPS RFSGSGSGTD YTFTISSLQP 90        100
    EDIATYYCLQ HGESPYTFGQ GTKLEITR
```

A CDR-grafted antibody containing variable regions TF8HCDR1 and TF8LCDR1 has been demonstrated in accordance with the present invention to be as effective as murine monoclonal antibody TF8-5G9 in binding to human tissue factor. It has been further discovered in accordance with the present invention, by examination of the molecular structure of murine monoclonal antibody TF8-5G9, and by design, construction, and analysis of CDR-grafted antibodies, that the FR regions can be further humanized without the loss of antigen binding activity. In particular, the FR region may retain the human FR residue at residues 6, 17, 68, 73 and 78 of the heavy chain and residues 39, 41, 16 and 105 of the light chain, with maintenance of antigen binding activity.

In a most preferred embodiment, the heavy chain variable region contains a FR derived from human antibody KOL in which murine monoclonal antibody TF8-5G9 residues are retained at amino acids 23, 24, 28, 29, 30, 48, 49, 71, 88 and 91. The preferred heavy chain variable region is designed TF8HCDR20 and has the following sequence.

```
                                          (SEQ ID NO: 13)
         10         20         30       35ab
    QVQLVESGGG VVQPGRSLRL SCKASGFNIK DYYMH--WVR 50      52abc       60         70         80
    QAPGKGLEWIGL IDP--ENGNTIYD PKFQGRFTIS ADNSKNTLFL 82abc        90        100        110
    QMDSLRPEDTAVY YCARDNSYYF DYWGQGTPVT VSS
```

In a most preferred embodiment, the light chain variable region contains a FR derived from human antibody REI in which murine monoclonal antibody TF8-5G9 residues are retained at amino acids 39 and 105. The preferred light chain variable region is designated TF8LCDR20 and has the following sequence.

```
                                          (SEQ ID NO: 14)
         10         20         30         40
    DIQMTQSPSS LSASVGDRVT ITCKASQDIR KYLNWYQQKP 50         60         70         80
    GKAPKLLIYY ATSLADGVPS RFSGSGSGTD YTFTISSLQP 90        100
    EDIATYYCLQ HGESPYTFGQ GTKLEITR
```

It is within the ken of the ordinarily skilled artisan to make minor modifications of the foregoing sequences, including amino acid substitutions, deletions and insertions. Any such modifications are within the scope of the present invention so long as the resulting CDR-grafted antibody maintains the ability to bind to and inhibit human tissue factor. The ordinarily skilled artisan can assess the activity of the CDR-grafted antibody with reference to the functional assays described herein below.

The human constant region of the CDR-grafted antibodies of the present invention is selected to minimize effector function. The intended use of the CDR-grafted antibodies of the present invention is to block the coagulation cascade by inhibition of tissue factor, and thus antibody effector functions such as fixation of complement are not desirable. Antibodies with minimal effector functions include IgG2, IgG4, IgA, IgD and IgE. In a preferred embodiment of the present invention, the heavy chain constant region is the human IgG4 kappa constant region; and the light chain constant region is the human IgG4 kappa constant region.

In that effector functions may not be desirable for therapeutic uses, the present invention further contemplates active fragments of the CDR-grafted antibodies, and in particular Fab fragments and F(ab')2 fragments. Active fragments are those fragments capable of inhibiting human tissue factor. Fab fragments and F (ab')2 fragments may be obtained by conventional means/for example by cleavage of the CDR-grafted antibodies of the invention with an appropriate proteolytic enzyme such as papain or pepsin, or by recombinant production. The active fragments maintain the antigen binding sites of the CDR-grafted antibodies and thus are similarly useful therapeutically.

The ability of the CDR-grafted antibodies designed and constructed as taught in accordance with the present invention to bind and inhibit human tissue factor can be assessed by functional assays. For example, in a rapid and convenient assay, expression vectors containing nucleic acids encoding the CDR grafted heavy and light chains can be co-transfected into suitable host cells and transiently expressed. The resulting antibodies can be assessed by standard assays for ability to bind human tissue factor, and for ability to compete for binding to tissue factor with the human antibody from which the CDRs are derived.

For example, transient expression of nucleic acids encoding the CDR-grafted heavy and light chains in COS cells provides a rapid and convenient system to test antibody gene expression and function. Nucleic acids encoding the CDR-grafted heavy and light chains, respectively, are cloned into a mammalian cell expression vector, for example pSG5, described by Green et al (1988) *Nucleic Acids Res.* 16:369 and commercially available from Stratagene Cloning Systems, La Jolla, Calif. The pSG5 expression vector provides unique restriction sites for the insertion of the heavy and light chain genes, and in vivo expression is under the control of the SV40 early promoter. Transcriptional termination is signaled by the SV40 polyadenylation signal sequence.

The pSG5 based expression vector containing nucleic acids encoding the heavy and light chains are cotransfected into COS cells and cultured under conditions suitable for transient expression. Cell culture media is then harvested and examined for antibody expression, for example by an enzyme linked immunosorbent assay (ELISA), to determine that suitable levels of antibody have been produced. An ELISA may then be used to assess the ability of the CDR-grafted antibody to bind to human tissue factor. Human tissue factor is immobilized on a microtiter plate and the COS cell supernatant containing the CDR-grafted antibody is added followed by an incubation at room temperature for about one hour. The plates are then washed with a suitable detergent-containing buffer such as phosphate buffered saline (PBS)/Tween, followed by the addition of the components of a suitable detection system. For example, horseradish peroxidase conjugated goat antihuman kappa chain polyclonal antibody is added, followed by washing, followed by addition of substrate for horseradish peroxidase, and detection. The CDR-grafted antibodies within the scope of the present invention are those which are capable of binding to human tissue factor to a degree comparable to the non-human antibody from which the CDRs are derived as determined by the foregoing assay.

The ability of the CDR-grafted antibodies to inhibit the activity of human tissue factor in vivo can be conveniently assessed by the following in vitro assay that mimics in vivo coagulation events. In response to vascular injury in vivo, tissue factor binds to factor VII and facilitates the conversion of factor VII to a serine protease (factor VIIa). The factor VIIa-tissue factor complex converts factor X to a serine protease (factor Xa). Factor Xa forms a complex with factor Va (from the intrinsic coagulation pathway), resulting in the conversion of prothrombin to thrombin, which in turn results in the conversion of fibrinogen to fibrin. In a convenient in vitro functional assay, tissue factor is incubated in the presence of factor VIIa and the CDR grafted anti-tissue factor antibody produced in the transient expression system described above. Factor X is added and the reaction mixture is incubated, followed by an assay for factor Xa activity utilizing a chromogenic substrate for factor Xa (Spectrozyme Fxa, American Diagnostica, Inc., Greenwich, Conn.). The ability of the CDR-grafted antibody to inhibit factor X activation thus provides a measure of the ability of the CDR-grafted antibody to inhibit the activity of human tissue factor.

The CDR-grafted antibodies within the scope of the present invention are those which are capable of inhibiting human tissue factor to a degree comparable to the non-human antibody from which the CDRs are derived as determined by the foregoing assay. In one embodiment, the CDR-grafted antibody has at least 50% of the inhibitory activity of TF8-5G9 for human tissue factor. In a preferred embodiment, the CDR-grafted antibody has at least 70% of the inhibitory activity of TF8-5G9 for human tissue factor. In a more preferred embodiment, the CDR-grafted antibody has at least 80% of the inhibitory activity of TF8-5G9 for human tissue factor. In a most preferred embodiment, the CDR-grafted antibody has at least 90% of the inhibitory activity of TF8-5G9 human tissue factor.

In another embodiment, the present invention provides a method of producing a CDR-grafted antibody capable of inhibiting human tissue factor. The method comprises constructing an expression vector containing a nucleic acid encoding the CDR-grafted antibody heavy chain and an expression vector containing a nucleic acid encoding the CDR-grafted antibody light chain, transfecting suitable host cells with the expression vectors, culturing the transfected host cells under conditions suitable for the expression of the heavy and light chains, and recovering the CDR-grafted antibody. Alternately, one expression vector containing nucleic acids encoding the heavy and light chains may be utilized.

Standard molecular biological techniques, for example as disclosed by Sambrook et al. (1989), *Molecular Cloning: A Laboratory Manual* Cold Spring Harbor Press, Cold Spring Harbor, N.Y. may be used to obtain nucleic acids encoding the heavy and light chains of the CDR-grafted antibodies of the present invention. A nucleic acid encoding the CDR-grafted variable domain may be constructed by isolating cDNA encoding the antibody to be humanized, e.g. murine monoclonal antibody TF8-5G9, by conventional cloning methodology from the hybridoma producing the antibody, or by polymerase chain reaction (PCR) amplification of the variable region genes, as described for example by Winter et al., followed by site-directed mutagenesis to substitute nucleotides encoding the desired human residues into the FR regions. Alternately, the cDNA encoding the human antibody can be isolated, followed by site-directed mutagenesis to substitute nucleotides encoding the desired murine residues into the CDRs.

Nucleic acids encoding the CDR-grafted variable domain may also be synthesized by assembling synthetic oligonucleotides, for example utilizing DNA polymerase and DNA ligase. The resulting synthetic variable regions may then be amplified by PCR. Nucleic acids encoding CDR-grafted variable domains may also be constructed by PCR strand overlap methods that are known in the art and reviewed by Owens et al.

Accordingly, having determined the desired amino acid sequences of the CDR-grafted variable domains in accordance with the present invention, the ordinarily skilled artisan can obtain nucleic acids encoding the variable domains. Further, the skilled artisan is aware that due to the degeneracy of the genetic code, various nucleic acid sequences can be constructed that encode the CDR-grafted variable domains. All such nucleic acid sequences are contemplated by the present invention.

The nucleic acids encoding the CDR-grafted variable domains are linked to appropriate nucleic acids encoding the human antibody heavy or light chain constant region.

Nucleic acid sequences encoding human heavy and light chain constant regions are known in the art. It is within the ken of the ordinarily skilled artisan to include sequences that facilitate transcription, translation and secretion, for example start codons, leader sequences, the Kozak consensus sequence (Kozak, 1987, J. Mol. Biol. 196:947) and the like, as well as restriction endonuclease sites to facilitate cloning into expression vectors.

The present invention thus further provides nucleic acids encoding the heavy and light chains of CDR-grafted antibodies capable of inhibiting human tissue factor wherein the CDRs are derived from a murine monoclonal antibody against tissue factor and the FR and C regions are derived from one or more human antibodies.

In accordance with the present invention, representative nucleic acids encoding CDR-grafted heavy and light chains are constructed. The CDR-grafted heavy chain comprises a variable region containing FR regions derived from human antibody KOL and CDRs derived from murine monoclonal antibody TF8-5G9 and further comprises a constant region derived from the heavy chain of human IgG4. The CDR-grafted light chain comprises a variable region containing FR regions derived from human antibody REI and CDRs derived from murine monoclonal antibody TF8-SG9 and further comprises a constant region derived from human IgG4 kappa chain. Nucleic acids encoding the heavy and light chains were constructed by assembling the variable regions from synthetic nucleotides, amplifying the assembled variable regions by PCR, purifying the amplified nucleic acids, and ligating the nucleic acid encoding the variable region into a vector containing a nucleic acid encoding the appropriate human constant region.

The sequences of representative nucleic acids encoding CDR-grafted heavy and light chains are presented as nucleotides 1-2360 of SEQ ID No. 15 and nucleotides 1-759 of SEQ ID NO:20, respectively.

The nucleic acid sequence encoding a preferred heavy chain (nucleotides 1-2360 of SEQ ID NO: 15) is designated the TF8HCDR20 gene. The nucleic acid sequence contains the following regions: 5' EcoRI restriction site (nucleotides 1-6); Kozak sequence (nucleotides 7-15); start codon and leader sequence (nucleotides 16-72); CDR-grafted variable region (nucleotides 73-423); human IgG4 CH1 domain (nucleotides 424-717); human IgG4 intron 2 (nucleotides 718-1110); human IgG4 hinge (nucleotides 1111-1146); human IgG4 intron 3 (nucleotides 1147-1267); human IgG4 CH2 domain (nucleotides 1268-1594); human IgG4 intron 4 (nucleotides 1595-1691); human IgG4 CH3 domain (nucleotides 1692-2012); 3' untranslated region (nucleotides 2013-2354); 3' BamHI end spliced to Bc1I site of expression vector (nucleotides 2355-2360).

The nucleic acid sequence encoding a preferred light chain gene (nucleotides 1-759 of SEQ ID NO:20) is designated the TF8LCDR3 gene. The nucleic acid sequence contains the following regions: 5; EcoRI restriction site (nucleotides 1-5); Kozak sequence (nucleotides 6-8); start codon and leader sequence (nucleotides 9-68); CDR-grafted variable region (nucleotides 69-392); human kappa constant region (nucleotides 393-710); 3' untranslated region (nucleotides 711-753); 3' BamHI end spliced to Bcll site of expression vector (nucleotides 754-759).

The foregoing preferred sequences can be modified by the ordinarily skilled artisan to take into account degeneracy of the genetic code, and to make additions, deletions, and conservative and nonconservative substitutions that result in a maintenance of the function of the nucleic acid, i.e. that it encodes a heavy or light chain of a CDR-grafted antibody capable of inhibiting human tissue factor. Restriction sites and sequences that facilitate transcription and translation may be altered or substituted as necessary depending upon the vector and host system chosen for expression.

Suitable expression and hosts for production of the CDR-grafted antibodies of the present invention are known to the ordinarily skilled artisan. The expression vectors contain regulatory sequences, such as replicons and promoters, capable of directing replication and expression of heterologous nucleic acids sequences in a particular host cell. The vectors may also contain selection genes, enhancers, signal sequences, ribosome binding sites, RNA splice sites, polyadenylation sites, transcriptional terminator sequences, and so on. The vectors may be constructed by conventional methods well-known in the art, or obtained from commercial sources. The expression vectors preferably have convenient restriction sites at which the nucleic acids encoding the antibody chains of the invention are inserted. Myeloma expression vectors in which antibody gene expression is driven by the human cytomegalovirus promoter-enhancer or are particularly preferred.

Expression vectors containing a nucleic acid encoding the CDR-grafted heavy chain under the control of a suitable promoter and expression vectors containing a nucleic acid encoding the CDR-grafted light chain under the control of a suitable promoter are cotransfected into a suitable host cell. In another embodiment, nucleic acids encoding both heavy and light chains are provided in a single vector for transfection of a suitable host cell.

Suitable host cells or cell lines for expression of the CDR-grafted antibodies of the present invention include bacterial cells, yeast cells, insect cells, and mammalian cells such as Chinese hamster ovary (CHO) cells, COS cells, fibroblast cells and myeloid cells. Mammalian cells are preferred. CHO, COS and myeloma cells are particularly preferred. Myeloma cells are preferred for establishing permanent CDR-grafted antibody producing cell lines. Expression of antibodies in myeloma cells, bacteria, and yeast is reviewed by Sandhu (1992) *Critical Reviews in Biotechnology* 12:437. Expression in mammalian cells is reviewed by Owen et al.

Transfection of host cells by the expression vectors containing nucleic acids encoding the CDR grafted heavy and light chains can be accomplished by well-known to methods one of ordinary skill in the art. Such methods include, for example, calcium chloride transfection, calcium phosphate transfection, lipofection and electroporation. Suitable culture methods and conditions for the production of the CDR grafted antibodies are likewise well-known in the art. The CDR-grafted antibodies can be purified by conventional methods, including ammonium sulfate precipitation, affinity chromatography, gel electrophoresis, and the like. The ability of the CDR grafted antibodies to bind to and inhibit human tissue factor can be assessed by the in vitro assays described above.

The CDR-grafted antibodies of the present invention have a variety of utilities. For example, the antibodies are capable of binding to human tissue factor and thus are useful in assays for human tissue factor from body fluid samples, purification of human tissue factor, and so on.

The CDR-grafted antibodies of the present invention are capable of inhibiting human tissue factor. Human tissue factor is well-known to be an essential element in the human coagulation cascade. The ability of the antibodies of the present invention to disrupt the coagulation cascade is demonstrated by in vitro assays in which the antibodies prevent factor X activation. Accordingly, the present antibodies are useful in the attenuation of coagulation. The present invention thus provides a method of attenuation of coagulation comprising administering a therapeutically effective amount of CDR-grafted antibody capable of inhibiting human tissue factor to a patient in need of such attenuation.

Numerous thrombotic disorders are characterized by excessive or inappropriate coagulation and are effectively treated or prevented by administration of agents that interfere with the coagulation cascade. Accordingly, the present invention further provides a method of treatment or prevention of a thrombotic disorder comprising administering a therapeutically effective amount of a CDR-grafted antibody capable of inhibiting human tissue factor to a patient in need of such treatment or prevention. In a preferred embodiment, the thrombotic disorder is intravascular coagulation, arterial restenosis or arteriosclerosis. The antibodies of the invention may be used in combination with other antibodies or therapeutic agents.

A therapeutically effective amount of the antibodies of the present invention can be determined by the ordinarily skilled artisan with regard to the patient's condition, the condition being treated, the method of administration, and so on. A therapeutically effective amount is the dosage necessary to alleviate, eliminate, or prevent the thrombotic disorder as assessed by conventional parameters. For example, a therapeutically effective dose of a CDR-grafted antibody of the present invention may be from about 0.1 mg to about 20 mg per 70 kg of body weight. A preferred dosage is about 1.0 mg to about 5 mg per 70 kg of body weight.

A patient in need of such treatment is a patient suffering from a disorder characterized by inappropriate or excessive coagulation, or a patient at risk of such a disorder. For example, anticoagulant therapy is useful to prevent postoperative venous thrombosis, and arterial restenosis following balloon angioplasty.

The CDR-grafted antibodies of the present invention are useful in the same manner as comparable therapeutic agents, and the dosage level is of the same order of magnitude as is generally employed with those comparable therapeutic agents. The present antibodies may be administered in combination with a pharmaceutically acceptable carrier by methods known to one of ordinary skill in the art.

Another embodiment of the present invention is directed to a pharmaceutical composition comprising at least one CDRgrafted antibody capable of inhibiting human tissue factor and further comprising a pharmaceutically acceptable carrier. As used herein, "pharmaceutically acceptable carrier" includes any and all solvents, dispersion media, coatings, antibacterial and antifungal agents, isotonic and absorption delaying agents, and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

The antibodies can be administered by well-known routes including oral and parenteral, e.g., intravenous, intramuscular, intranasal, intradermal, subcutaneous, and the like. Parenteral administration and particularly intravenous administration is preferred. Depending on the route of administration, the pharmaceutical composition may require protective coatings.

The pharmaceutical forms suitable for injectionable use include sterile aqueous solutions or dispersions and sterile powers for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyol such as glycerol, propylene glycol, polyethylene glycol, suitable mixtures thereof, surfactants or vegetable oils. The antibodies may be incorporated into liposomes for parenteral administration. Sterilization can be accomplished by an art-recognized techniques, including but not limited to, addition of antibacterial or antifungal agents, for example, paraben, chlorobutanol, phenol, sorbic acid or thimersal. Further, isotonic agents such as sugars or sodium chloride may be incorporated in the subject compositions.

Production of sterile injectable solution containing the subject antibodies is accomplished by incorporating these antibodies in the required amount in the appropriate solvent with various ingredients enumerated above, as required, followed by sterilization, preferably filter sterilization. To obtain a sterile powder, the above solutions are vacuum dried or freeze-dried as necessary.

The following examples further illustrate the present invention.

Example 1

Isolation and Sequencing of TF8-5G9 Light Chain (LC) and Heavy Chain (HC)

Two DNA libraries were generated from oligo (dT)-primed TF8-5G9 hybridoma RNA utilizing standard molecular biology procedures as described by Sambrook et al. The cDNA was cloned into the Librarian II plasmid vector from Invitrogen (San Diego, Calif.), and the libraries were screened for cDNA clones encoding murine IgG HC and LC. A full-length cDNA clone for the heavy chain could not be isolated, despite the construction of two independent libraries. A random primed TF8-5G9 cDNA library was generated to obtain the missing 5' sequence of the heavy chain. Consequently, the heavy chain cDNA was in two pieces: a 5' clone of 390 nucleotides and a 3' clone of 1392 nucleotides. The two HC clones overlap by 292 nucleotides.

The HC and LC clones were completely sequenced were completely sequenced by the dideoxy chain termination method of Sanger et al. (1977) *Proc. Natl. Acad. Sci. USA* 74:5463. To verify the variable region sequence, sequence was obtained from PCR-amplified cDNA that had been synthesized from total TF8-5G9 hybridoma RNA. Total TF8-5G9 hybridoma RNA was isolated by the guanidinium thiocyanate method of Chrigwin et al (1970) *Biochemistry* 18:5294. cDNA was synthesized using the Perkin Elmer (Norwalk, Conn.) GeneAmp RNA Polymerase Chain Reaction (PCR) kit with an oligo (dT) primer. Components of the same kit were used in the PCR to amplify the LC and HC variable regions using primers based on the sequence that had been obtained for the cDNA clones. The amplified variable region fragments were gel-purified and sequenced according to the method of Tracy et al (1991) *BioTechniques* 11:68 on a Model 373A Applied Biosystems, Inc. (Foster City, Calif.) automated fluorescent DNA sequencer. The sequence for TF8-5G9 LC and HC obtained from RNA amplification and the sequence obtained from the cDNA clones agreed. The TF8-5G9 HC variable region sequence with protein translation is shown in FIG. 1 and SEQ ID NO:1, and that for the LC is shown in FIG. 2 and SEQ ID NO:3.

Example 2

Chimeric LC and HC Expression Vector Construction

In order to test the binding activity of the CDR-grafted anti-TF LC and HC individually, mouse-human chimeric TF8-5G9 LC and HC were constructed. This allowed the CDR-grafted LC to be tested for TF binding ability in combination with the chimeric HC, and the CDR-grafted HC to be tested in combination with the chimeric LC.

Primers were designed to amplify the TF8-5G9 LC variable region using as template cDNA clones in the Librarian II vector. The 5' primer was designed with an EcoRI site while the 3' primer was designed with a NarI site. PCR was used to amplify the LC variable region, generating a 433 bp fragment with a 5'EcoRI end and 3'NarI end. The fragment included the signal sequence from the TFB-5G9 Lc cDNA clone but incorporated a 2 base change in the arginine codon immediately following the ATG start codon. This change retained the arginine residue but made the sequence conform to the Kozak consensus sequence in order to potentially improve translation of the LC mRNA. The PCR amplified LC variable region fragment was digested with EcoRI and NarI restriction enzymes and purified by electrophoresis on a 2% Nusieve, 1% Seakem agarose gel (FMC Bio Products, Rockland, Me.).

The DNA was extracted from the gel slice and purified by the Geneclean (Bio 101, La Jolla, Calif.) procedure. The full-length chimeric TF8-5G9 LC gene was generated by cloning this DNA into the EcoRI and NarI sites of a pSP73 vector (Promega, Madison, Wis.) which contains the human kappa constant region. The gene was isolated from the pSP73 vector by EcoRI digestion and subcloned into the EcoRI site of the pSG5 mammalian cell expression vector (Stratagene Cloning Systems, La Jolla, Calif.).

The chimeric TF8-5G9 HC gene was assembled in a manner similar to that of the chimeric LC. Since there was no full-length HC cDNA isolated from the Librarian II vector cDNA libraries, the HC variable region fragment that was generated by the PCR from total TF8-5G9 hybridoma cell RNA was used as the template. Primers which incorporated an EcoRI site at the 5' end and a SacI site at the 3' end were used in the PCR to generate a 430 bp fragment which contained the TF8-5G9 HC Kozak sequence, start codon, signal sequence, and variable region. This fragment was digested with the restriction enzymes EcoRI and SacI, and gel-purified using the same procedure that was used with the chimeric LC construction.

The full-length TF8-5G9 chimeric HC gene was constructed by cloning the variable region fragment into the EcoRI and SacI sites of the pSG5 expression vector containing the human IgG4 constant region.

Example 3

Design and Construction of the CDR-Grafted heavy and Light Chain Genes

The variable region domains of the CDR-grafted HC and LC genes were designed with an EcoRI overhang at the 5' end followed by a Kozak sequence to improve antibody expression. The leader sequences were derived from the heavy and light chains of the murine monoclonal antibody B72.3 (Whittle et al. (1987) *Protein Engineering* 1:499). The 3' end of the variable regions were designed to have overhangs which allowed for splicing to the appropriate human constant region DNA.

In the initially designed CDR-grafted TF8-5G9 heavy and light chains the CDRs were derived from murine TF8-5G9 sequence while the frameworks were derived primarily from human antibody sequence. The human antibody KOL (Schmidt et al.) was used for the heavy chain frameworks, while the human antibody dimer (EPP et al.) was used for the light chain frameworks.

Several criteria were used to select murine framework residues in the design of the TF8-5G9 CDR-grafted heavy and light chain variable regions. Framework residues which, at a particular position, are idiosyncratic to TF8-SG9, were retained as murine sequence with the assumption that they contributed to its unique binding characteristics. TF8-5G9 murine residues were also retained at framework positions where they were in agreement with the human consensus sequence but where the corresponding residues in KOL or REI were idiosyncratic. Residues that are part of antibody loop canonical structures such as residue 71 (numbering according to Kabat et al.) of the heavy and light chains were also retained as murine sequence. Framework residues that form loops such as residues 26-30 of the HC were kept as TF8-5G9 murine sequence at positions were the murine sequence differed from the human. Residues known to directly influence the conformation of CDRs, such as 48 and 49 immediately preceding CDR2 of the HC, were also retained as murine sequence.

The amino acid sequence of the variable region for the initially designed CDR-grafted TF8-5G9 HC, TF8HCDR1, is shown in SEQ NO.:11. Murine residues were retained at framework positions 6, 17, 23, 24, 28, 29, 30, 48, 49, 68, 71, 73, 78, 88 and 91. The CDR grafted HC variable region was attached to a human IgG4 constant region.

The amino acid sequence of the variable region for the initially designed CDR-grafted TF8-5G9 LC, TF8LCDR1, is shown in SEQ ID NO:12. Murine residues were retained at framework positions 39, 41, 46 and 105. The CDR-grafted LC variable region was attached to a human kappa constant region.

The variable region for the CDR-grafted HC and LC described above were each assembled from 13 synthetic oligonucleotides where were synthesized by Research Genetics, Inc., Huntsville, Ala. These oligonucleotides ranged in length from 42 to 80 bases, and encoded both variable region strands. When the 6 complementary oligonucleotide pairs were annealed, the overhangs generated were 17 to 24 bases in length. These oligonucleotide pairs were combined, annealed at their complementary overhangs, and ligated to give the final full length double-stranded variable regions.

The HC variable region oligonucleotides were assembled into a 452 bp fragment which contains a 5' EcoR1 site and a 3' SacI site. The polymerase chain reaction was used to amplify this fragment. The resulting amplified DNA was purified on a 2% Nusieve, 1% Seakem agarose gel (FMC). The appropriate size band of DNA was excised and the DNA was recovered by the Geneclean (Bio 101) procedure. The fragment was then digested with EcoR1 and Sac1, and purified again by the Geneclean method. This HC variable region fragment with EcoR1 and SacI ends was cloned into the EcoR1 and SacI sites of the pSport-1 vector (GIBCO-BRL Life Technologies, Gaithersburg, Md.). DNA from several clones was isolated and sequenced to verify proper variable region assembly. All clones had unexpected base changes. One clone with the fewest base changes (two mismatches at bases 133 and 140) was selected to be corrected by site-directed mutagenesis according to Kunkel (1985) *Proc. Natl. Acad. Sci. USA* 82:488. Briefly, CJ236 (ung,dut-) competent cells (Invitrogen Corporation, San Diego, Calif.) were transformed with the ps port vector containing the CDR-grafted HC variable region with the two base mismatch. Single-stranded, uridine-incorporated DNA templates were purified from phage following M13 helper phage (stratagene Cloning Systems) infection of the transformed cells. Mutagenesis oligos containing the desired base changes were synthesized on an Applied Biosystems Model 380B DNA synthesizer. The mutagenesis oligos were annealed to the template DNA, and T7 DNA polymerase and T4 DNA Ligase (MutaGene InVitro Mutagenesis Kit, Bo-Rad Laboratories, Richmond, Calif.) were used to incorporate the oligo into a newly synthesized DNA strano. DH5α competent cells (GIBCO-BRL Life Technologies) were transformed with the double-stranded DNA. The original uridine-incorporated strand is destroyed while the newly synthesized strand containing the mutagenesis oligo is replicated. Phagemid DNA was prepared from the resulting mutagenesis clones and the variable regions were sequence to identify the clones which had incorporated the desired changes. The corrected HC EcoRI/SacI variable region fragment was excised from the pSport vector, purified and ligated into the EcoRI/SacI sites of a pSG5 vector containing the human IgG4 constant region. This resulted in the generation of a full-length humanized TF8-5G9 HC gene, TF8HCDR1, in the pSG5 cos cell expression vector. The vector was designated pSG5TF8HCDR1.

The CDR-grafted TF8-5G9 LC variable region was also amplified by the PCR from the assembled synthetic oligonucleotides into a 433 bp fragment which contained a 5' EcoRI site and a 3' NarI site. This fragment was purified as described above for the HC, digested with EcoRI and NarI and purified by the Geneclean procedure. This fragment was cloned into the EcoRI and NarI sites of a pSG5 vector which contains the human kappa constant region. This resulted in the generation of a full-length humanized TFS-5G9 LC gene, TF8LCDR1, in the pSG5 cos cell expression vector. Seven clones were sequenced, and one was found to have the desired CDR. The vector was designated PSQ5TFBLCDR1.

Example 4

Expression of the CDR-Grafted Heavy and Light Chain Genes in COS Cells

The transient expression of antibody genes in COS-1 cells provides a rapid and convenient system to test antibody gene expression and function. COS-1 cells were obtained from the American Type Culture Collection (CRL 1650) and cultured in Dulbecco's Modified Eagle Medium (DMEM, from GIBCO BRL Life Technologies) with 10% fetal calf serum. The pSGSTF8HCDR1 expression factor was cotransfected into COS cells with the pSGS chimeric LC expression vector using the DEAE-Dextran method followed by DMSO shock as described by Lopata et al. (1984) *Nucleic Acids Res.* 14:5707. After 4 days of culture, media was harvested from the wells and examined for antibody expression levels.

Antibody levels were determined by an ELISA based assembly assay. Plates were coated with a goat anti-human Fc specific antibody. Various dilutions of the COS cell supernatant containing secreted antibody were added, incubated for one hour, and washed. A horseradish peroxidase-linked goat anti-human kappa chain antibody was added, incubated for one hour at room temperature, and washed. Substrate for the horseradish peroxidase was added for detection. Antibody levels in the COS cell media were found to be nearly undetectable for the TF8HCDR1×chimeric LC. Upon closer examination of the TF8HCDR1 variable region sequence, it was found that an unexpected base change, which had occurred during the site-directed mutagenesis process described in Example 3, introduced a stop codon into framework 4 of the TFBHCDRI gene. This substitution was corrected by site-directed mutagenesis as described above. Thorough sequencing of the variable region confirmed that the correction was made with no additional changes introduced. Upon transfection of this corrected TF8HCDR1 gene with the chimeric LC, reasonable expression levels were obtained.

COS cells which had been co-transfected with the CDR-grafted LC expression vector, pSGTF8LCDR1, and either the chimeric HC or TFSHCDR1, produced antibody at reasonable levels. Antibody levels in cas cell supernatants ranged from 0.5 μg to 10.0 μg per ml.

Example 5

Binding of the CDR-Grafted TF8-5G9 to Tissue Factor

An ELISA was used to determine the ability of the CDR-grafted TF8-5G9 antibody, TF8HCDR1 x TF8LCDR1, to bind to tissue factor. Tissue factor was immobilized on a microtiter plate. The test COS cell supernatant, containing the CDR-grafted antibody, was added to the well, incubated for one hour at room temperature. Following three washes with PBS/Tween, a goat anti-human kappa chain polyclonal antibody conjugated to horseradish peroxidase was added, incubated for one hour at room temperature and washed. Substrate for the horseradish peroxidase was added for detection. The positive control was the TF8-5G9 chimeric antibody. The CDR-grafted TF8-5G9 antibody was able to bind to tissue factor to a degree comparable to the chimeric TF8-5G9 antibody (FIG. 3, solid symbols).

The ability of the humanized antibody to compete with murine TF8-5G9 for binding to tissue factor was also examined. Varying amounts of COS cell supernatant containing the test CDR-grafted antibody and a fixed amount of murine TF8-5G9 were added simultaneously to wells coated with tissue factor. Binding was allowed to occur for one hour at room temperature. The wells were washed three times with PES/Tween. A goat anti-human kappa chain antibody conjugated to horseradish peroxidase was added, incubated for one hour at room temperature and washed. Substrate for the horseradish peroxidase was added for detection. The positive antibody competed as well as the chimeric antibody with murine TF8-5G9 for binding to TF.

These data indicate that the initially designed CDR-grafted antibody, TF8HCDR1 x TF8LCDR1, was approximately as active as the chimeric TF8-5G9 in binding to TF and competing with the murine antibody for binding to TF.

Example 6

Construction and Characterization of Additional CDR-Grafted Heavy Chains

Upon examination of the molecular structure of murine TF8-5G9, framework residues at positions 27, 68, 73 and 78 were found to lie on the antibody surface and had no discernible contact with the CDRs. These framework residues were of murine sequence in TF8HCDR1 but were changed to the human KOL sequence in various combinations to generate a series of CDR-grafted heavy chains with framework residue variations. The changes were made by the process of site-directed mutagenesis as described in Example 3. Each CDR-grafted heavy chain version was expressed in COS cells in combination with the CDR-grafted LC, TF8LCDR1, and tested for its ability to bind TF and compete with murine TF8-5G9 for binding. Every version of the CDR-grafted heavy chain in combination with TF8LCDR1 was shown to bind TF with an affinity comparable to chimeric TF8-5G9. Every CDR grafted HC in combination with TF8LCDR1 was able to compete with murine TF8-5G9 for binding to TF to a degree comparable to the chimeric antibody.

Changes in sequence from murine to human for HC framework positions 6, 7, 68, 73 and 78 did not adversely affect the antigen binding ability of the antibody. The CDR-grafted HC version which had human sequence at all of these positions, and thus was the most humanized HC, was TF8HCDR20.

The complete sequence of the TF8HCDR20 gene was determined. The DNA sequence is shown as a 2360 bp EcoRI/BamHI insert with protein translation in the pEe6TF8HCDR20 expression vector in FIG. 4 and SEQ ID NO: 15

The essential regions of the gene are as follows:

| Nucleotide # | Region |
| --- | --- |
| 1-6 | 5' EcoRI restriction site |
| 7-15 | Kozak sequence |
| 16-72 | Start codon and leader sequence |
| 73-423 | CDR-grafted variable region |
| 424-717 | Human IgG4CH1 domain |
| 718-1110 | Human IgG4 intron 2 |
| 1111-1146 | Human IgG4 hinge |
| 1147-1267 | Human IgG4 intron 3 |
| 1268-1594 | Human IgG4 CH2 domain |
| 1595-1691 | Human IgG4 intron 4 |
| 1692-2012 | Human IgG4 CH3 domain |
| 2013-2354 | 3' untranslated region |
| 2355-2360 | 3' BamHI end spliced to BclI site of the expression vector |

Example 7

Construction and Characterization of Additional CDR-Grafted Light Chains

The initially designed CDR-grafted LC, TF8LCDR1, contained four framework residues from the murine TF8-5G9 sequence. At two of these positions, 39 and 105, the human REI framework sequence is unique to REI; however, the murine TF8-5G9 LC sequence is in agreement with the human consensus sequence. The other two murine framework residues, trp41 and thr46, are unique to TF8-5G9. Several versions of the CDR-grafted LC were generated in which the sequence at these four positions were changed from the murine to the human REI in various combinations. These changes were made by site-directed mutagenesis. Each version of the CDR-grafted LC was expressed in cos cells in combination with the CDR-grafted HC, TF8HCDR20, and tested for ability to bind tissue factor and compete with murine TF8-5G9 for binding. Every version of the CDR-grafted LC, in combination with TF8HCDR20, was shown to bind TF with an affinity comparable to TF8-5G9. Also every CDR-grafted LC version, in combination with TF8HCDR20, was able to compete with murine TF8-5G9 for binding to TF in a manner comparable to the chimeric TF8-5G9 control.

Changes in sequence from murine to human for LC framework positions 39, 41, 46 and 105 did not adversely effect the ability of the antibody to recognize antigen. The CDR-grafted LC of choice was TFBLCDR3, where murine TF8-5G9 sequence was used at positions 39 and 105 because these are in agreement with the human consensus sequence. The preferred CDR-grafted TF8-5G9 antibody is TF8HCDR20 x TF8LCDR3.

The complete sequence of the TF8LCDR3 gene was determined and is shown as a 759 bp EcoR1-BamH1 insert with protein translation in the pEe12TF8LCDR3 expression vector in FIG. 5 and SEQ ID NO: 17.

The essential regions of the gene are as follows:

| Nucleotide # | Region |
|---|---|
| 1-5 | 5' EcoR1 restriction site |
| 6-8 | Kozak sequence |
| 9-68 | Start codon and leader sequence |
| 69-392 | CDR-grafted variable region |
| 393-710 | Human kappa constant region |
| 711-753 | 3' untranslated region |
| 754-759 | 3' BamH1 end spliced to Bc11 site of the expression vector |

Example 8

CDR-Grafted TF8-5G9 Antibody TF8HCDR20 x TF8LCDR3 Inhibits Human Tissue Factor

Figure 6:
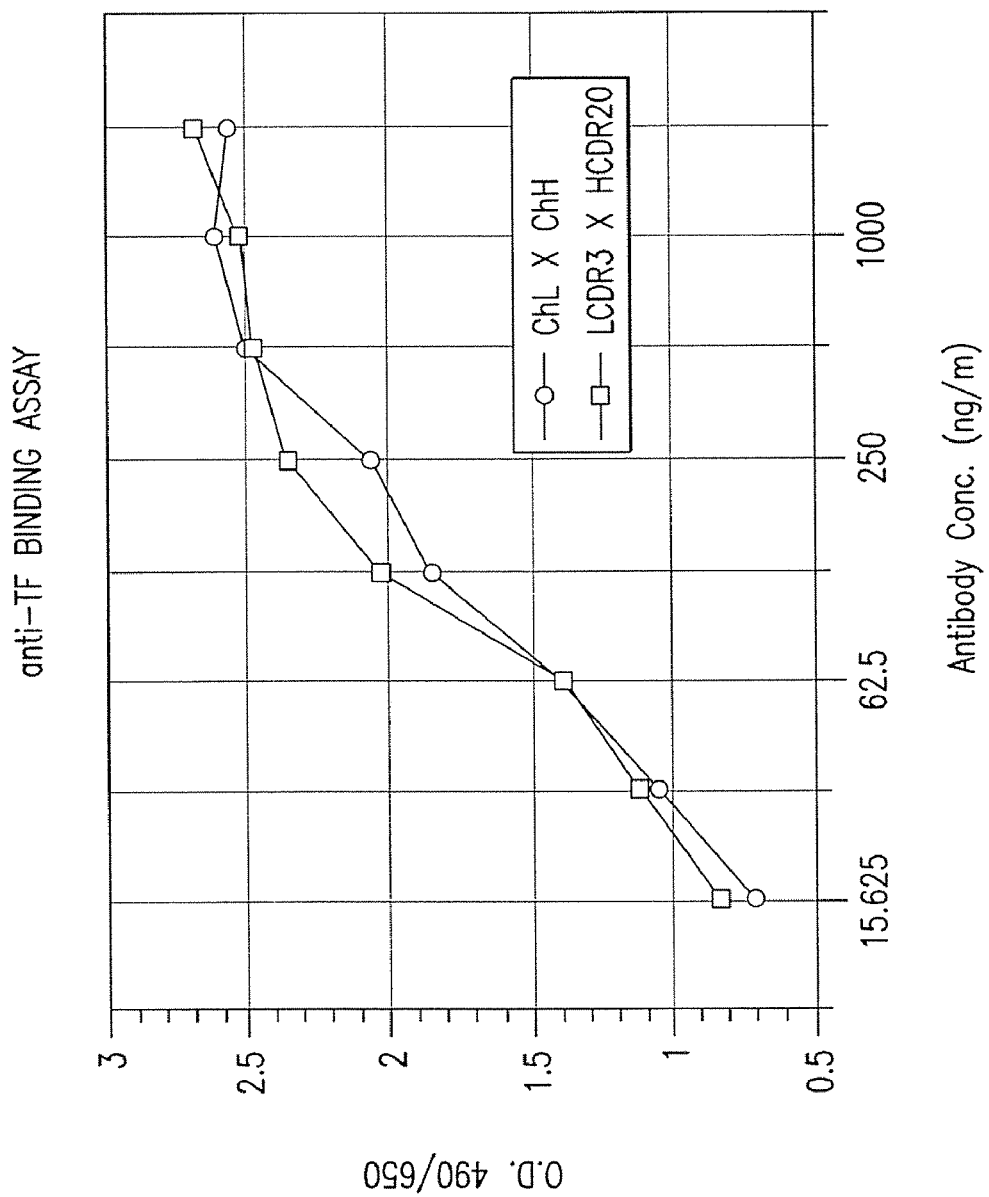
FIG. 6 is a graph depicting the ability of CDR-grafted antibody TF8HCDR20×TF8LCDR3 to bind to human tissue factor.
Figure 7:
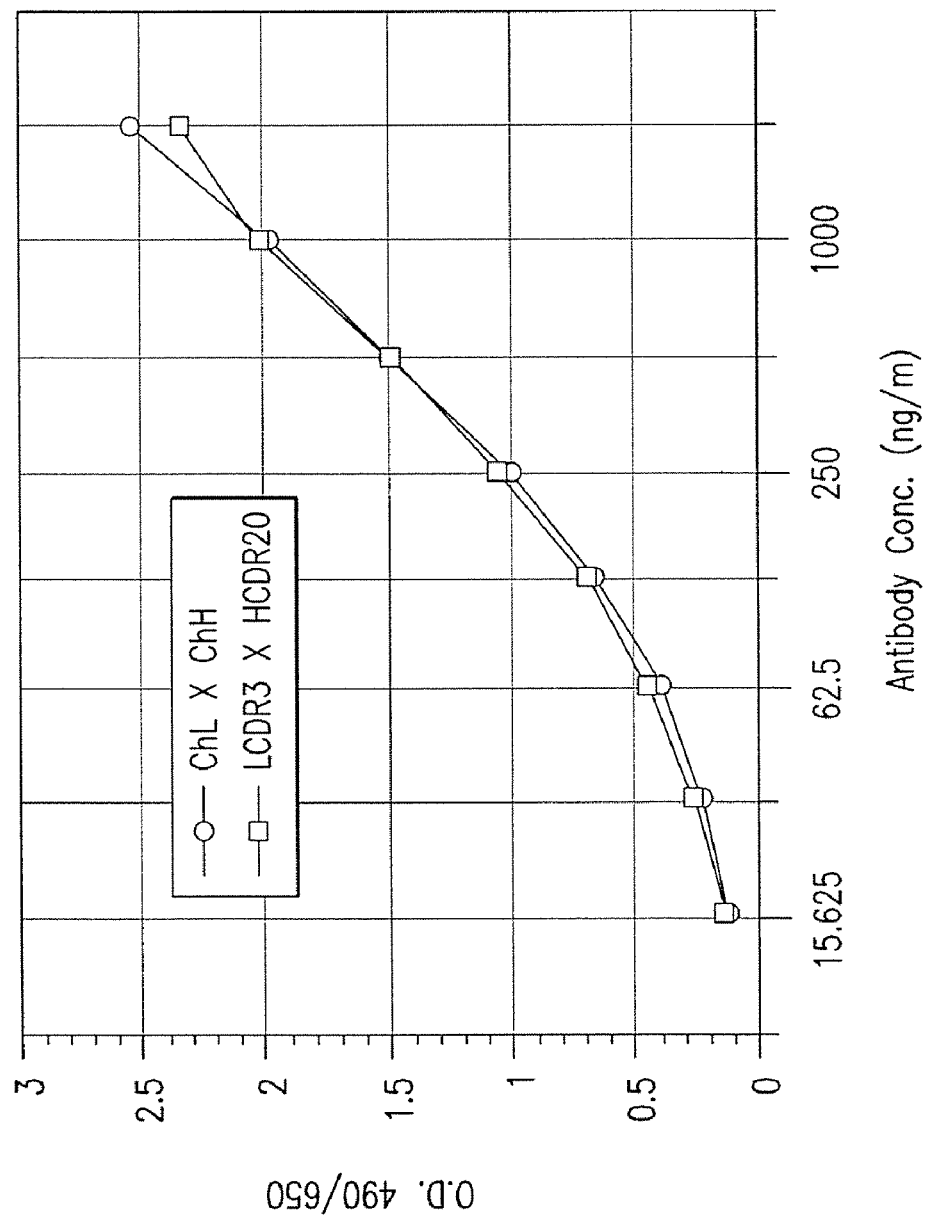
FIG. 7 is a graph depicting the ability of CDR-grafted antibody TF8HCDR20×TF8LCDR3 to compete with murine monoclonal antibody TF85G9 for binding to tissue factor.

The binding of the CDR-grafted TF8-5G9 antibody, TF8HCDR20 x TF8LCDR3, to TF was assessed as described in Example 5 and was found to be comparable to that of the chimeric TF8-5G9 as illustrated in FIG. 6. The ability of the CDR-grafted TF8-5G9 to compete with the murine antibody for binding to TF is comparable to that of the chimeric TF8-5G9 as shown in FIG. 7.

An in vitro assay was used to measure the level of inhibition of factor X activation by the CDR-grafted TF8-5G9 antibody. In this assay, TF forms an active proteolytic complex with factor VII. This complex then converts factor X to factor Xa by proteolysis. The activated Xa enzymatically cleaves a substrate, Spectrozyme FXa, which releases a chromogen. The level of chromogen, as detected by optical density, is an indication of factor X activation due to TF-factor VIIa activity.

The following reaction mixtures were prepared in 12×75 mm borosilicate glass tubes.

25 µl TBS (50 mM Tris, pH 7.4, 150 mM NaCl)

15 µl 20 mM $CaCl_2$/1% bovine serum albumin (BSA)

20 µl human placental tissue factor solution (prepared by reconstituting one vial of Thromborel S, Curtin Matheson Scientific # 269-338 with 4.0 ml $dH_2O$ and diluting 1:10 in TBS)

30 µl Factor VII (Enzyme Research Labs # HFVII 1007 at 237.66 ng/ml in TBS)

Figure 8:
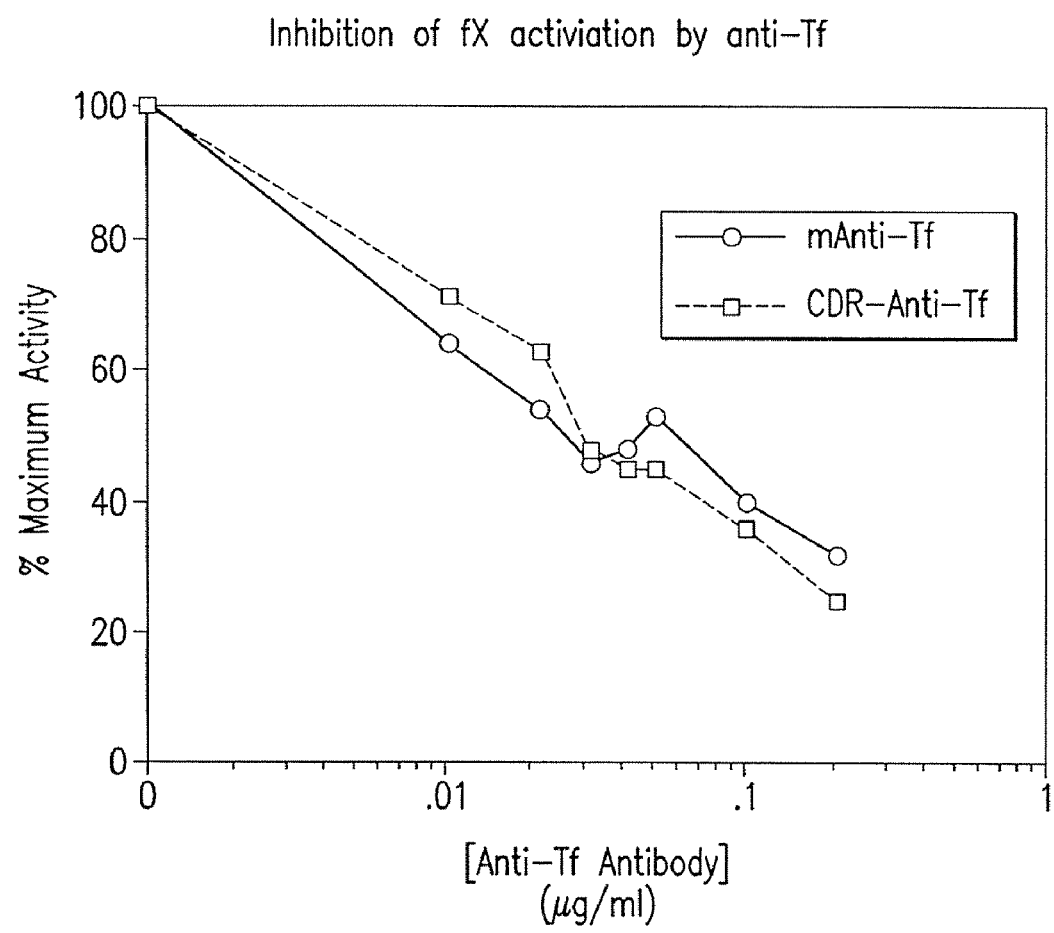
FIG. 8 is a graph depicting the ability of CDR-grafted antibody TF8HCDR20×TF8LCDR3 to inhibit factor X activation.

30 µl TBS or TF8-5G9 or TF8MCDR20×TF8LCDR3 at 1.18 µg/ml or as indicated in FIG. 8

The reaction mixtures were incubated at 37° C. for ten minutes before the addition of Factor X. (In some cases the reaction mixture was preincubated for five minutes before addition of Factor VII or antibody, followed by a ten-minute incubation before addition of Factor X.) Thirty µl of Factor X solution (Enzyme Research Labs, DHFX 330, 247.38 µg/ml TBS) was added and the mixture was incubated at 37 C for three minutes. Factor X activation was terminated by pipetting 40 µg of reaction mixture into 160 µl of stop buffer (50 mM Tris, pH 7.4, 100 mM EDTA, 150 mM NaCl) in 96 well microtiter plates. Each tube of reaction mixture was pipetted into three microtiter wells. Fifty µl of Spectrozyme FXa substrate (American Diagnostica #222, 1 µM/ml TBS) was added to each well $OD_{405}$ was read on a Molecular Devices kinetic plate reader with readings taken every twenty seconds for 10 minutes. Factor X activity was recorded as mOD/minute, and enzyme velocities over the linear portion of the reaction curve were compared to determine inhibition of factor X activation by the anti TF antibodies.

As shown in FIG. 8, the CDR-grafted TF8-5G9 antibody is approximately as effective as the murine TF8-5G9 in inhibiting factor X activation. This indicates that the CDR-grafted TF8-5G9 is functionally active.

Example 9

Figure 9:
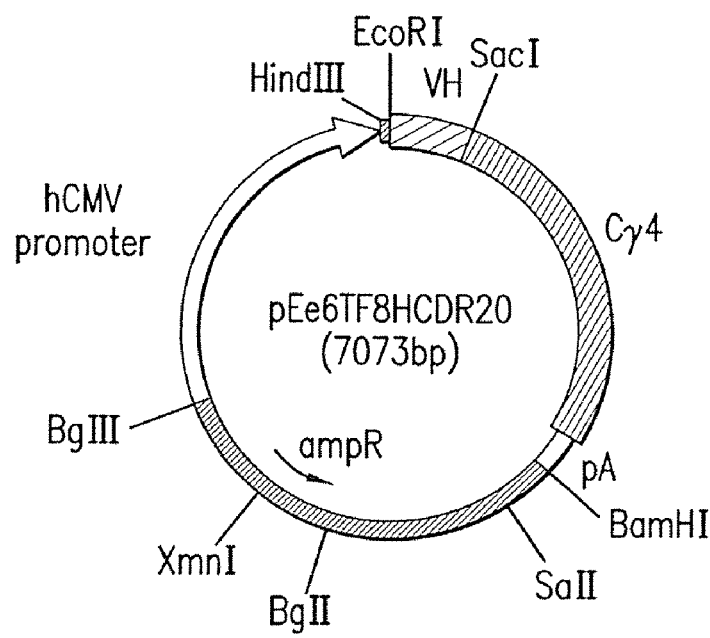
FIG. 9 provides expression vector pEe6TF8HCDR20 resulting from the subcloning of CDR grafted heavy chain TF8HCDR20 into myeloma expression vector pEehCMV-BglI. The following abbreviations are used: VH is the CDR-grafted heavy chain variable region; Cy4 is the human IgG4 constant region; pA is the polyadenylation signal; ampR is the B-lactamase gene; and hCMV is human cytomegalovirus.
Figure 10:
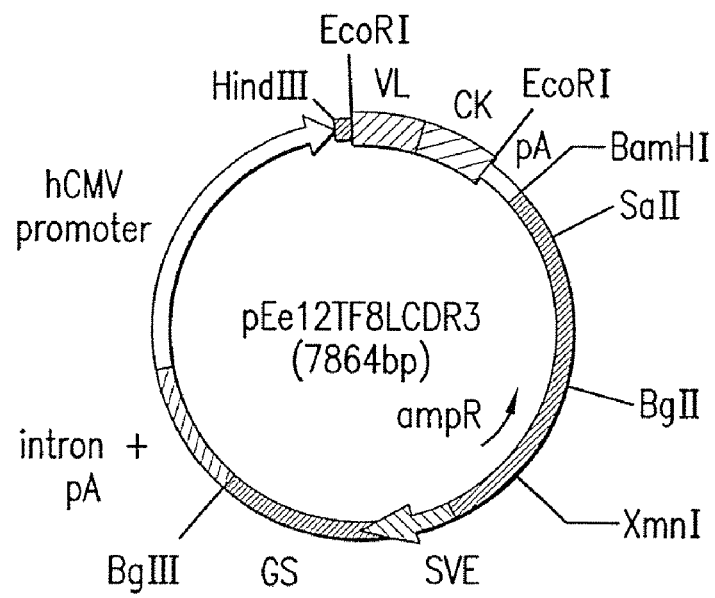
FIG. 10 provides expression vector pEe12TF8LCRD3 resulting from the subcloning of CDR grafted light chain TF8LCDR3 into myeloma expression vector pEe12. The following abbreviations are used: VL is the CDR-grafted light chain variable region; CK is the human kappa constant region; SVE is the SV40 early promoter; GS is glutamine synthetase cDNA. Other abbreviations are as noted in FIG. 9.

Construction of the CDR-Grafted Heavy and Light Chain Myeloma Expression Vectors For the purpose of establishing a permanent CDR-grafted antibody-producing cell line, the TF8HCDR20 and TF8LCDR3 genes were subcloned into myeloma cell expression vectors. The heavy chain TF8HCDR20 was subcloned into the EcoRI and BclI sites of the pEe6hCMVBg1II myeloma expression vector described by Stephens et al. (1989) *Nucleic Acids Res.* 17:7110 to produce pEe6TF8HCDR20. The light chain TF8LCDR3 was subcloned into the EcoTI and Bc1I sites of the pEe12 myeloma expression vector to produce pEe12TF8LCDR3. The heavy and light chain expression vectors are illustrated in FIGS. 9 and 10, respectively. In both vectors antibody gene transcription was driven by the human cytomegalovirus (hCMV) promoter-enhancer, which lies directly 5' to the multiple cloning site. The polyadenylation signal sequence lies 3' to the multiple cloning site and signals the termination of transcription. Each vector contains the B-lactamase gene to allow for ampicillin selection in *E. coli*. The pEe12 vector contains a glutamine synthetase cDNA gene under the transcriptional control of the SV40 early promoter. Glutamine synthetase allows for myeloma cell transfectants to be selected in glutamine-free media. Myeloma cells are devoid of glutamine synthetase activity and are dependent on a supply of glutamine in the culture media. Cells which have been transfected with the pEe12 vector, containing the glutamine synthetase gene, are able to synthesize glutamine from glutamate and can survive in the absence of glutamine.

The pEe6TF8HCDR20 expression vector is a 7073 bp plasmid whose DNA sequence is shown in FIG. 4 and SEQ ID NO:15. The coding regions of the TF8HCDR20 gene are translated. The essential regions of this vector are described below:

1. Nucleotides #1-2360: The TF8HCDR20 CDR-grafted HC gene is described in Example 6. The HC gene was inserted as an EcoRI/BamHI fragment into the EcoRI/BclI sites of the pEe6hCMVBgII vector.
2. Nucleotides #2361-2593: This region encodes the SV40 early gene polyadenylation signal (SV40 nucleotides 2770-2537), which acts as a transcriptional terminator. This fragment is flanked by a 5' Bell site and a 3' BamHI site. The 3' BamHI end of the heavy chain gene was spliced to the 5' BclI site of the polyadenylation signal, thus eliminating both sites.
3. Nucleotides #2594-3848: This region is a BamHI-Bg1-I fragment from pBR328 (nucleotides 375-2422) but with a deletion between the SaI and AvaI sites (pBR328 nucleotides 651-1425) following the addition of a SalI linker to the AvaI site. This region contains the Col E1 bacterial origin of replication.
4. Nucleotides #3849-4327: This is a BglI-XmnI fragment site from the B-lactamase gene of pSP64 (promega Corporation, Madison, Wis.). This gene provides ampicillin resistance to bacteria transformed with this vector.
5. Nucleotides #4328-4885: This is an XmnIHindIII fragment of the Co1E1 based plasmid pCT54 described by Emtage et al. (1983) *Proc. Natl. Acad. Sci. USA* 80:3671. The HindIII site was converted to a Bq1II site by the addition of a linker following the addition of the hCMV promoter described below.
6. Nucleotides #4886-7022: These nucleotides encode the Pst-1m fragment of human cytomeglovirus (hCMV) strain AD 169 described by Greenway et al. (1982) *Gene* 18:355 containing the region coding for the hCMV middle intermediate early promoter. This Pst-1m fragment was cloned into the HindIII site of pEe6hCMV by addition of oligonucleotides of the following sequence to either end of the fragment:
   5' GTCACCGTCCTTGACACGA 3' (SEQ ID NO:21)
   3' ACGTCAGTGGCAGGAACTGTGCTTCGA 5' (SEQ ID NO:22)
   The resulting 2100 bp fragment was inserted such that the promoter directed transcription towards the EcoRI site of pEe6hCMV. The oligonucleotide above served to recreate the complete 5' untranslated sequence of the hCMV-MIE gene the added irrelevant sequence at the very 5' end of the fragment. The HindIII site at the 5' end was subsequently converted to a BglII site by the addition of a further linker.
7. Nucleotides #7023-7073: The pSP64 polylinker with the BamHI and Sal1 sites removed.

The pEe12TF8LCDR3 expression vector is a 7864 bp plasmid whose DNA sequence is shown in FIG. 5 and SEQ ID NO:17. The coding regions of the TF8LCDR3 gene are translated. The essential regions of this expression vector are described below:

1. Nucleotides #1-759: The TF8LCDR3CDR-grafted LC gene is described in Example 7. The gene was inserted as an EcoRI/BamHI fragment into the EcoRI/BclII sites of the pEe12 expression vector.
2. Nucleotides #760-3284: These regions of pEe12 are identical to the regions encoded by nucleotides 2361-4885 of the pEe6TF8HCDR20 (regions #2-5).
3. Nucleotides #3285-5736: This region encodes the Chinese hamster ovary glutamine synthetase cDNA under the transcriptional control of the SV40 early promoter and followed by the SV40 polyadenylation an splice signals from the pSV2.dhfr vector described by Subramani et al. (1981) *Mol. Cell. Biol.* 1:854. The following describes the derivation of this region: A 1200 bpNaeI-PvuII fragment, containing a complete GS coding sequence, was excised from the Chinese hamster ovary cDNA clone AGS 1.1 described by Hayward et al. (1986) *Nucleic Acid Res.* 14:999. After addition of a HindIII linker-to the NaeI site and a Bg1II linker to the PvuII site (hence destroying the NaeI and PvuII sites), the 1200 bp fragment was cloned in place of DHFR sequences in pSV2.dhfr between the HindIII and Bg1II sites to form pSV2.GS. The single remaining PvuII site in pSV2BamGS was converted to a BamHI site by addition of an oligonucleotide linker to form pSV2BamGS. An EcoRI site in the GS cDNA was destroyed by site directed mutagenesis without altering the amino acid sequence in pSV2BamGS and the HindIII site was destroyed by filling in with DNa polymerase I. The 2451 bp BamHI fragment from this plasmid, containing the complete SV40-GS hybrid transcription unit, was excised and inserted at the Bq1II site of pEe6hCMV-Bg1II site of pEe6hCMV-Bg1II such that transcription from the sV40 early promoter proceeds towards the hCMV promoter.
4. Nucleotides #5737-7864: This region is identical to the hCMV promoter and pSP64 polylinker encoded by nucleotides 4886-7073 of the pEe6TF8HCDR20 vector described above (regions 6 and 7).

For the purpose of ensuring that both the pEe6TF8HCDR20 and peE12TF8LCDR3 vectors co-transfected myeloma cells, the vectors were joined in linear concatamers. Both the pEe6TF8HCDR20 and pEe12TF8LCDR3 vectors were digested at the unique Sal1 site. The Sal1 linearized pEe6TF8HCDR20 vector was phosphatased at its 5' ends to prohibit ligation of two pEe6TF8HCDR20 vectors onto each other. This phosphatased HC vector was ligated in a 2:1 molar ratio to the Sa1 linearized pEe12TF8LCDR3. The resulting concatamers were most likely of the following composition:

This concatamerized DNA was extracted with phenol and chloroform, and precipitated with ammonium acetate and ethanol. The DNA precipitate was resuspended in distilled water to a concentration of 1 µg/µL and used to transfect myeloma cells.

Example 10

Development of NSO Expression Cell Lines

Stably transformed cell lines expressing the humanized TF8-5G9 antibody were prepared by transfecting CDR-grafted heavy and light chain expression vectors into NSO mouse myeloma cells. Selection of transfected cells was carried out using the dominant selectable marker gene, glutamine synthetase (GS).

The NSO mouse myeloma cell line, obtained from Celltech, Ltd., is a subclone derived from NS-1 and does not express intracellular light chains. These cells were cultured in Dulbecco's modified Eagle's medium (DMEM) with added glutamine and 10% fetal bovine serum (FBS). To prepare for transfection, the cells were harvested in mid-log phase of the growth cycle, centrifuged for 5 minutes, washed with phosphate buffered saline (PBS), centrifuged again, and the cell pellet was resuspended in 2.2 mL of PSS. The final cell concentration was 2.18×107 mL. Cells were maintained on ice during the entire procedure.

The DNA to be transfected (pEe12TF8LCDR3 x pEe6TFBHCDR20) was prepared as a concatamer as described in Example 9. The DNA and NSO cells were added to a 0.4 cm BioRad Gene Pulse cuvette in the following order:

40 μL (40 μg) DNA concatamer
320 μL double distilled water
40 μL 10×PBS
400 μL NSO cells (8.72×106 cells).

Transfection was performed by electroporation following a protocol provided by Celltech, Ltd. In this procedure, the cells and DNA in PBS buffer were exposed to a brief, high voltage pulse of electricity causing transient micropores to form on the cell membrane. DNA transfer takes place through these openings. To prepare for electroporation, the suspension of NSO cells and DNA was gently mixed and incubated on ice for 5 minutes. The cuvette was placed in a BioRad Gene Pulser and given 2 consecutive electrical pulses at settings of 3 μF (capacitance) and 1.5V (voltage). Following electroporation, the cuvette was returned to the ice for 5 minutes. The suspension was then diluted in prewarmed growth medium and distributed into seven 96-well plates. Control plates containing cells electroporated without DNA were also prepared at the same time to measure the presence of spontaneous mutants. Plates were placed in a 37° C. incubator with 5% $CO_2$.

Glutamine synthetase, encoded by the GS gene, is an enzyme that converts glutamate to glutamine. NSO cells require glutamine for growth due to inadequate levels of endogenous GS gene expression. In the DNA concatamer, this gene is located on the pEe12TF8LCDR3 vector. Transfected cells which incorporate the GS gene become glutamine-independent. Cells not integrating the GS gene into their genome would remain glutamine dependent and would not survive in glutamine-free medium. Approximately 18 hours post electroporation, all plates were fed with glutamine-free selection medium and returned to the incubator until visible colonies appeared.

Approximately 3 weeks after transfection, distinct macroscopic colonies were observed. These were screened for expression of the intact humanized antibody using the assembly ELISA as described in Example 5.

Tissue culture supernatants from wells containing 1 colony were screened at a 1:10 dilution. Positive wells showing activity greater than the 25 ng/mL standard were subcultured and expanded for further analysis.

For selection of high producers, antibody production was quantitated after a 96 hour growth period. Tissue culture flasks were seeded with $2 \times 10^5$ cells/mL in 10 mL of selection medium and incubated at 37° C., 5% $CO_2$ for 96 hours. At the end of that time period, an aliquot was taken to determine cell concentration and antibody titer. Evaluation of antibody production was calculated as μg/mL and pg/cell/96 hours. The highest producers from this transfection were:

| Cell Line | μg/mL | pg/cell/96 hour |
|---|---|---|
| 2B1 | 26.3 | 24.3 |
| 3E11 | 27.6 | 59.9 |
| 4G6 | 30.2 | 41.9 |

Example 11

CDR-Grafted Antibody TF8HCDR20 x TF8LCDR3 Inhibits Tissue Factor in Vivo

CDR-grafted antibody TF8HCDR20×TF8LCDR3 was compared to murine antibody TF8-5G9 for its ability to protect rats from experimentally induced disseminated intravascular coagulation (DIC). In the DIC model, rats are challenged with human thromboplastin (a crude tissue extract containing TF activity), resulting in fibrinogen consumption and death. Pretreatment of rats with antiTF antibody was demonstrated to protect rats from fibrinogen consumption and death as follows.

Human thromboplastin was prepared as described in U.S. Pat. No. 5,223,427. Saline control or 30μ/ml of TF8-5G9 or CDR-grafted antibody was injected through the tail vein of rats, followed by injection of thromboplastin equivalent to 200 ng of recombinant TF. Clotting times were determined at T=O and T=1 minute as a measure of fibrinogen concentration. Clotting times are proportional to fibrinogen concentration, with a 60 second clotting time corresponding to an 80% reduction in fibrinogen concentration. Clotting times of greater than 60 seconds cannot be accurately measured and were recorded as 60 seconds. Survivability and clotting times for three representative studies are shown below.

| Study | Controls | Survivors TF8-5G9 | CDR-grafted Ab |
|---|---|---|---|
| 1 | 0/8 | 5/8 | 6/8 |
| 2 | 0/8 | 4/7 | 7/8 |
| 3 | 0/8 | 8/8 | 3/7 |

| Clotting Times | | | | | |
|---|---|---|---|---|---|
| Study #1 | | Study #2 | | Study #3 | |
| T = O | T = 1 | T = O | T = 1 | T = O | T = 1 |
| Controls | | | | | |
| 16 | >60 | 18 | >60 | 19 | >60 |
| 16 | >60 | 18 | >60 | 21 | >60 |
| 16 | >60 | 18 | >60 | 18 | >60 |
| 17 | >60 | 18 | >60 | 19 | >60 |
| 15 | >60 | 16 | >60 | 18 | 54 |
| 16 | >60 | 18 | >60 | 18 | >60 |
| 16 | >60 | 17 | >60 | 18 | >60 |
| 16 | >60 | 17 | >60 | 18 | >60 |
| Murine TF8-5G9 | | | | | |
| 16 | 36 | 18 | 34 | 19 | 28 |
| 15 | 41 | 18 | 36 | 18 | 29 |
| 15 | 33 | 18 | >60 | 19 | 29 |
| 15 | 31 | 17 | >60 | 18 | 29 |
| 15 | >60 | 18 | 50 | 18 | 28 |
| 16 | >60 | 17 | 34 | 19 | 40 |
| 16 | 33 | 17 | 34 | 19 | 40 |
| 16 | 33 | 18 | 31 | 19 | 34 |
| 16 | >60 | | | 19 | >60 |

-continued

| CDR-grafted TF8-5G9 | | | | | |
|---|---|---|---|---|---|
| 16 | >60 | 17 | >60 | 21 | >60 |
| 16 | >60 | 17 | 33 | 18 | 34 |
| 16 | >60 | 18 | 32 | 17 | >60 |
| 22 | 37 | 18 | >60 | 20 | 35 |
| 16 | 32 | 17 | 32 | 17 | 58 |
| 15 | >60 | 18 | 31 | 18 | 33 |
| 16 | >60 | 17 | 31 | 18 | 31 |
| 16 | >60 | 16 | 32 | | |

Twenty-three of the twenty-four control rats had clotting times of greater than 60 seconds indicating that virtually all untreated rats were consuming more than 80% of their fibrinogen. Both the COR-grafted and murine antibody treated rats had similar clotting times at one minute of 44.5 and 40 seconds. Further, only six of the murine antibody treated rats and nine of the COR-grafted antibody treated rats had clotting times in excess of 60 seconds. Accordingly, both the murine and CDR-grafted antibodies were able to neutralize TF and thus protect rats from fibrinogen consumption and death.

The invention claimed is:

1. A method of making a CDR-grafted antibody capable of inhibiting human tissue factor, wherein the complementarity determining regions (CDRs) are obtained from a murine monoclonal antibody against human tissue factor and the constant (C) and framework (FR) regions are obtained from one or more human antibodies, wherein said CDRs of the heavy chain have the amino acid sequences:

```
    CDR1    DYYMH               (SEQ ID NO: 5)
    CDR2    LIDPENGNTIYDPKFQG   (SEQ ID NO: 6)
    CDR3    DNSYYFDY            (SEQ ID NO: 7)
``` and said CDRs of the light chain have the amino acid sequences:

```
    CDR1    KASQDIRKYLN         (SEQ ID NO: 8)
    CDR2    YATSLAD             (SEQ ID NO: 9)
    CDR3    LQHGESPYT           (SEQ ID NO: 10)
``` wherein the heavy chain comprises residues obtained from the murine monoclonal antibody at positions 23, 24, 28, 29, 30, 48, 49, 71, 88 and 91 and the light chain comprises residues obtained from the murine monoclonal antibody at positions 39 and 105, wherein the residues are numbered according to the Kabat numbering system, comprising cotransfecting a host cell with an expression vector comprising a nucleic acid encoding the CDR-grafted antibody heavy chain and an expression vector comprising a nucleic acid encoding the CDR-grafted antibody light chain; culturing the transfected host cell; and recovering said CDR-grafted antibody.

2. A method of making the CDR-grafted antibody of claim 1 comprising transfecting a host cell with an expression vector comprising a nucleic acid encoding the CDR-grafted antibody heavy chain and a nucleic acid encoding the CDR-grafted antibody light chain; culturing the transfected host cell; and recovering said CDR-grafted antibody.

3. The method of any one of claims 1 to 2 wherein said host cell is a bacterial cell, a yeast cell, an insect cell or a mammalian cell, such as a CHO cell, a COS cell or a myeloma cell.

* * * * *